United States Patent
Koshimoto et al.

(10) Patent No.: US 11,891,602 B2
(45) Date of Patent: Feb. 6, 2024

(54) METHOD OF PRODUCING HAIRPIN SINGLE-STRANDED RNA MOLECULES

(71) Applicant: Toray Industries, Inc., Tokyo (JP)

(72) Inventors: Kyohei Koshimoto, Kamakura (JP); Katsuhiko Iseki, Otsu (JP); Hideaki Inada, Tokyo (JP); Tatsuya Fujita, Kamakura (JP); Keiichi Okimura, Kamakura (JP); Munetaka Kunishima, Kanazawa (JP); Tadaaki Ohgi, Kurume (JP); Eriko Aoki, Kurume (JP)

(73) Assignee: Toray Industries, Inc., Tokyo (JP)

( * ) Notice: Subject to any disclaimer, the term of this patent is extended or adjusted under 35 U.S.C. 154(b) by 135 days.

(21) Appl. No.: 17/276,194

(22) PCT Filed: Oct. 2, 2019

(86) PCT No.: PCT/JP2019/038860
§ 371 (c)(1),
(2) Date: Mar. 15, 2021

(87) PCT Pub. No.: WO2020/071407
PCT Pub. Date: Apr. 9, 2020

(65) Prior Publication Data
US 2021/0317495 A1      Oct. 14, 2021

(30) Foreign Application Priority Data

Oct. 2, 2018   (JP) .................. 2018-187767

(51) Int. Cl.
*C12N 15/113* (2010.01)
(52) U.S. Cl.
CPC ...... *C12N 15/113* (2013.01); *C12N 2310/531* (2013.01); *C12N 2330/30* (2013.01)
(58) Field of Classification Search
None
See application file for complete search history.

(56) References Cited

U.S. PATENT DOCUMENTS

| | | |
|---|---|---|
| 2004/0058886 A1 | 3/2004 | Scaringe |
| 2012/0010271 A1 | 1/2012 | Ohgi et al. |
| 2012/0035246 A1 | 2/2012 | Ohgi et al. |
| 2014/0329886 A1 | 11/2014 | Ohgi et al. |
| 2021/0024930 A1 | 1/2021 | Inada et al. |

FOREIGN PATENT DOCUMENTS

| | | |
|---|---|---|
| CN | 104039961 A | 9/2014 |
| EP | 3 369 816 A1 | 9/2018 |
| EP | 3 778 914 A1 | 2/2021 |
| JP | 2013-153736 A | 8/2013 |
| JP | 2016-141618 A | 8/2016 |
| WO | 2012/005368 A1 | 1/2012 |
| WO | 2012/017919 A1 | 2/2012 |
| WO | 2015/093495 A1 | 6/2015 |
| WO | 2017/035090 A1 | 3/2017 |
| WO | 2019/189591 A1 | 10/2019 |
| WO | 2019/189722 A1 | 10/2019 |

OTHER PUBLICATIONS

Andrew Fire et al., "Potent and specific genetic interference by double-stranded RNA in *Caenorhabdins elegans*," Nature, vol. 391, Feb. 19, 1998, pp. 806-811.
Yu Liu et al., "2′,2′-Ligat on demonstrates the thermal dependence of DNA-directed positional control," Tetrahedron, vol. 64, 2008, pp. 8417-8422.
Guidebook for the Synthesis of Oligonucleotides, Product Guide 2015/16, Link Technologies Ltd., vol. 58, 2017, pp. 49-51.
Matthew Badland et al., "A comparative study of amide-bond forming reagents in aqueous media—Substrate scope and reagent compatibility," Tetradedron Letters, vol. 58, 2017, pp. 4391-4394.
Extended European Search Report dated Apr. 13, 2023, of counterpart European Patent Application No. 19869898.7.
Hamasaki et al, "Efficacy of a Novel Class of RNA Interference Therapeutic Agents,"PLOS One, vol. 7, No. 8., pp. 1-16, 2012.
First Office Action dated Aug. 10, 2023, of counterpart Chinese Patent Application No. 201980061140.0, along with an English machine translation.

*Primary Examiner* — Patrick T Lewis
(74) *Attorney, Agent, or Firm* — DLA Piper LLP (US)

(57) ABSTRACT

A method produces a hairpin single-stranded RNA molecule capable of inhibiting expression of a target gene, including the step of reacting a first single-stranded oligo-RNA molecule represented by formula (I) with a second single-stranded oligo-RNA molecule represented by formula (II) in a mixed solvent including a buffer solution and a hydrophilic organic solvent in the presence of a dehydration condensation agent: 5′-Xc-Lx$^1$ (I) and Lx$^2$-X—Y-Ly-Yc-3′ (II), wherein the dehydration condensation agent is selected from the group consisting of a triazine-based dehydration condensation agent, a uronium-based dehydration condensation agent including an N-hydroxy nitrogen-containing aromatic ring structure, a carbodiimide-based dehydration condensation agent, a 2-halopyridinium-based dehydration condensation agent, and a formamidinium-based dehydration condensation agent.

15 Claims, 2 Drawing Sheets
Specification includes a Sequence Listing.

METHOD OF PRODUCING HAIRPIN SINGLE-STRANDED RNA MOLECULES

TECHNICAL FIELD

This disclosure relates to a method of producing a hairpin single-stranded RNA molecule.

BACKGROUND

As a gene expression-inhibiting technology, RNA interference (RNAi), for instance, has been known (Fire et al., Nature, 1998, Vol. 391, pp 806-811). For RNA interference-mediated gene expression inhibiting, widely used is a protocol using a short double-stranded RNA molecule called siRNA (small interfering RNA). In addition, a technique for inhibiting gene expression using a circular RNA molecule in which a double strand is partially formed by intramolecular annealing is reported (US Patent Application Publication No. 2004/058886).

However, siRNA has low stability in vivo, and siRNA is easily dissociated into single-stranded RNAs. Thus, it is difficult to stably inhibit gene expression. International Publication WO 2012/017919 reports that siRNA can be stabilized in a hairpin single-stranded long-chain RNA molecule in which a sense strand and an antisense strand of siRNA are linked via one or two linkers formed using an amino acid derivative, to produce a single strand. As a method of producing such a single-stranded long-chain RNA molecule, a solid-phase synthesis scheme by phosphoramidite chemistry is described in WO '919.

Liu et al., Tetrahedron, 2008, Vol. 64, pp 8417-8422 reports, as a method of producing a long-chain DNA molecule, a production technique of separately synthesizing a pair of two oligo-DNA molecules having a relatively short chain, i.e., a first oligoDNA molecule having a carboxyl group at the end and a second oligoDNA molecule having an amino group at the end, and linking the two molecules by amidation in a buffer solution containing a triazine-based dehydration condensation agent, though making no mention about RNA molecules.

Meanwhile, amidation reaction in an aqueous solvent is reported in, for instance, Badland et al., Tetrahedron Letters, 2017, Vol. 58, pp 4391-4394, which however makes no mention about RNA molecules.

HATU is illustrated as a peptide coupling agent which is used for forming an amide bond between a carboxylic acid of an oligomer containing carboxylic acid at the 5' end and a label (e.g., an amino group-containing substance such as cyanine, an amino acid, or a peptide) during solid-phase synthesis (Guidebook for the Synthesis of Oligonucleotides, Product Guide 2015/16, Link Technologies Ltd., 2017, Vol. 58, pp 49-51).

It could therefore be helpful to provide an efficient method of producing a hairpin single-stranded RNA molecule capable of inhibiting expression of a target gene.

SUMMARY

A conventional method of producing a hairpin single-stranded RNA molecule capable of inhibiting expression of a target gene involves extending nucleoside units one by one with phosphoramidite chemistry and is thus not an efficient method.

For the purpose of developing an efficient method of producing a hairpin single-stranded RNA molecule capable of inhibiting expression of a target gene, we applied a synthesis technique of Liu et al. to the synthesis of the hairpin single-stranded RNA molecule. However, the molecule of interest was not obtained with a high yield due to large amounts of impurities produced because a large number of hydroxyl groups responsible for side reaction in amidation reaction are present in the RNA molecule.

We then found that a hairpin single-stranded RNA molecule can be efficiently produced with a high yield by an amidation reaction of the terminus of two single-stranded oligo-RNA molecules using a certain type of dehydration condensation agent in a mixed solvent comprising a buffer solution and a hydrophilic organic solvent such as dimethyl sulfoxide.

Literature (Nucleic Acid Research, 1990, Vol. 391, p. 4953; Kiso Bunshi Seibutsugaku (Basic Molecular Biology), 4th edition, Tamura, et al., 2016, Tokyo Kagaku Dojin Co., Ltd. and the like) teaches that an organic solvent such as dimethyl sulfoxide is used as a nucleic acid-denaturating agent, and thus such an organic solvent is known to destabilize nucleic acid annealing. Thus, our findings are surprising.

We thus provide:

[1] A method of producing a hairpin single-stranded RNA molecule capable of inhibiting expression of a target gene, comprising the step of reacting a first single-stranded oligo-RNA molecule represented by formula (I) with a second single-stranded oligo-RNA molecule represented by formula (II) in a mixed solvent comprising a buffer solution and a hydrophilic organic solvent in the presence of a dehydration condensation agent:

$$5'\text{-Xc-Lx}^1 \quad \quad \quad (I)$$

$$\text{Lx}^2\text{-X—Y-Ly-Yc-3'} \quad \quad \quad (II)$$

wherein, in formula (I) or (II), X, Xc, Y and Yc each is composed of a ribonucleotide residue, Xc is complementary to X, Yc is complementary to Y, Ly is a non-nucleotide linker, $Lx^1$ is a non-nucleotide linker having an amino group, $Lx^2$ is a non-nucleotide linker having a carboxyl group, and X—Y comprises a gene expression-inhibiting sequence for the target gene, the dehydration condensation agent is selected from the group consisting of a triazine-based dehydration condensation agent, a uronium-based dehydration condensation agent comprising an N-hydroxy nitrogen-containing aromatic ring structure, a carbodiimide-based dehydration condensation agent, a 2-halopyridinium-based dehydration condensation agent, and a formamidinium-based dehydration condensation agent, if the dehydration condensation agent is the carbodiimide-based dehydration condensation agent, the dehydration condensation agent is used in combination with an N-hydroxy nitrogen-containing aromatic compound or a cyano(hydroxyimino)acetic acid ester, if the dehydration condensation agent is the 2-halopyridinium-based dehydration condensation agent, the dehydration condensation agent is used in combination with an N-hydroxy nitrogen-containing aromatic compound, and if the dehydration condensation agent is the formamidinium-based dehydration condensation agent, the dehydration condensation agent is used in combination with an N-hydroxy nitrogen-containing aromatic compound or an N-hydrocarbon-substituted imidazole derivative.

[2] The method according to [1], wherein the linker Ly is a non-nucleotide linker having an amino acid backbone or an amino alcohol backbone, and the linker $Lx^2$ is a non-nucleotide linker having an amino acid backbone.

[3] The method according to [1] or [2], wherein the Ly is a non-nucleotide linker comprising at least one of a pyrrolidine backbone or a piperidine backbone, or a non-nucleotide linker comprising —NHCH$_2$COO—, and the $Lx^2$ is a non-nucleotide linker comprising at least one of a pyrrolidine backbone or a piperidine backbone and having a carboxyl group, or a non-nucleotide linker comprising —NHCH$_2$COOH.

[4] The method according to any of [1] to [3], wherein the $Lx^1$ is represented by formula (III):

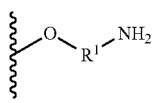

(III)

wherein, in formula (III), $R^1$ is an optionally substituted alkylene chain, and —$OR^1$ is bonded to the 3' end of Xc via a phosphodiester bond, and the $Lx^2$ is represented by formula (IV) or formula (IV'):

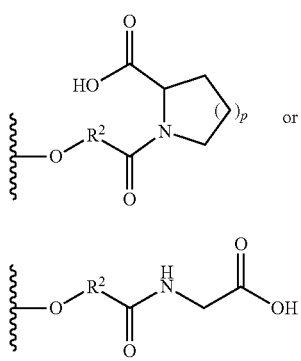

wherein, in formula (IV), $R^2$ is an optionally substituted alkylene chain, p is 1 or 2, and —$OR^2$ is bonded to the 5' end of X via a phosphodiester bond; and in formula (IV'), $R^2$ is an optionally substituted alkylene chain, and —$OR^2$ is bonded to the 5' end of X via a phosphodiester bond.

[5] The method according to any of [1] to [4], wherein:
(i) the uronium-based dehydration condensation agent comprising an N-hydroxy nitrogen-containing aromatic ring structure is a benzotriazolyluronium-based dehydration condensation agent,
(ii) the N-hydroxy nitrogen-containing aromatic compound is hydroxybenzotriazole or a derivative thereof,
(iii) the cyano(hydroxyimino)acetic acid ester is a cyano(hydroxyimino)acetic acid alkyl ester, and
(iv) the N-hydrocarbon-substituted imidazole derivative is an N-alkylimidazole derivative.

[6] The method according to any of [1] to [5], wherein the hydrophilic organic solvent is a hydrophilic aprotic organic solvent.

[7] The method according to [6], wherein the hydrophilic aprotic organic solvent is dimethyl sulfoxide, N,N-dimethylformamide, N,N'-dimethylethyleneurea, or acetonitrile.

[8] The method according to any of [1] to [7],
wherein the dehydration condensation agent is 4-(4,6-dimethoxy-1,3,5-triazin-2-yl)-4-methylmorpholinium chloride, O-(7-azabenzotriazol-1-yl)-N,N,N',N'-tetramethyluronium hexafluorophosphate, N-(3'-dimethylaminopropyl)-N'-ethylcarbodiimide hydrochloride, 2-chloro-1-methylpyridinium iodide, or chloro-N,N,N',N'-tetramethylformamidinium hexafluorophosphate,
the N-hydroxy nitrogen-containing aromatic compound is 1-hydroxy-7-azabenzotriazole,
the cyano(hydroxyimino)acetic acid ester is ethyl cyano(hydroxyimino)acetate, and
the N-hydrocarbon-substituted imidazole derivative is N-methylimidazole.

[9] The method according to [7] or [8], wherein the combination of the dehydration condensation agent and the hydrophilic aprotic organic solvent is a combination of O-(7-azabenzotriazol-1-yl)-N,N,N',N'-tetramethyluronium hexafluorophosphate and dimethyl sulfoxide, a combination of O-(7-azabenzotriazol-1-yl)-N,N,N',N'-tetramethyluronium hexafluorophosphate and N,N-dimethylformamide, a combination of N-(3'-dimethylaminopropyl)-N'-ethylcarbodiimide hydrochloride, 1-hydroxy-7-azabenzotriazole and dimethyl sulfoxide, or a combination of chloro-N,N,N',N'-tetramethylformamidinium hexafluorophosphate, 1-hydroxy-7-azabenzotriazole and dimethyl sulfoxide.

[10] The method according to any of [1] to [9], wherein pH of the buffer solution is from 6.5 to 7.5.

[11] The method according to any of [1] to [10], wherein the Ly is a non-nucleotide linker comprising a pyrrolidine backbone or a piperidine backbone, the $Lx^1$ is a non-nucleotide linker having an amino group, and the $Lx^2$ is a non-nucleotide linker comprising at least one of a pyrrolidine backbone or a piperidine backbone and having a carboxyl group.

[12] The method according to any of [1] to [11], wherein the Ly is represented by formula (V):

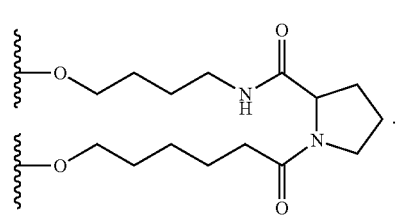

(V)

[13] The method according to any of [1] to [12], wherein the $Lx^1$ is represented by formula (VI):

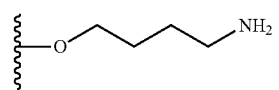

(VI)

and the $Lx^2$ is represented by formula (VII):

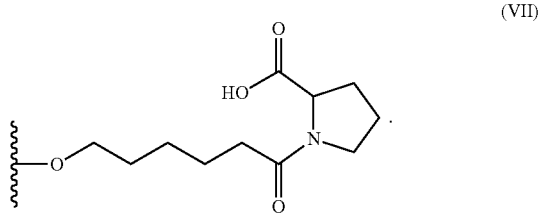 [SMILES: *OCCCCCC(=O)N1CCCC1C(=O)O]

(VII)

[14] The method according to any of [1] to [13], wherein the target gene is TGF-β1 gene.
[15] The method according to any of [1] to [14], wherein the hairpin single-stranded RNA molecule comprises the nucleotide sequence set forth in SEQ ID NO: 1.
[16] A single-stranded oligo-RNA molecule comprising (a) or (b):
  (a) a single-stranded oligo-RNA molecule comprising the nucleotide sequence set forth in SEQ ID NO: 3 in which a ribonucleotide residue at position 1 is linked to $Lx^2$, and ribonucleotide residues at positions 26 and 27 are linked via Ly;
  (b) a single-stranded oligo-RNA molecule comprising the nucleotide sequence set forth in SEQ ID NO: 6 in which a ribonucleotide residue at position 1 is linked to $Lx^2$, and ribonucleotide residues at positions 26 and 27 are linked via Ly.
[17] A kit for producing a hairpin single-stranded RNA molecule for inhibiting expression of a target gene, comprising a combination of single-stranded oligo-RNA molecules of (1) or (2):
  (1) a combination of a first single-stranded oligo-RNA molecule comprising the nucleotide sequence set forth in SEQ ID NO: 2 in which a ribonucleotide residue at position 24 is linked to $Lx^1$, and a second single-stranded oligo-RNA molecule comprising the nucleotide sequence set forth in SEQ ID NO: 3 in which a ribonucleotide residue at position 1 is linked to $Lx^2$, and ribonucleotide residues at positions 26 and 27 are linked via Ly;
  (2) a combination of a first single-stranded oligo-RNA molecule comprising the nucleotide sequence set forth in SEQ ID NO: 5 in which a ribonucleotide residue at position 22 is linked to $Lx^1$, and a second single-stranded oligo-RNA molecule comprising the nucleotide sequence set forth in SEQ ID NO: 6 in which a ribonucleotide residue at position 1 is linked to $Lx^2$, and ribonucleotide residues at positions 26 and 27 are linked via Ly.

This disclosure encompasses the contents disclosed in Japanese Patent Application No. 2018-187767 of which this disclosure claims priority.

A hairpin single-stranded RNA molecule containing an expression-inhibiting sequence for a target gene can thus be efficiently produced.

DETAILED DESCRIPTION

Hereinafter, our methods, molecules and kits will be described in detail.

Our method produces a hairpin single-stranded RNA molecule capable of inhibiting expression of a gene. The hairpin single-stranded RNA molecule produced by the method has a single-stranded structure where the 3' end of the sense strand and the 5' end of the antisense strand of a double-stranded RNA containing a gene expression-inhibiting sequence are linked via a sequence containing a non-nucleotide linker; and a ribonucleotide is further linked, via a sequence containing a non-nucleotide linker, to the 3' end of the antisense strand. The 5' end and the 3' end of the hairpin single-stranded RNA molecule produced by the method are not linked. As used herein, the "hairpin" means that a single-stranded RNA molecule is intramolecularly annealed (self-annealed) to form at least one double-stranded structure. In the hairpin single-stranded RNA molecule produced by the method, a 5'-side region containing the 5' end and a 3'-side region containing the 3' end are each individually and intramolecularly annealed to form two double-stranded structures. The "RNA," "RNA molecule," "nucleic acid molecule" and "nucleic acid" may be composed of only nucleotides or may be composed of nucleotides and non-nucleotide substances (e.g., an amino acid derivative such as a proline derivative or a glycine derivative).

Figure 1:
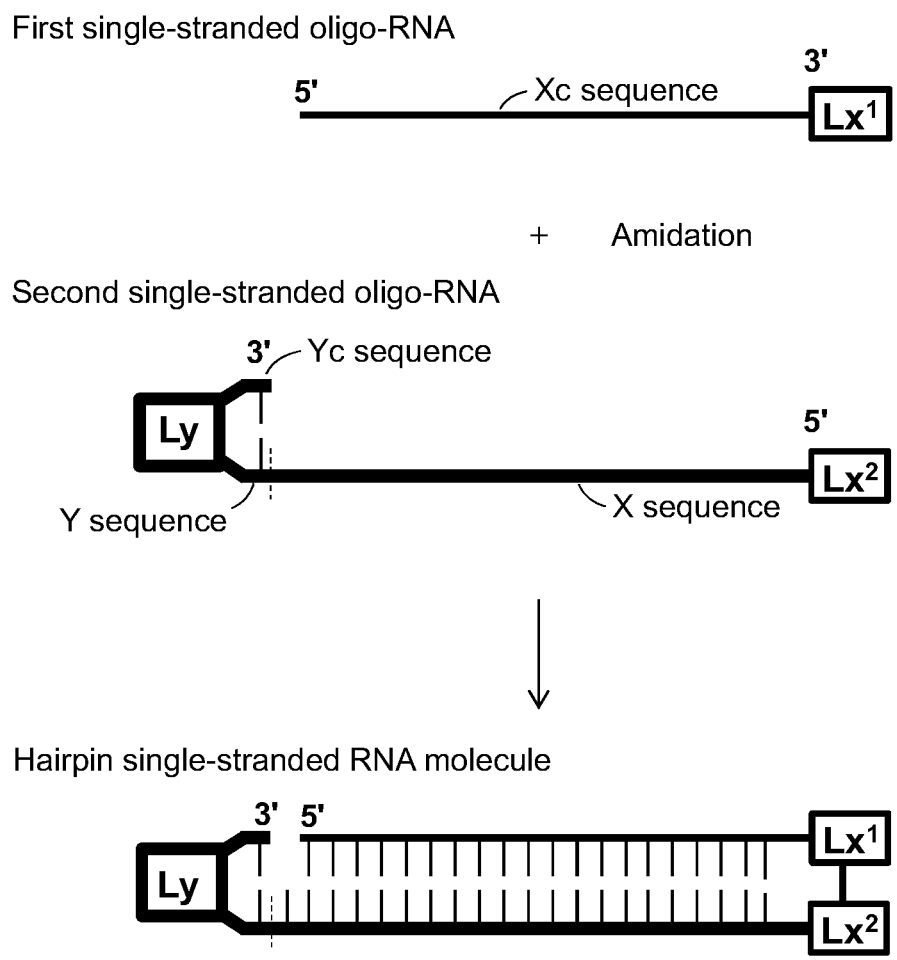
FIG. 1 is a schematic drawing illustrating our production method. Vertical lines (solid lines) on lines depicting X and Xc or Y and Yc sequences schematically represent that the sequences are complementary, although they do not definitely indicate each individual ribonucleotide residue or the complementarities of each individual ribonucleotide residue to its corresponding residue. The boundary between the sequence X and the sequence Y is schematically indicated by a vertical line (dotted line).

The hairpin single-stranded RNA molecule containing a gene expression-inhibiting sequence can be produced by separately synthesizing two fragments, i.e., (i) a first single-stranded oligo-RNA molecule having a non-nucleotide linker having an amino group ($Lx^1$) on the 3' side and (ii) a second single-stranded oligo-RNA molecule having a non-nucleotide linker having a carboxyl group ($Lx^2$) on the 5' side and containing a non-nucleotide linker (Ly) on the 3' side, and linking these fragments by amidation reaction. In this context, the carboxyl group is also referred to as a carboxylic acid group. A schematic drawing of the method is illustrated in FIG. 1. In FIG. 1, $Lx^1$ is a non-nucleotide linker having an amino group, $Lx^2$ is a non-nucleotide linker having a carboxyl group, and Ly is a non-nucleotide linker. The hairpin single-stranded RNA molecule having a relatively long chain can be produced by linking a pair of single-stranded RNA molecules having a shorter chain. This can achieve high production efficiency of the hairpin single-stranded RNA molecule.

More specifically, the method of producing a hairpin single-stranded RNA molecule containing a gene expression-inhibiting sequence comprises the step of reacting a first single-stranded oligo-RNA molecule represented by formula (I) with a second single-stranded oligo-RNA molecule represented by formula (II) in the presence of a dehydration condensation agent:

$$5'\text{-Xc-Lx}^1 \quad (I)$$

$$\text{Lx}^2\text{-X—Y-Ly-Yc-3'} \quad (II).$$

As mentioned later, in using a carbodiimide-based dehydration condensation agent as the dehydration condensation agent in the method, the carbodiimide-based dehydration condensation agent is used in combination with an N-hydroxy nitrogen-containing aromatic compound (e.g., hydroxybenzotriazole or a derivative thereof) or a cyano(hydroxyimino)acetic acid ester. In using a 2-halopyridinium-based dehydration condensation agent as the dehydration condensation agent, the 2-halopyridinium-based dehydration condensation agent is used in combination with an N-hydroxy nitrogen-containing aromatic compound. In using a formamidinium-based dehydration condensation agent as the dehydration condensation agent, the formamidinium-based dehydration condensation agent is used in combination with an N-hydroxy nitrogen-containing aromatic compound or an N-hydrocarbon-substituted imidazole derivative.

The reaction of the first single-stranded oligo-RNA molecule with the second single-stranded oligo-RNA molecule is amidation reaction. The amidation reaction (dehydration condensation reaction) of the first single-stranded oligo-RNA molecule (specifically, the amino group contained in $Lx^1$ at the end of this molecule) with the second single-stranded oligo-RNA molecule (specifically, the carboxyl group contained in $Lx^2$ at the end of this molecule) can form an amide bond between the first single-stranded oligo-RNA molecule and the second single-stranded oligo-RNA molecule. This amidation reaction in the production method can be carried out in a reaction solvent, particularly, in a mixed solvent comprising a buffer solution and a hydrophilic organic solvent.

The "oligo-RNA" and "oligo-RNA molecule" refer to an RNA molecule having a nucleotide sequence with a nucleotide length of 49 or less (the number of residues in a non-nucleotide linker is not counted). The terms "oligo-RNA" and "oligo-RNA molecule" are commonly used interchangeably with each other. The single-stranded oligo-RNA molecule is also referred to as a single-stranded oligo-RNA, an oligo nucleic acid, a single-stranded nucleic acid molecule, an oligo-RNA, or an oligo-RNA molecule.

Formula (I) represents a structure where the sequence Xc and the linker $Lx^1$ are connected in the order of Xc-$Lx^1$ from the 5'-end side. Formula (II) represents a structure where the sequences X, Y and Yc and the linkers $Lx^2$ and Ly are connected in the order of $Lx^2$-X—Y-Ly-Yc from the 5'-end side.

In formula (I) and formula (II), X, Xc, Y and Yc each is composed of a ribonucleotide residue (i.e., one or more ribonucleotide residues). The ribonucleotide residue(s) may contain any nucleotide(s) selected from adenine, uracil, guanine, and cytosine. The ribonucleotide residue(s) may also be a modified ribonucleotide residue(s) and has, for instance, a modified nucleobase(s) (modified base(s)). Examples of the modification include, but are not limited to, fluorescent dye labeling, methylation, halogenation, pseudouridilation, amination, deamination, thiolation, and dihydroxylation. X, Xc, Y and Yc, each independently, may consist of only an unmodified ribonucleotide residue(s), may contain an unmodified ribonucleotide residue(s) and a modified ribonucleotide residue(s), or may contain only a modified ribonucleotide residue(s).

Xc is complementary to X. Xc preferably consists of a sequence completely complementary (complement sequence) to the whole region or a partial region of X. When Xc is completely complementary to the whole region of X, Xc consists of a complement sequence of the whole region from the 5' end to the 3' end of X and has the same number of nucleotides as that of X. When Xc is completely complementary to a partial region of X, Xc consists of a complement sequence of the partial region of X and has the number of nucleotides smaller by 1 or more nucleotides, for instance, from 1 to 4 nucleotides or 1 or 2 nucleotides, than that of X. This partial region is preferably a region consisting of a consecutive nucleotide sequence starting from the terminal nucleotide on the $Lx^2$ side in X.

X may have a nucleotide length of, for instance, from 19 to 39 nucleotides, and has a nucleotide length of preferably from 19 to 30 nucleotides, more preferably from 19 to 25 nucleotides.

Xc may have a nucleotide length of, for instance, from 19 to 39 nucleotides, and has a nucleotide length of preferably from 19 to 30 nucleotides, more preferably from 19 to 25 nucleotides.

Yc and Y have the same nucleotide length. Yc is complementary to Y. Yc preferably consists of a sequence completely complementary (complement sequence) to the whole region of Y. When Yc is completely complementary to the whole region of Y, Yc consists of a complement sequence of the whole region from the 5' end to the 3' end of Y and has the same number of nucleotides as that of Y.

Y may have a nucleotide length of, for instance, from 1 to 5 nucleotides, and has a nucleotide length of preferably from 1 to 3 nucleotides, more preferably from 1 or 2 nucleotides.

Yc may have a nucleotide length of, for instance, from 1 to 5 nucleotides, and has a nucleotide length of preferably from 1 to 3 nucleotides, more preferably from 1 or 2 nucleotides.

The difference between the total number of nucleotides (nucleotide length) of X and Y [(X+Y)] and the total number of nucleotides (nucleotide length) of Xc and Yc [(Xc+Yc)], [(X+Y)−(Xc+Yc)], is not particularly limited and is, for instance, from 0 to 4 nucleotides (a nucleotide length of from 0 to 4 nucleotides), preferably 0, 1, or 2 nucleotides (a nucleotide length of 0, 1, or 2 nucleotides).

In the second single-stranded oligo-RNA molecule represented by formula (II), the total number of nucleotides of X, Y and Yc is, for instance, from 21 to 49 nucleotides, preferably from 21 to 30 nucleotides, more preferably from 25 to 30 nucleotides.

The linker $Lx^1$ in formula (I) is a non-nucleotide linker having an amino group, preferably a primary amino group or a secondary amino group. The amino group may be present at the end of the linker $Lx^1$ or may be inside the linker, and is preferably present at the end of the linker.

The linker $Lx^1$ is represented by, for instance, formula (III):

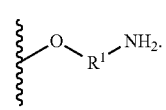

(III)

In formula (III), $R^1$ is an alkylene chain having m carbon atoms. In this context, any hydrogen atom on a carbon atom of the alkylene chain $R^1$ may be substituted by any substituent or may not be substituted. m is not particularly limited and can be appropriately set depending on the desired length of the linker $Lx^1$. For instance, from the viewpoints of production cost and yield, m is preferably an integer of from 1 to 30, more preferably an integer of from 1 to 20, further preferably an integer of from 1 to 10. —$OR^1$ in formula (III) is bonded to the 3' end of Xc via a phosphodiester bond. Specifically, —$OR^1$ in the linker $Lx^1$ is bonded to position 3' of a sugar (ribose) at the 3' end of Xc via a phosphodiester bond.

The linker $Lx^1$ preferably has a linear structure. Preferably, the linker $Lx^1$ may be represented by formula (VI):

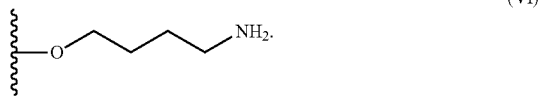

(VI)

The linker $Lx^2$ in formula (II) is a non-nucleotide linker having a carboxyl group.

The linker $Lx^2$ may have any structure as long as the linker has a carboxyl group and does not inhibit amidation reaction. The carboxyl group may be present at the end of the linker $Lx^2$ or may be inside the linker, and is preferably present at the end of the linker.

Examples of the linker $Lx^2$ include a non-nucleotide linker having an amino acid backbone. Such linker $Lx^2$ may be a linker that is derived from an amino acid and has a structure having a carboxyl group at the end.

The "amino acid backbone" refers to any organic compound containing at least one amino group and at least one carboxyl group in the molecule, or a structure thereof. In this context, the amino group refers to a functional group generated by removal of one or more hydrogen atoms from ammonia, primary amine, or secondary amine. The amino group and/or the carboxyl group constituting the amino acid backbone may form any chemical bond such as an amide bond or an ester bond. The amino acid from which the amino acid backbone is derived may be, for instance, a natural amino acid, or may be an artificial amino acid. The natural amino acid refers to an amino acid having a naturally occurring structure or an optical isomer thereof. The artificial amino acid refers to an amino acid having a non-naturally occurring structure. Specifically, the artificial amino acid refers to an amino acid, i.e., a carboxylic acid derivative containing an amino group (an organic compound containing at least one amino group and at least one carboxyl group in the molecule) having a non-naturally occurring structure. The artificial amino acid is preferably free from, for instance, a hetero ring. The amino acid may be, for instance, glycine, α-alanine, arginine, asparagine, aspartic acid, cysteine, cystine, glutamine, glutamic acid, histidine, isoleucine, leucine, lysine, hydroxylysine, methionine, phenylalanine, serine, threonine, tyrosine, valine, proline, 4-hydroxyproline, tryptophan, β-alanine, 1-amino-2-carboxycyclopentane, aminobenzoic acid, aminopyridinecarboxylic acid, nipecotic acid, isonipecotic acid, pipecolic acid, 3-pyrrolidinecarboxylic acid, γ-aminobutyric acid, or sarcosine, and may or may not further have a substituent or a protecting group. Examples of the substituent include, but are not limited to, halogen, hydroxy, alkoxy, amino, carboxy, sulfo, nitro, carbamoyl, sulfamoyl, alkyl, alkenyl, alkynyl, haloalkyl, aryl, arylalkyl, alkylaryl, cycloalkyl, cycloalkenyl, cycloalkylalkyl, cyclylalkyl, hydroxyalkyl, alkoxyalkyl, aminoalkyl, silyl, silyloxyalkyl, pyrrolyl, and imidazolyl. The protecting group may be, for instance, a functional group that converts a highly reactive functional group to an inactive one. Examples thereof include known protecting groups. For instance, the disclosure of Protective Groups in Organic Synthesis, 4th edition, Greene et al., 2007, John Wiley & Sons, Inc. may be incorporated for the protecting group. Examples of the protecting group include, but are not limited to, a tert-butyldimethylsilyl group, a bis(2-acetoxyethyloxy)methyl group, a triisopropylsilyloxymethyl group, a 1-(2-cyanoethoxy)ethyl group, a 2-cyanoethoxymethyl group, a 2-cyanoethyl group, a tolylsulfonylethoxymethyl group, a trityl group and a dimethoxytrityl group. When isomers such as optical isomers, geometric isomers, or stereoisomers of the amino acid are present, any of these isomers may be used. These isomers may be single isomers or may be mixtures.

Preferred examples of the linker $Lx^2$ include a non-nucleotide linker comprising at least one of a pyrrolidine backbone or a piperidine backbone and having a carboxyl group, and a non-nucleotide linker comprising —$NHCH_2COOH$. In one example, the linker $Lx^2$ is represented by, for instance, formula (IV) or formula (IV'), more preferably represented by formula (IV):

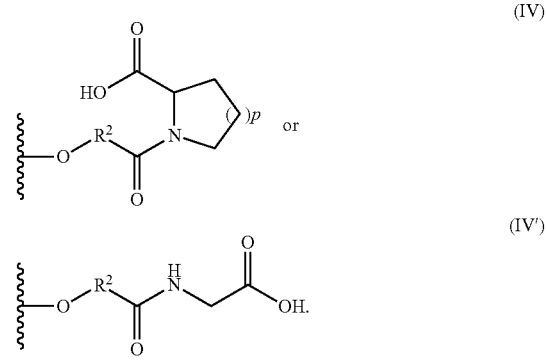

In formula (IV) and formula (IV'), $R^1$ is an alkylene chain having n carbon atoms. In this context, any hydrogen atom on a carbon atom of the alkylene chain $R^2$ may be substituted by any substituent or may not be substituted. n is not particularly limited and can be appropriately set depending on the desired length of the linker $Lx^2$. For instance, from the viewpoints of production cost and yield, n is preferably an integer of from 1 to 30, more preferably an integer of from 1 to 20, further preferably an integer of from 1 to 10.

In formula (IV), p is 1 or 2, preferably 1.

—$OR^2$ in formula (IV) and formula (IV') is bonded to the 5' end of X via a phosphodiester bond. Specifically, —$OR^2$ in the linker $Lx^2$ is bonded to position 5' of a sugar (ribose) at the 5' end of X via a phosphodiester bond.

In this context, the total of m for $R^1$ and n for $R^2$ is, for instance, an integer of from 2 to 31, preferably an integer of from 2 to 21, more preferably an integer of from 2 to 15.

In formula (IV), the linker $Lx^2$ has a cyclic structure such as a pyrrolidine backbone or a piperidine backbone.

Preferably, the linker Lx² may be represented by formula (VII):

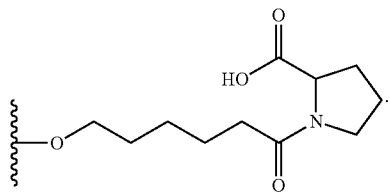
(VII)

The linker represented by formula (VII) may be an optically active substance represented by formula (VII-1) or formula (VII-2):

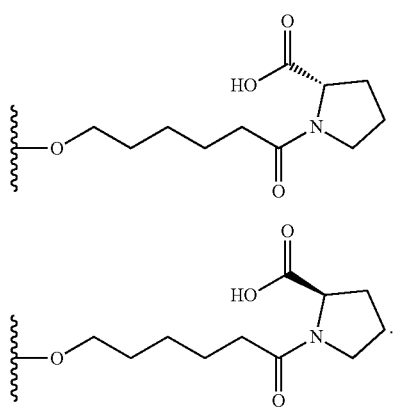
(VII-1)

(VII-2)

In another example, the linker Lx² may be represented by formula (VII'):

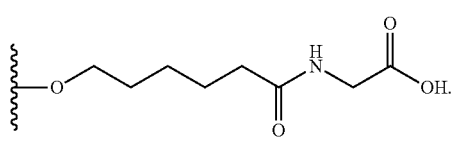
(VII')

The linker Ly in formula (II) is a non-nucleotide linker. The linker Ly may have any structure as long as the linker does not inhibit amidation reaction. Examples of the linker Ly include a non-nucleotide linker having an amino acid backbone or an amino alcohol backbone. Such linker Ly may be a linker having a structure derived from an amino acid. This "amino acid backbone" is as mentioned above. However, the amino group and/or the carboxyl group constituting the amino acid backbone of the linker Ly may form any chemical bond such as an amide bond or an ester bond.

The "amino alcohol backbone" refers to any organic compound containing at least one amino group and at least one hydroxyl group in the molecule, or a structure thereof. The "amino group" is as mentioned above. The amino group and/or the hydroxyl group constituting the amino alcohol backbone of the linker Ly may form any chemical bond such as an amide bond, an ester bond, or an ether bond. Examples of the amino alcohol include amino alcohols obtained by converting the carboxyl group of the amino acid described above. The amino alcohol may be, for instance, aminoethanol, aminopropanol, valinol, prolinol, or piperidinemethanol, and may or may not further have a substituent or a protecting group. Examples of the substituent include, but are not limited to, halogen, hydroxy, alkoxy, amino, carboxy, sulfo, nitro, carbamoyl, sulfamoyl, alkyl, alkenyl, alkynyl, haloalkyl, aryl, arylalkyl, alkylaryl, cycloalkyl, cycloalkenyl, cycloalkylalkyl, cyclylalkyl, hydroxyalkyl, alkoxyalkyl, aminoalkyl, silyl, silyloxyalkyl, pyrrolyl, and imidazolyl. The protecting group may be, for instance, a functional group that converts a highly reactive functional group to an inactive one. Examples thereof include known protecting groups. For instance, the disclosure of Protective Groups in Organic Synthesis, 4th edition, Greene et al., 2007, John Wiley & Sons, Inc. may be incorporated for the protecting group. Examples of the protecting group include, but are not limited to, a tert-butyldimethylsilyl group, a bis(2-acetoxyethyloxy)methyl group, a triisopropylsilyloxymethyl group, a 1-(2-cyanoethoxy)ethyl group, a 2-cyanoethoxymethyl group, a 2-cyanoethyl group, a tolylsulfonylethoxymethyl group, a trityl group and a dimethoxytrityl group. When isomers such as optical isomers, geometric isomers, or stereoisomers of the amino alcohol are present, any of these isomers may be used. These isomers may be single isomers or may be mixtures.

The linker Ly is preferably a non-nucleotide linker comprising at least one of a pyrrolidine backbone or a piperidine backbone, or a non-nucleotide linker comprising —NHCH₂COO—. The linker Ly more preferably has a cyclic structure that may be substituted at two or more positions. The linker Ly may have one or two or more n-membered rings (e.g., n=5 or 6). In having two or more rings, these rings may form a condensed ring, a spiro ring, a bicyclo ring or the like. The linker Ly may have one or two or more substituents. The linker Ly links Y and Yc described above via its any two groups (e.g., substituents on two atoms constituting a n-membered ring). The hairpin single-stranded RNA molecule produced by our method excels in nuclease resistance because the sense strand and the antisense strand thereof are linked by such a linker.

In one example, the linker Ly is a non-nucleotide linker comprising at least one of a pyrrolidine backbone or a piperidine backbone, preferably a non-nucleotide linker comprising a pyrrolidine backbone or a piperidine backbone. The pyrrolidine backbone may be, for instance, a pyrrolidine derivative backbone in which at least one carbon atom constituting the 5-membered pyrrolidine ring is replaced. If replaced, for instance, the carbon atom(s) other than the carbon atom at position 2 (C-2) is preferably replaced. The carbon atom(s) may be replaced by, for instance, a nitrogen atom(s), an oxygen atom(s), or a sulfur atom(s). The pyrrolidine backbone may contain, for instance, a carbon-carbon double bond or a carbon-nitrogen double bond in the 5-membered pyrrolidine ring. In the pyrrolidine backbone, for instance, a hydrogen atom(s) or a substituent(s) as mentioned later may be attached to the carbon atom(s) and the nitrogen atom constituting the 5-membered pyrrolidine ring. The linker Ly may link Y and Yc via, for instance, any of groups in the pyrrolidine backbone. They may be linked via any one of the carbon atoms and the nitrogen atom in the 5-membered ring, preferably via the carbon atom at position 2 (C-2) and the nitrogen atom in the 5-membered ring. Examples of the pyrrolidine backbone include a proline backbone and a prolinol backbone.

In one example, in formula (I) and formula (II), Ly is a non-nucleotide linker comprising a pyrrolidine backbone or a piperidine backbone, Lx¹ is a non-nucleotide linker having an amino group, and $Lx^2$ is a non-nucleotide linker comprising at least one of a pyrrolidine backbone or a piperidine backbone and having a carboxyl group.

The piperidine backbone may be, for instance, a piperidine derivative backbone in which at least one carbon constituting the 6-membered piperidine ring is replaced. If replaced, for instance, the carbon atom(s) other than the carbon atom at position 2 (C-2) is preferably replaced. The carbon atom(s) may be replaced by, for instance, a nitrogen atom(s), an oxygen atom(s), or a sulfur atom(s). The piperidine backbone may contain, for instance, a carbon-carbon double bond or a carbon-nitrogen double bond in the 6-membered piperidine ring. In the piperidine backbone, for instance, a hydrogen atom(s) or a substituent(s) as mentioned later may be attached to the carbon atom(s) and the nitrogen atom constituting the 6-membered piperidine ring. The linker Ly may link Y and Yc via, for instance, any of groups in the piperidine backbone. They may be linked via any one of the carbon atoms and the nitrogen atom in the 6-membered ring, preferably via the carbon atom at position 2 (C-2) and the nitrogen atom in the 6-membered ring.

The linker Ly is represented by, for instance, formula (VIII):

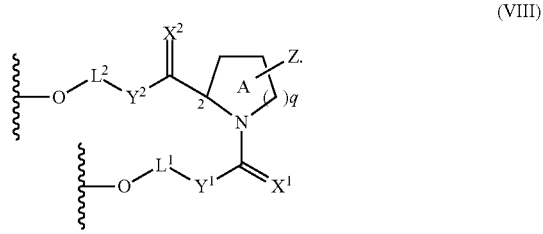

(VIII)

In formula (VIII), $X^1$ and $X^2$ are each independently $H_2$, O, S, or NH;

$Y^1$ and $Y^2$ are each independently a single bond, $CH_2$, NH, O, or S;

Z is a hydrogen atom or a substituent bonded to C-3, C-4, C-5, or C-6 on ring A;

$L^1$ is an alkylene chain having r carbon atoms where a hydrogen atom on any carbon atom of the alkylene chain is optionally unsubstituted or substituted by OH, $OR^a$, $NH_2$, $NHR^a$, $NR^aR^b$, SH, or $SR^a$ or $L^1$ is a polyether chain in which at least one carbon atom of the alkylene chain is replaced by an oxygen atom, where when $Y^1$ is NH, O, or S, an $L^1$ atom bonded to $Y^1$ is carbon and an $L^1$ atom bonded to O is carbon while oxygen atoms are not next to each other;

$L^2$ is an alkylene chain having s carbon atoms where a hydrogen atom on any alkylene carbon atom is optionally unsubstituted or substituted by OH, $OR^a$, $NH_2$, $NHR^a$, $NR^aR^b$, SH, or $SR^a$ or $L^2$ is a polyether chain in which at least one carbon atom of the alkylene chain is replaced by an oxygen atom, where when $Y^2$ is NH, O, or S, an $L^2$ atom bonded to $Y^2$ is carbon and an $L^2$ atom bonded to $OR^2$ is carbon while oxygen atoms are not next to each other;

$R^a$ and $R^b$ are each independently a substituent or a protecting group;

q is 1 or 2;

r is an integer of from 0 to 30;

s is an integer of from 0 to 30;

one carbon atom other than C-2 on ring A is optionally replaced by a nitrogen atom, an oxygen atom, or a sulfur atom, and ring A optionally contains a carbon-carbon double bond or a carbon-nitrogen double bond.

Y and Yc are linked to the linker Ly via $—OL^1$ or $—OL^2$ in formula (VIII). In one example, Y may be linked via $—OL^1$ and Yc may be linked via $—OL^2$, to the linker Ly. In another example, Y may be linked via $—OL^2$ and Yc may be linked via $—OL^1$, to the linker Ly.

In formula (VIII), $X^1$ and $X^2$ are each independently, for instance, $H_2$, O, S, or NH. That $X^1$ is $H_2$ in formula (VIII) means that $X^1$ and a carbon atom bonded to $X^1$ together form $CH_2$. The same applies to $X^2$.

In formula (VIII), $Y^1$ and $Y^2$ are each independently a single bond, $CH_2$, NH, O, or S.

In ring A of formula (VIII), q is 1 or 2. When q is 1, ring A is a 5-membered ring, for instance, the pyrrolidine backbone. Examples of the pyrrolidine backbone include a proline backbone and a prolinol backbone, and the pyrrolidine backbone can be exemplified by a divalent structure thereof. When q is 2, ring A is a 6-membered ring, for instance, the piperidine backbone. In Ring A, one carbon atom other than C-2 on ring A may be replaced by a nitrogen atom, an oxygen atom, or a sulfur atom. In addition, ring A optionally contains a carbon-carbon double bond or a carbon-nitrogen double bond in ring A. For instance, ring A may be either L-form or D-form.

In formula (VIII), Z is a hydrogen atom or a substituent bonded to C-3, C-4, C-5, or C-6 on ring A. When Z is a substituent, the number of substituents Z may be 1 or more or not present. A plurality of substituents Z may be the same or different from each other.

The substituent Z is, for instance, halogen, OH, $OR^a$, $NH_2$, $NHR^a$, $NR^aR^b$, SH, $SR^a$ or an oxo group (=O).

$R^a$ and $R^b$ are each independently, for instance, a substituent or a protecting group and may be the same or different. Examples of the substituent include halogen, alkyl, alkenyl, alkynyl, haloalkyl, aryl, heteroaryl, arylalkyl, cycloalkyl, cycloalkenyl, cycloalkylalkyl, cyclylalkyl, hydroxyalkyl, alkoxyalkyl, aminoalkyl, heterocyclylalkenyl, heterocyclylalkyl, heteroarylalkyl, silyl, and silyloxyalkyl. The same applies to the following descriptions. The substituent Z may be each substituent listed above.

The protecting group is, for instance, a functional group that converts a highly reactive functional group to an inactive one. Examples thereof include known protecting groups. For instance, the disclosure of Protective Groups in Organic Synthesis, 4th edition, Greene et al., 2007, John Wiley & Sons, Inc. may be incorporated for the protecting group. Examples of the protecting group include, but are not limited to, a tert-butyldimethylsilyl group (hereinafter, a TBDMS group), a bis(2-acetoxyethyloxy)methyl group (hereinafter, an ACE group), a triisopropylsilyloxymethyl group (hereinafter, a TOM group), a 1-(2-cyanoethoxy)ethyl group (hereinafter, a CEE group), a 2-cyanoethoxymethyl group (hereinafter, a CEM group), a 2-cyanoethyl group (hereinafter, a CE group), a tolylsulfonylethoxymethyl group (hereinafter, a TEM group), a trityl group (hereinafter, a Tr group), and a dimethoxytrityl group (hereinafter, a DMTr group). When Z is $OR^a$, examples of the protecting group include a TBDMS group, an ACE group, a TOM group, a CEE group, a CEM group, and a TEM group. Other examples thereof include a silyl-containing group. The same applies to the following descriptions.

In formula (VIII), $L^1$ is an alkylene chain having r carbon atoms. A hydrogen atom on any carbon atom of the alkylene may be substituted or unsubstituted by, for instance, OH, $OR^a$, $NH_2$, $NHR^a$, $NR^aR^b$, SH, or $SR^a$. Alternatively, $L^1$ may be a polyether chain in which at least one carbon atom of the alkylene chain is replaced by an oxygen atom. The polyether chain is, for instance, polyethylene glycol. When $Y^1$ is NH, O, or S, an $L^1$ atom bonded to $Y^1$ is carbon and an $L^1$ atom bonded to O is carbon while oxygen atoms are not next to each other.

In formula (VIII), $L^2$ is an alkylene chain having s carbon atoms. A hydrogen atom on any carbon atom of the alkylene chain may be substituted or unsubstituted by, for instance, OH, $OR^a$, $NH_2$, $NHR^a$, $NR^aR^b$, SH, or $SR^a$. Alternatively, $L^2$ may be a polyether chain in which at least one carbon atom of the alkylene chain is replaced by an oxygen atom. When $Y^2$ is NH, O, or S, an $L^2$ atom bonded to $Y^2$ is carbon and an $L^2$ atom bonded to O is carbon while oxygen atoms are not next to each other.

r for $L^1$ and s for $L^2$ are not particularly limited and the lower limit of each is, for instance, 0 and the upper limit of each is also not particularly limited. r and s can be appropriately set depending on, for instance, the desired length of the linker Ly. From the viewpoints of production cost and yield, for instance, r and s are each preferably an integer of from 0 to 30, more preferably an integer of from 0 to 20, further preferably an integer of from 0 to 15. In this context, r and s may be the same or different.

$R^a$ and $R^b$ are as defined above.

In formula (VIII), hydrogen atoms may be, for instance, each independently substituted by halogen such as Cl, Br, F, and I.

Preferably, the linker Ly may be represented by any of formulas (VIII-1) to (VIII-9). In formulas (VIII-1) to (VIII-9), t is an integer of from 0 to 10, and r and s are the same as in formula (VIII). Specifically, for instance, in formula (VIII-1), r=8; in formula (VIII-2), r=3; in formula (VIII-3), r=4 or 8; in formula (VIII-4), r=7 or 8; in formula (VIII-5), r=3 and s=4; in formula (VIII-6), r=8 and s=4; in formula (VIII-7), r=8 and s=4; in formula (VIII-8), r=5 and s=4; and in formula (VIII-9), t=1 and s=4:

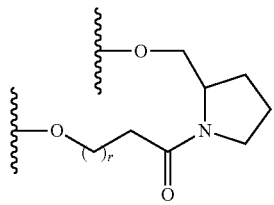

(VIII-1)

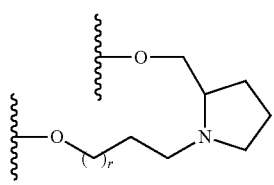

(VIII-2)

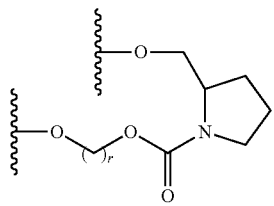

(VIII-3)

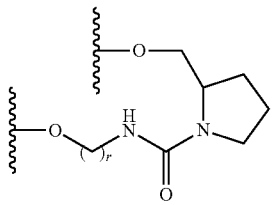

(VIII-4)

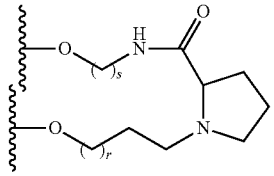

(VIII-15)

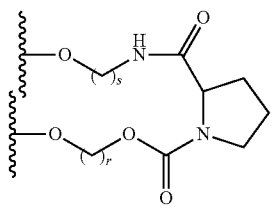

(VIII-6)

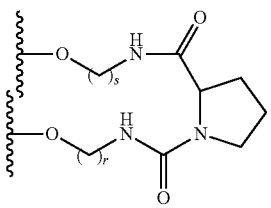

(VIII-7)

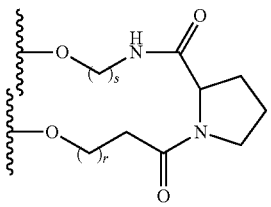

(VIII-8)

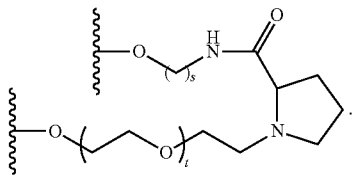

(VIII-9)

In one example, the linker Ly may be represented by formula (V) or formula (IX):

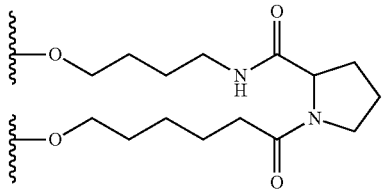

(V)

-continued (IX)
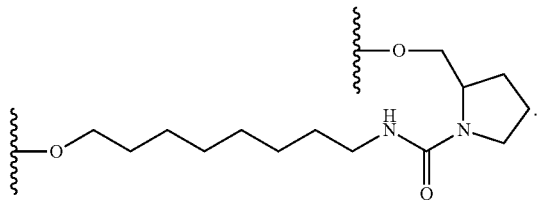

The linker represented by formula (V) may be an optically active substance represented by formula (V-1) or formula (V-2):

(V-1)
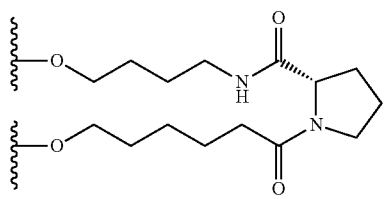

(V-2)
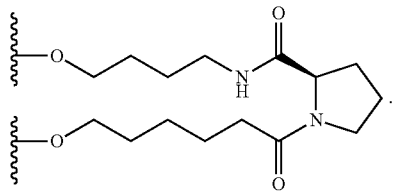

In another example, the linker Ly is a non-nucleotide linker comprising —NHCH$_2$COO—, and such a linker is represented by, for instance, formula (XXI). This linker Ly corresponds basically to the linker Ly represented by formula (VIII), and the description about the linker represented by formula (VIII) is thus applied to the linker represented by formula (XXI):

(XXI)
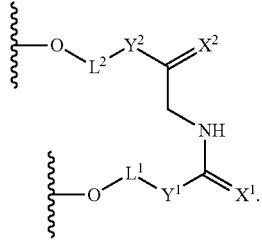

In formula (XXI), $X^1$ and $X^2$ are each independently H$_2$, O, S, or NH;

$Y^1$ and $Y^2$ are each independently a single bond, CH$_2$, NH, O, or S;

$L^1$ is an alkylene chain having r carbon atoms where a hydrogen atom on any carbon atom of the alkylene chain is optionally unsubstituted or substituted by OH, OR$^a$, NH$_2$, NHR$^a$, NR$^a$R$^b$, SH, or SR$^a$ or $L^1$ is a polyether chain in which at least one carbon atom of the alkylene chain is replaced by an oxygen atom, where when $Y^1$ is NH, O, or S, an $L^1$ atom bonded to $Y^1$ is carbon and an $L^1$ atom bonded to O is carbon while oxygen atoms are not next to each other;

$L^2$ is an alkylene chain having s carbon atoms where a hydrogen atom on any alkylene carbon atom is optionally unsubstituted or substituted by OH, OR$^a$, NH$_2$, NHR$^a$, NR$^a$R$^b$, SH, or SR$^a$ or $L^2$ is a polyether chain in which at least one carbon atom of the alkylene chain is replaced by an oxygen atom, where when $Y^2$ is NH, O, or S, an $L^2$ atom bonded to $Y^2$ is carbon and an $L^2$ atom bonded to OR$^2$ is carbon while oxygen atoms are not next to each other;

R$^a$ and R$^b$ are each independently a substituent or a protecting group;

r is an integer of from 0 to 30; and s is an integer of from 0 to 30.

Y and Ye are linked to the linker Ly via —OL$^1$ or —OL$^2$ in formula (XXI). In one example, Y may be linked via —OL$^1$ and Ye may be linked via —OL$^2$, to the linker Ly. In another example, Y may be linked via —OL$^2$ and Ye may be linked via —OL$^1$, to the linker Ly.

In formula (XXI), $X^1$ and $X^2$ are each independently, for instance, H$_2$, O, S, or NH. That $X^1$ is H$_2$ in formula (XXI) means that $X^1$ and a carbon atom bonded to $X^1$ together form CH$_2$. The same applies to $X^2$.

In formula (XXI), $Y^1$ and $Y^2$ are each independently a single bond, CH$_2$, NH, O, or S.

R$^a$ and R$^b$ are each independently, for instance, a substituent or a protecting group and may be the same or different. Examples of the substituent include halogen, alkyl, alkenyl, alkynyl, haloalkyl, aryl, heteroaryl, arylalkyl, cycloalkyl, cycloalkenyl, cycloalkylalkyl, cyclylalkyl, hydroxyalkyl, alkoxyalkyl, aminoalkyl, heterocyclylalkenyl, heterocyclylalkyl, heteroarylalkyl, silyl, and silyloxyalkyl. The same applies to the following descriptions.

The protecting group is, for instance, a functional group that converts a highly reactive functional group to an inactive one. Examples thereof include known protecting groups. For instance, the disclosure of Protective Groups in Organic Synthesis, 4th edition, Greene et al., 2007, John Wiley & Sons, Inc. may be incorporated for the protecting group. Examples of the protecting group include, but are not particularly limited to, a TBDMS group, an ACE group, a TOM group, a CEE group, a CEM group, a CE group, a TEM group, a Tr group, and a DMTr group. The same applies to the following descriptions.

In formula (XXI), $L^1$ is an alkylene chain having r carbon atoms. A hydrogen atom on any carbon atom of the alkylene chain may be substituted or unsubstituted by, for instance, OH, OR$^a$, NH$_2$, NHR$^a$ NR$^a$R$^b$, SH, or SR$^a$. Alternatively, L$^1$ may be a polyether chain in which at least one carbon atom of the alkylene chain is replaced by an oxygen atom. The polyether chain is, for instance, polyethylene glycol. When $Y^1$ is NH, O, or S, an $L^1$ atom bonded to $Y^1$ is carbon and an $L^1$ atom bonded to O is carbon while oxygen atoms are not next to each other.

In formula (XXI), L$^2$ is an alkylene chain having s carbon atoms. A hydrogen atom on any carbon atom of the alkylene chain may be substituted or unsubstituted by, for instance, OH, OR$^a$, NH$_2$, NHR$^a$, NR$^a$R$^b$, SH, or SR$^a$. Alternatively, L$^2$ may be a polyether chain in which at least one carbon atom of the alkylene chain is replaced by an oxygen atom. When $Y^2$ is NH, O, or S, an $L^2$ atom bonded to $Y^2$ is carbon and an $L^2$ atom bonded to O is carbon while oxygen atoms are not next to each other.

r for L$^1$ and s for L$^2$ are not particularly limited and the lower limit of each is, for instance, 0 and the upper limit of each is also not particularly limited. r and s can be appropriately set depending on, for instance, the desired length of the linker Ly. From the viewpoints of production cost and yield, for instance, r and s are each preferably an integer of 0 to 30, more preferably an integer of 0 to 20, further preferably an integer of 0 to 15. In this context, r and s may be the same or different.

$R^a$ and $R^b$ are as defined above.

In formula (XXI), hydrogen atoms may be, for instance, each independently substituted by halogen such as Cl, Br, F, and I.

Preferably, the linker Ly may be represented by formula (XXII):

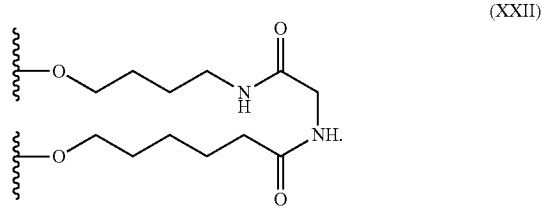 [SMILES: *OCCCCCC(=O)NCC(=O)NCCCCO*]

(XXII)

The first and second single-stranded oligo-RNA molecules can be produced using an RNA synthesis process known to those skilled in the art. Examples of the known RNA synthesis process include phosphoramidite chemistry or H-phosphonate chemistry. In phosphoramidite chemistry, a ribonucleoside bound to a hydrophobic group of a carrier is extended by condensation reaction with an RNA amidite (ribonucleoside phosphoramidite) and undergoes oxidation and deprotection, and this condensation reaction with an RNA amidite can be repeated to carry out RNA synthesis.

The first single-stranded oligo-RNA molecule represented by formula (I) can be produced by conventional RNA synthesis methods, for instance, phosphoramidite chemistry. In one example, Xc can be produced by solid-phase synthesis from the 3'-end side according to conventional methods using a solid-phase carrier bound in advance to an amino alcohol (e.g., 3'-PT Amino-Modifier C4 CPG mentioned later; Link Technologies Ltd.) corresponding to the structure of linker $Lx^1$ via the amino group. For the synthesis, any RNA amidite can be used, and general-purpose RNA amidite having any of various protecting groups such as a TBDMS group, a TOM group, an ACE group, a CEE group, a CEM group, a TEM group, and a DMTr group in the position-2' hydroxyl group may be used, for instance. In addition, any solid-phase carrier may be used, including a polystyrene-based carrier, an acrylamide-based carrier, or a glass carrier. The carrier may be in any form such as beads, a plate, a chip, or a tube. Examples of the carrier bound to the amino alcohol include, but are not limited to, 3'-PT Amino-Modifier C3 CPG and C7 CPG (Link Technologies Ltd.).

Likewise, the second single-stranded oligo-RNA molecule represented by formula (II) can be produced by conventional RNA synthesis methods, for instance, phosphoramidite chemistry. In one example, Yc is produced on a solid-phase carrier by solid-phase synthesis from the 3'-end side according to conventional methods. Then, linker Ly is linked to the 5' end of Yc. Next, solid-phase synthesis is further carried out from the end thereof, and linker $Lx^2$ can be linked to the 5' end of X to produce the second single-stranded oligo-RNA molecule. For the synthesis, any RNA amidite can be used, and general-purpose RNA amidite having any of various protecting groups such as a TBDMS group, a TOM group, an ACE group, a CEE group, a CEM group, a TEM group, and a DMTr group in the position-2' hydroxyl group may be used, for instance. In addition, any solid-phase carrier may be used, including a polystyrene-based carrier, an acrylamide-based carrier, or a glass carrier. The carrier may be in any form such as beads, a plate, a chip, or a tube. Examples of the carrier include, but are not limited to, NittoPhase® HL rG(ibu) and rU (KINOVATE).

For linking linker $Lx^2$ to the 5' end of X, any monomer for RNA synthesis suitable therefor can be used. For instance, a monomer for RNA synthesis represented by formula (X) given below can be used. This monomer corresponds basically to the linker represented by formula (IV), and the description about the linker represented by formula (IV) is thus applied to the monomer represented by formula (X). The monomer represented by formula (X) can be used as, for instance, amidite for automated nucleic acid synthesis, and is, for instance, applicable to a common automated nucleic acid synthesizer. We also provide a monomer for RNA synthesis (amidite) represented by formula (X):

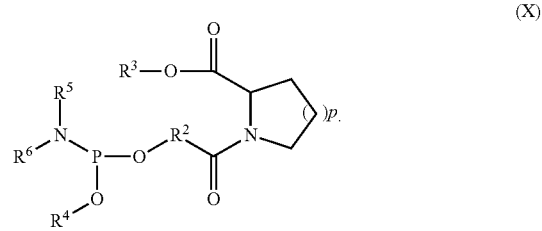

(X)

In formula (X), the description of formula (IV) can be cited for the same sites as in above formula (IV). Specifically, in formula (X), $R^2$ is an alkylene chain having n carbon atoms. In this context, any hydrogen atom on a carbon atom of the alkylene chain $R^2$ may be substituted by any substituent or may not be substituted. n is not particularly limited and can be appropriately set depending on the desired length of the linker $Lx^2$. For instance, from the viewpoints of production cost and yield, n is preferably an integer of 1 to 30, more preferably an integer of 1 to 20, further preferably an integer of 1 to 15. In formula (X), p is 1 or 2, preferably 1. In formula (X), $R^3$ is a carboxylic acid-protecting group. For instance, the disclosure of Protective Groups in Organic Synthesis, 4th edition, Greene et al., 2007, John Wiley & Sons, Inc. may be incorporated for the carboxylic acid-protecting group. Specific examples of the carboxylic acid-protecting group include a DMTr group, a Tr group, a TBDMS group, an ACE group, a TOM group, a CEE group, a CEM group, a CE group, a TEM group and a 2,4-dimethoxybenzyl group. A CE group or a 2,4-dimethoxybenzyl group is preferred.

$R^4$ is an alkyl group substituted by an electron-withdrawing group. Specific examples thereof include a 2-cyanoethyl group (a CE group) and a nitrophenylethyl group. A 2-cyanoethyl group (a CE group) is preferred.

$R^5$ and $R^6$ are each independently an alkyl group and may be the same or different. Specific examples of —$NR^5R^6$ include a diisopropylamino group, a diethylamino group, and an ethylmethylamino group. A diisopropylamino group is preferred.

Preferably, the monomer represented by formula (X) may be represented by formula (XI) or formula (XVIII).

(XI)
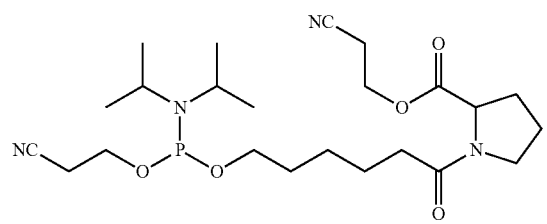

(XVIII)
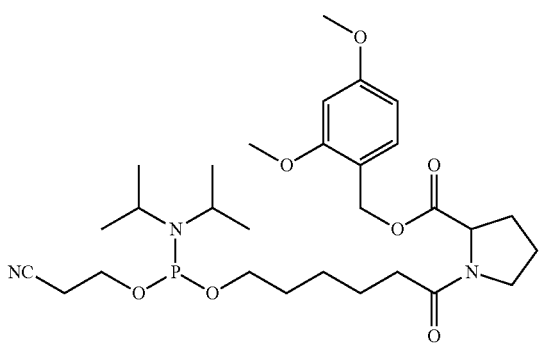

The monomer represented by formula (XI) may be an optically active substance represented by formula (XI-1) or formula (XI-2):

(XI-1)
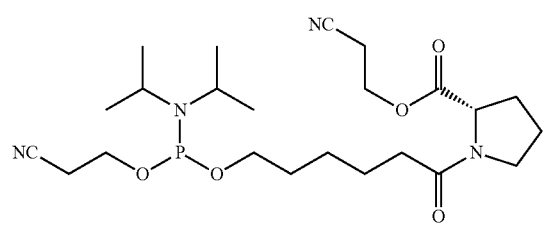

(XI-2)
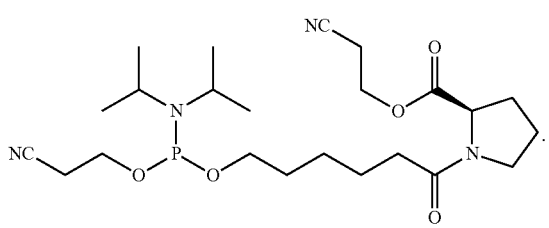

The monomer represented by formula (XVIII) may be an optically active substance represented by formula (XVIII-1) or formula (XVIII-2):

(XVIII-1)
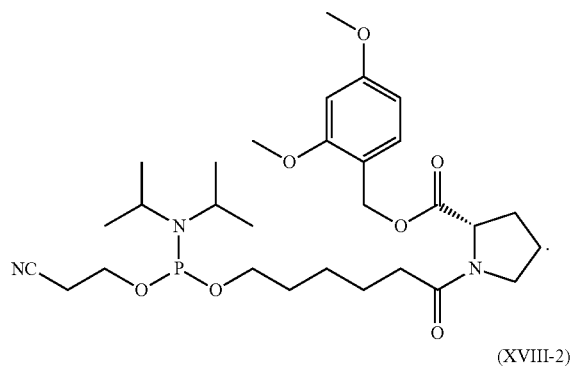

(XVIII-2)
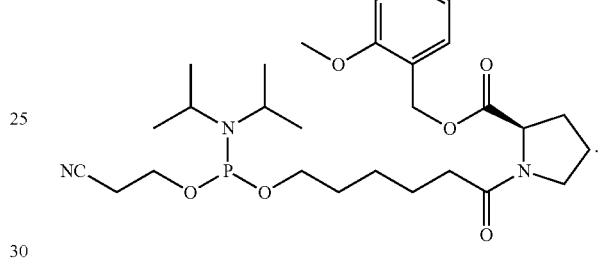

Hereinafter, an exemplary synthesis process of the monomer represented by formula (X) will be described. Starting materials and reagents which is used for synthesis may directly adopt commercially available products or may be synthesized by known methods.

The monomer represented by formula (X) can be synthesized, for instance, as shown in scheme 1, by the phosphorylation reaction of an alcohol derivative represented by formula (XII) with a phosphorylation reagent represented by formula (XIII):

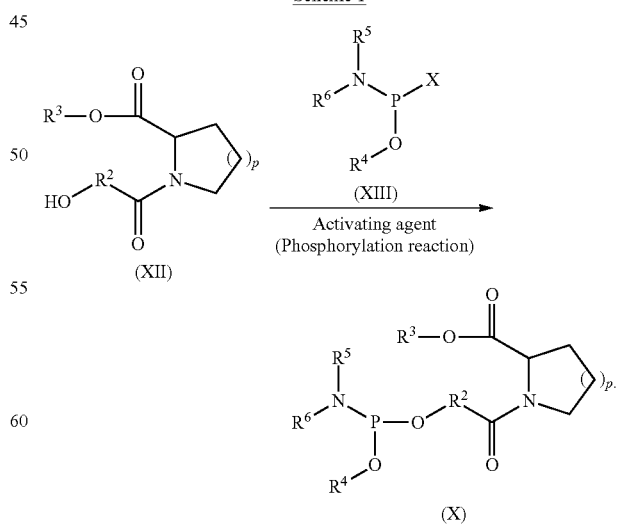

In formulae, X is halogen or $NR^5R^6$, and $R^2$, $R^3$, $R^4$, $R^5$, $R^6$, and p are as defined above.

Specific examples of the phosphorylation reagent represented by formula (XIII) include 2-cyanoethyl-N,N-diisopropylchlorophosphoramidite, nitrophenylethyl-N,N-diisopropylchlorophosphoramidite, methyl-N,N-diisopropylchlorophosphoramidite and 2-cyanoethyl-N,N,N',N'-tetraisopropylphosphorodiamidite.

The equivalent amount of the phosphorylation reagent represented by formula (XIII) is preferably 1 to 10 equivalents, more preferably 1.1 to 1.5 equivalents, with respect to the alcohol derivative represented by formula (XII).

Examples of the activating agent which is used for the phosphorylation reaction include tetrazole and diisopropylamine tetrazole salt. Diisopropylamine tetrazole salt is preferred.

The equivalent amount of the activating agent is preferably 1 to 10 equivalents, more preferably from 1.1 to 1.5 equivalents, with respect to the alcohol derivative represented by formula (XII).

Examples of the solvent which is used for the phosphorylation reaction include tetrahydrofuran, dichloromethane, chloroform, diethyl ether and acetonitrile, and acetonitrile is preferred.

The reaction temperature of the phosphorylation reaction is preferably 20 to 50° C., more preferably 20 to 30° C. The reaction time of the phosphorylation reaction is preferably 1 to 48 hours, more preferably 2 to 5 hours.

The alcohol derivative represented by formula (XII) can be synthesized, for instance, as shown in scheme 2, by the condensation reaction of an amine derivative represented by formula (XIV) with a carboxylic acid derivative represented by formula (XV):

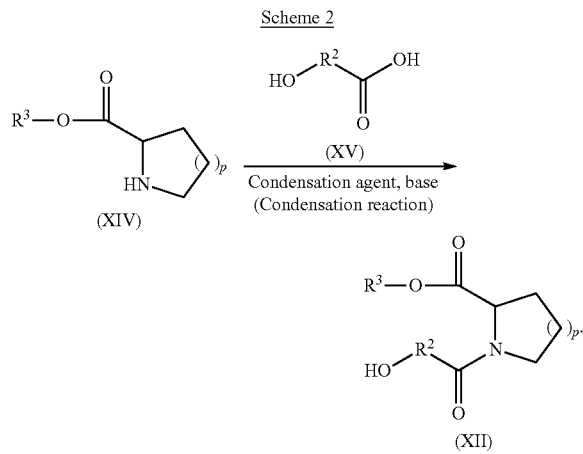

In the formulae, $R^2$, $R^3$, and p are as defined above.

The equivalent amount of the carboxylic acid derivative represented by formula (XV) which is used for the condensation reaction is preferably 1 to 3 equivalents, more preferably 1.1 to 1.5 equivalents, with respect to the amine derivative represented by formula (XIV).

Examples of the condensation agent which is used for the condensation reaction include cyclohexylcarbodiimide, N-(3'-dimethylaminopropyl)-N'-ethylcarbodiimide hydrochloride, benzotriazol-1-yloxy-trisdimethylaminophosphonium salt, O-(benzotriazol-1-yl)-N,N,N',N'-tetramethyluronium hexafluorophosphate and O-(7-azabenzotriazol-1-yl)-N,N,N',N'-tetramethyluronium hexafluorophosphate. N-(3'-Dimethylaminopropyl)-N'-ethylcarbodiimide hydrochloride is preferred.

The equivalent amount of the condensation agent is preferably 1 to 10 equivalents, more preferably 1.1 to 1.5 equivalents, with respect to the carboxylic acid derivative represented by formula (XV).

Examples of the base which is used for the condensation reaction include organic bases such as diisopropylethylamine, triethylamine, pyridine and N-methylmorpholine, and organic acid salts such as potassium carbonate, sodium carbonate and sodium bicarbonate. Diisopropylethylamine or triethylamine is preferred.

The equivalent amount of the base is preferably 0 to 10 equivalents, more preferably 1 to 3 equivalents, with respect to the carboxylic acid derivative represented by formula (XV).

Examples of the solvent which is used for the condensation reaction include N,N-dimethylformamide, tetrahydrofuran, dichloromethane, chloroform and diethyl ether. Dichloromethane is preferred.

The reaction temperature of the condensation reaction is preferably 0 to 50° C., more preferably from 0 to 30° C. The reaction time of the condensation reaction is preferably 1 to 48 hours, more preferably 2 to 5 hours.

The amine derivative represented by formula (XIV) can be synthesized, for instance, as shown in scheme 3, by the protecting group introduction reaction into the carboxylic acid of an amino acid derivative represented by formula (XVI) and the Boc deprotection reaction of the obtained amino acid derivative represented by formula (XVII), or, as shown in scheme 4, by the protecting group introduction reaction into the carboxylic acid of an amino acid derivative represented by formula (XIX) and the Fmoc deprotection reaction of the obtained amino acid derivative represented by formula (XX).

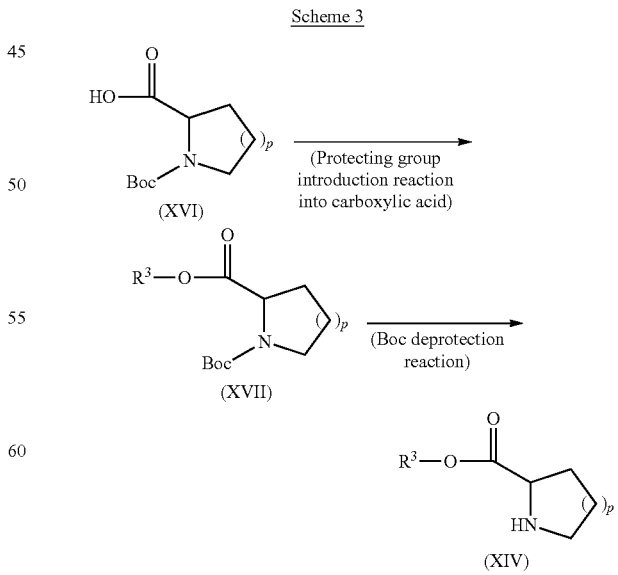

In the formulae, $R^3$ and p are as defined above.

Scheme 4

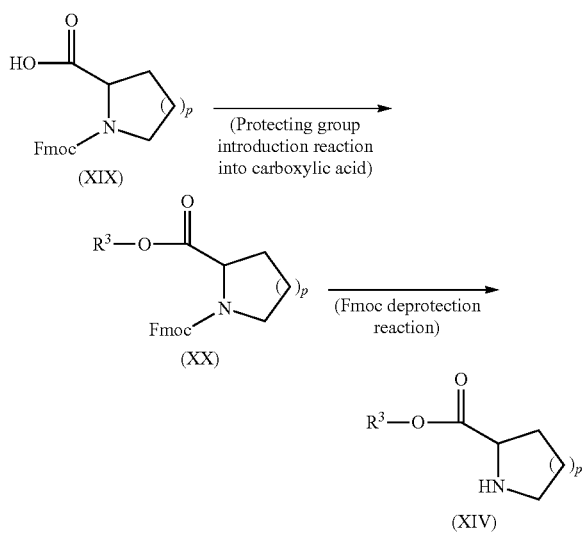

In the formulae, R³ and p are as defined above.

The protecting group introduction reaction into the carboxylic acid can be carried out by a known method described in, for instance, Protective Groups in Organic Synthesis, 4th edition, Greene et al., 2007, John Wiley & Sons, Inc.

The Boc deprotection reaction or the Fmoc deprotection reaction can be carried out by a known method described in, for instance, Protective Groups in Organic Synthesis, 4th edition, Greene et al., 2007, John Wiley & Sons, Inc.

The amino acid derivative represented by formula (XVI) or formula (XIX) can be purchased or can be produced by a known method or a method equivalent thereto.

In another example, to link linker $Lx^2$ to the 5' end of X, a monomer for RNA synthesis represented by formula (X') given below may be used. This monomer corresponds basically to the linker represented by formula (IV'), and the description about the linker represented by formula (IV') is thus applied to the monomer represented by formula (X') given below. We also provide a monomer for RNA synthesis (amidite) represented by formula (X'):

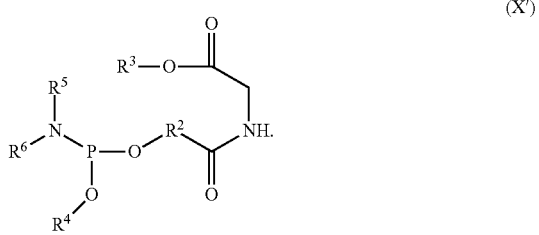

In formula (X'), the description of formula (IV') can be cited for the same sites as in formula (IV'). Specifically, in (X'), $R^2$ is an alkylene chain having n carbon atoms. In this context, any hydrogen atom on a carbon atom of the alkylene chain $R^2$ may be substituted by any substituent or may not be substituted. n is not particularly limited and can be appropriately set depending on the desired length of the linker $Lx^2$. For instance, from the viewpoints of production cost and yield, n is preferably an integer of 1 to 30, more preferably an integer of 1 to 20, further preferably an integer of 1 to 15. In formula (X'), $R^3$ is a carboxylic acid-protecting group. For instance, the disclosure of Protective Groups in Organic Synthesis, 4th edition, Greene et al., 2007, John Wiley & Sons, Inc. may be incorporated for the carboxylic acid-protecting group. Specific examples of the carboxylic acid-protecting group include a DMTr group, a Tr group, a TBDMS group, an ACE group, a TOM group, a CEE group, a CEM group, a CE group, a TEM group and a 2,4-dimethoxybenzyl group. A CE group is preferred.

$R^4$ is an alkyl group substituted by an electron-withdrawing group. Specific examples thereof include a 2-cyanoethyl group (a CE group) and a nitrophenylethyl group. A 2-cyanoethyl group (a CE group) is preferred.

$R^5$ and $R^6$ are each independently an alkyl group and may be the same or different. Specific examples of $—NR^5R^6$ include a diisopropylamino group, a diethylamino group, and an ethylmethylamino group. A diisopropylamino group is preferred.

Preferably, the monomer represented by formula (X') may be represented by formula (XXIII):

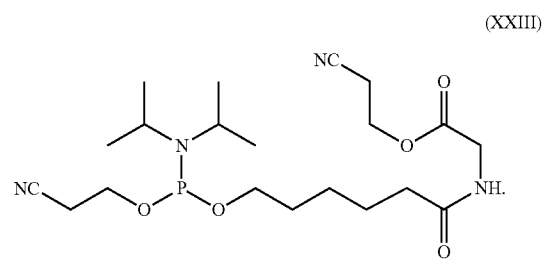 [SMILES: CC(C)N(C(C)C)P(OCCC#N)OCCCCCC(=O)NCC(=O)OCCC#N]

The monomer represented by formula (X') can be produced, for instance, by substantially the same procedure as in schemes 1 to 3 using an amino acid derivative represented by formula (XVI') instead of the amino derivative represented by formula (XVI):

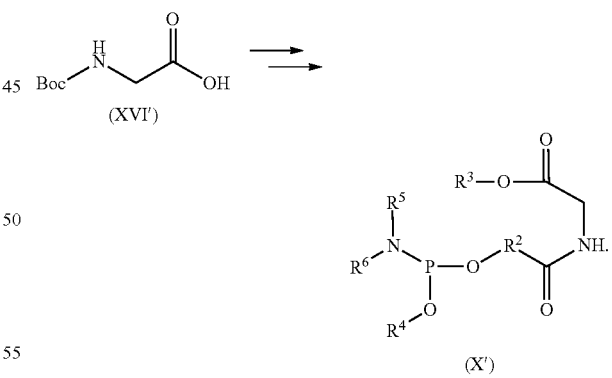

The amino acid derivative represented by formula (XVI') can be purchased or can be produced by a known method or a method equivalent thereto.

To link the linker Ly to the 5' end of Yc, any monomer for RNA synthesis suitable therefor, for instance, a known monomer for RNA synthesis described in JP Patent Nos. 5261677 or 5876890 can be used.

In the hairpin single-stranded RNA molecule produced by our method, X—Y comprises a gene expression-inhibiting sequence for a target gene. The gene expression-inhibiting sequence may be contained only in X or only in Y. The gene expression-inhibiting sequence is preferably the whole or part of a sense or antisense sequence of mRNA transcribed from the target gene.

The hairpin single-stranded RNA molecule may contain one or two or more gene expression-inhibiting sequences. The hairpin single-stranded RNA molecule may have, for instance, the same two or more gene expression-inhibiting sequences for the same target gene, may have two or more different gene expression-inhibiting sequences for the same target, or may have two or more different gene expression-inhibiting sequences for different target genes. The hairpin single-stranded RNA molecule having two or more gene expression-inhibiting sequences for different target genes is useful for inhibiting expression of two or more different target genes. The "gene" refers to a genome region from which mRNA is transcribed, and may be a protein-coding region or an RNA-coding region.

The hairpin single-stranded RNA molecule has an ability to inhibit expression of a target gene via a gene expression-inhibiting sequence. The target gene expression inhibiting using our hairpin single-stranded RNA molecule is preferably mediated, but not limited to, by RNA interference. The RNA interference is a phenomenon that generally speaking, a long double-stranded RNA (dsRNA) is cleaved in a cell, by Dicer, into an about 19- to 21-bp short double-stranded RNA (siRNA: small interfering RNA), the 3' end of which protrudes; one of the single-stranded RNAs binds to a target mRNA; and the target mRNA is degraded so that translation of the target mRNA is repressed, which makes it possible to inhibit expression of a target gene derived from the target mRNA. For instance, various kinds of a single-stranded RNA sequence included in siRNA bound to a target mRNA have been reported in accordance with the kinds of a target gene. For instance, a single-stranded RNA sequence included in siRNA can be used as a gene expression-inhibiting sequence. The hairpin single-stranded RNA molecule produced by our method can inhibit expression of a target gene while cleaved in vivo to generate siRNA. The hairpin single-stranded RNA molecule can be used for treatment or prophylaxis of disease or disorder involving expression or an increase in expression of a target gene.

The gene expression-inhibiting sequence may have a nucleotide length of preferably from 19 to 30 nucleotides, more preferably from 19 to 27 nucleotides, and, for instance, 19, 20, 21, 22, or 23 nucleotides. The gene expression-inhibiting sequence preferably consists of an RNA sequence completely identical or completely complementary to at least part of mRNA sequence of the target gene.

Examples of the target gene include, but are not particularly limited to, TGF-β1 gene, GAPDH gene, LAMA1 gene, and LMNA gene. When the target gene is TGF-β1 gene, the hairpin single-stranded RNA molecule produced by our method inhibits expression of the TGF-β1 gene in vivo. Such a hairpin single-stranded RNA molecule can be used, through TGF-β1 gene expression inhibiting, to treat or prevent disease or disorder involving expression or an increase in expression of the TGF-β1 gene such as lung fibrosis and/or acute pulmonary disease.

Figure 2:
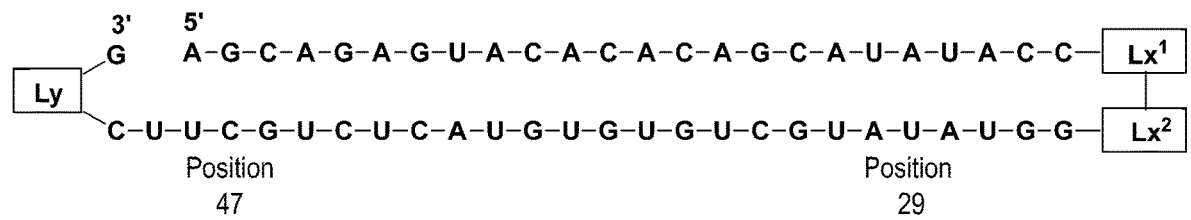
FIG. 2 is a schematic diagram of an ssTbRNA molecule (SEQ ID NO: 1). $Lx^1$ denotes a non-nucleotide linker having an amino group, Ly denotes a non-nucleotide linker, and $Lx^2$ denotes a non-nucleotide linker having a carboxyl group. From positions 29 (U) to 47 (C) of SEQ ID NO: 1 correspond to an active sequence (a gene expression-inhibiting sequence for TGF-β1 gene).

One example of the hairpin single-stranded RNA molecule containing a gene expression-inhibiting sequence produced by our method has the nucleotide sequence set forth in SEQ ID NO: 1 and is obtained from a combination of a first single-stranded oligo-RNA molecule having the nucleotide sequence set forth in SEQ ID NO: 2 (strand A) and a second single-stranded oligo-RNA molecule having the nucleotide sequence set forth in SEQ ID NO: 3 (strand B). The nucleotide sequence set forth in SEQ ID NO: 1 contains a gene expression-inhibiting sequence for TGF-β1 gene serving as a target gene. The sequence from positions 29 to 47 of the nucleotide sequence set forth in SEQ ID NO: 1 corresponds to a gene expression-inhibiting sequence (an active sequence) (FIG. 2).

Another example thereof has the nucleotide sequence set forth in SEQ ID NO: 4 and is obtained from a combination of a first single-stranded oligo-RNA molecule having the nucleotide sequence set forth in SEQ ID NO: 5 (strand C) and a second single-stranded oligo-RNA molecule having the nucleotide sequence set forth in SEQ ID NO: 6 (strand D). The nucleotide sequence set forth in SEQ ID NO: 4 contains a gene expression-inhibiting sequence for GAPDH gene serving as a target gene. The sequence from positions 27 to 45 of the nucleotide sequence set forth in SEQ ID NO: 4 corresponds to a gene expression-inhibiting sequence (an active sequence).

The hairpin single-stranded RNA molecule can be produced by reacting the first single-stranded oligo-RNA molecule represented by formula (I) with the second single-stranded oligo-RNA molecule represented by formula (II) in the presence of a dehydration condensation agent (also referred to as a condensation agent) in a reaction solvent to form an amide bond between linker $Lx^1$ and linker $Lx^2$. The reaction solvent is a mixed solvent comprising a buffer solution and a hydrophilic organic solvent.

Examples of the buffer solution include, but are not limited to, a 2-(N-morpholino)ethanesulfonic acid buffer solution (hereinafter, a MES buffer solution), a 3-(N-morpholino)-2-hydroxypropanesulfonic acid buffer solution (hereinafter, a MOPSO buffer solution), a piperazine-1,4-bis(2-ethanesulfonic acid) buffer solution (hereinafter, a PIPES buffer solution), a 3-(N-morpholino)propanesulfonic acid buffer solution (hereinafter, a MOPS buffer solution), a N,N-bis(2-hydroxyethyl)-2-aminoethanesulfonic acid buffer solution (hereinafter, a BES buffer solution), a 3-[N,N-bis(2-hydroxyethyl)amino]-2-hydroxypropanesulfonic acid buffer solution (hereinafter, a DIPSO buffer solution), a 2-[4-(2-hydroxyethyl)-1-piperazinyl]ethanesulfonic acid buffer solution (hereinafter, a HEPES buffer solution), a piperazine-1,4-bis(2-hydroxypropanesulfonic acid) buffer solution (hereinafter, a POPSO buffer solution), a 4-(2-hydroxyethyl)piperazine-1-(2-hydroxypropane-3-sulfonic acid buffer solution (hereinafter, a HEPPSO buffer solution), and a 4-(2-hydroxyethyl)-1-piperazinepropanesulfonic acid buffer solution (hereinafter, a HEPPS buffer solution). For instance, a MES buffer solution or a MOPS buffer solution is preferably used.

The pH of the buffer solution can be appropriately adjusted and is preferably 6.5 to 7.5, more preferably 6.9 to 7.5, for instance, 6.5 to 7.0, 6.9 to 7.1, or 7.0 to 7.5.

A hydrophilic organic solvent can be used as a component of the reaction solvent. The hydrophilic organic solvent may be, for instance, a hydrophilic aprotic organic solvent.

The hydrophilic organic solvent means an organic solvent that can be mixed with water at an arbitrary ratio. Examples thereof include sulfone-based solvents such as sulfolane, sulfoxide-based solvents such as dimethyl sulfoxide, amide-based solvents such as N,N-dimethylformamide and N-methylpyrrolidone, urea-based solvents such as N,N'-dimethylethyleneurea, nitrile-based solvents such as acetonitrile, ether-based solvents such as tetrahydrofuran and 1,2-dimethoxyethane, and alcohol-based solvents such as ethanol and tert-butyl alcohol. The "aprotic" organic solvent means an organic solvent having no proton-donating property. Examples of the hydrophilic aprotic organic solvent include sulfone-based solvents such as sulfolane, sulfoxide-based solvents such as dimethyl sulfoxide, amide-based solvents such as N,N-dimethylformamide and N-methylpyrrolidone, urea-based solvents such as N,N'-dimethylethyleneurea, nitrile-based solvents such as acetonitrile, and ether-based solvents such as tetrahydrofuran and 1,2-dimethoxyethane. Dimethyl sulfoxide (hereinafter, DMSO), N,N-dimethylformamide (hereinafter, DMF), N,N'-dimethylethyleneurea (hereinafter, DMEU), or acetonitrile is preferred, and DMSO or DMF is more preferred.

In adding a dehydration condensation agent or an N-hydroxy nitrogen-containing aromatic compound (e.g., hydroxybenzotriazole or a derivative thereof), a cyano(hydroxyimino)acetic acid ester, or an N-hydrocarbon-substituted imidazole derivative dissolved or suspended in an organic solvent, the organic solvent is included in the "organic solvent" in the mixed solvent. These organic solvents may be used each alone or may be used in combination of two or more thereof.

In one example, the ratio of the organic solvent in the mixed solvent serving as a reaction solvent may be 15 to 70 v/v %, for instance, 20 to 70 v/v %, 20 to 65 v/v %, 35 to 60 v/v %, 35 to 55 v/v %, or 50 to 55 v/v %, of the amount of the whole solvent (the total amount of the mixed solvent comprising the buffer solution and the organic solvent). In adding a dehydration condensation agent or an N-hydroxy nitrogen-containing aromatic compound (e.g., hydroxybenzotriazole or a derivative thereof), a cyano(hydroxyimino) acetic acid ester, or an N-hydrocarbon-substituted imidazole derivative dissolved or suspended in a solution such as water, a buffer solution or an organic solvent, the amount of the whole solvent includes the amount of the solution containing the dehydration condensation agent, the N-hydroxy nitrogen-containing aromatic compound (e.g., hydroxybenzotriazole or a derivative thereof), the cyano(hydroxyimino)acetic acid ester, or the N-hydrocarbon-substituted imidazole derivative. In adding a dehydration condensation agent or an N-hydroxy nitrogen-containing aromatic compound (e.g., hydroxybenzotriazole or a derivative thereof), a cyano(hydroxyimino)acetic acid ester, or an N-hydrocarbon-substituted imidazole derivative dissolved or suspended in an organic solvent, the amount of the organic solvent for calculation of the ratio of the organic solvent in the mixed solvent is included in the total amount of organic solvents in the mixed solvent.

When the hydrophilic organic solvent is DMSO, the ratio of DMSO in the mixed solvent is preferably 20 to 65 v/v %, more preferably 35 to 60 v/v %, further preferably 50 to 55 or 50 to 60 v/v %, of the amount of the whole solvent. When the hydrophilic organic solvent is DMSO and the dehydration condensation agent is a uronium-based dehydration condensation agent comprising an N-hydroxy nitrogen-containing aromatic ring structure, for instance, a benzotriazolyluronium-based dehydration condensation agent such as HATU, the ratio of DMSO in the mixed solvent may be preferably 35 to 65 v/v %, more preferably 50 to 65 v/v %, for instance 50 to 60 v/v %, of the amount of the whole solvent. When the hydrophilic organic solvent is DMSO and the dehydration condensation agent is a triazine-based dehydration condensation agent, for instance, a triazine-based quaternary morpholinium derivative such as DMT-MM, the ratio of DMSO in the mixed solvent may be preferably 35 to 65 v/v %, more preferably 35 to 60 v/v %, for instance, 50 to 60 v/v % or 50 to 55 v/v %, of the amount of the whole solvent. In these examples, the pH of the reaction solvent (mixed solvent) may be, but not limited to, preferably 6.5 to 7.5, more preferably 6.9 to 7.5, for instance, 6.5 to 7.0, 6.9 to 7.1, or 7.0 to 7.5.

When the hydrophilic organic solvent is DMF, the ratio of DMF in the mixed solvent is preferably 20 to 65 v/v %, more preferably 35 to 65 v/v %, further preferably 50 to 65 v/v %, of the amount of the whole solvent. When the hydrophilic organic solvent is DMF and the dehydration condensation agent is a uronium-based dehydration condensation agent comprising an N-hydroxy nitrogen-containing aromatic ring structure, for instance, a benzotriazolyluronium-based dehydration condensation agent such as HATU, the ratio of DMF in the mixed solvent may be preferably 35 to 65 v/v %, more preferably 50 to 65 v/v %, for instance, 50 to 60 v/v %, of the amount of the whole solvent. In these examples, the pH of the reaction solvent (mixed solvent) may be, but not limited to, preferably 6.5 to 7.5, more preferably 6.9 to 7.5, for instance, 6.5 to 7.0, 6.9 to 7.1, or 7.0 to 7.5.

When the hydrophilic organic solvent is DMEU, the ratio of DMEU in the mixed solvent is preferably 20 to 65 v/v %, more preferably 35 to 65 v/v %, further preferably 50 to 60 v/v %, of the amount of the whole solvent. When the hydrophilic organic solvent is DMEU and the dehydration condensation agent is a uronium-based dehydration condensation agent comprising an N-hydroxy nitrogen-containing aromatic ring structure, for instance, a benzotriazolyluronium-based dehydration condensation agent such as HATU, the ratio of DMEU in the mixed solvent may be preferably 35 to 65 v/v %, more preferably 50 to 65 v/v %, for instance, 50 to 60 v/v %, of the amount of the whole solvent. In these examples, the pH of the reaction solvent (mixed solvent) may be, but not limited to, preferably 6.5 to 7.5, more preferably 6.9 to 7.5, for instance, 6.5 to 7.0, 6.9 to 7.1, or 7.0 to 7.5.

When the hydrophilic organic solvent is acetonitrile, the ratio of acetonitrile in the mixed solvent is preferably 20 to 65 v/v %, more preferably 35 to 65 v/v %, further preferably 50 to 65 v/v %, of the amount of the whole solvent. When the hydrophilic organic solvent is acetonitrile and the dehydration condensation agent is a uronium-based dehydration condensation agent comprising an N-hydroxy nitrogen-containing aromatic ring structure, for instance, a benzotriazolyluronium-based dehydration condensation agent such as HATU, the ratio of acetonitrile in the mixed solvent may be preferably 35 to 65 v/v %, more preferably 50 to 65 v/v %, for instance, 50 to 60 v/v %, of the amount of the whole solvent. In these examples, the pH of the reaction solvent (mixed solvent) may be, but not limited to, preferably 6.5 to 7.5, more preferably 6.9 to 7.5, for instance, 6.5 to 7.0, 6.9 to 7.1, or 7.0 to 7.5.

The order of addition of the buffer solution and the hydrophilic organic solvent is not particularly limited. The first single-stranded oligo-RNA molecule and the second single-stranded oligo-RNA molecule may be dissolved in the buffer solution, and then, the hydrophilic organic solvent can be added to the solution, or the hydrophilic organic solvent may be added to the first single-stranded oligo-RNA molecule and the second single-stranded oligo-RNA molecule, and then, the buffer solution can be added thereto. Alternatively, the buffer solution and the hydrophilic organic solvent may be mixed beforehand, and the resulting solvent can be mixed with the first single-stranded oligo-RNA molecule and the second single-stranded oligo-RNA molecule. Usually, it is preferred to dissolve the first single-stranded oligo-RNA molecule and the second single-stranded oligo-RNA molecule in the buffer solution and then add the hydrophilic organic solvent to the solution.

The first single-stranded oligo-RNA molecule and the second single-stranded oligo-RNA molecule may be dissolved in the buffer solution and then allowed to stand over a certain period (e.g., from 1 to 15 minutes), or the solution may be immediately added to the hydrophilic organic solvent without being allowed to stand. Heat denaturation (e.g., heating at a temperature of 90° C. or higher and then cooling to room temperature) of the first single-stranded oligo-RNA molecule and the second single-stranded oligo-RNA molecule in the buffer solution may or may not be carried out.

The dehydration condensation agent that can be used in the production method can be (i) a triazine-based dehydration condensation agent, (ii) a uronium-based dehydration condensation agent comprising an N-hydroxy nitrogen-containing aromatic ring structure (e.g., a benzotriazolyluronium-based dehydration condensation agent), (iii) a carbodiimide-based dehydration condensation agent, (iv) a 2-halopyridinium-based dehydration condensation agent, or (v) a formamidinium-based dehydration condensation agent. In using (iii) a carbodiimide-based dehydration condensation agent as the dehydration condensation agent, the carbodiimide-based dehydration condensation agent can be used in combination with an N-hydroxy nitrogen-containing aromatic compound (e.g., hydroxybenzotriazole or a derivative thereof) or a cyano(hydroxyimino)acetic acid ester. In using (iv) a 2-halopyridinium-based dehydration condensation agent, the 2-halopyridinium-based dehydration condensation agent can be used in combination with an N-hydroxy nitrogen-containing aromatic compound. In using (v) a formamidinium-based dehydration condensation agent, the formamidinium-based dehydration condensation agent can be used in combination with an N-hydroxy nitrogen-containing aromatic compound or an N-hydrocarbon-substituted imidazole derivative. In the production method, reaction conditions can be suitably used which cause amidation by way of an N-acyloxy nitrogen-containing aromatic compound-based active intermediate (e.g., a benzotriazolyl-based active intermediate), a cyano(acyloxyimino)acetic acid ester-based active intermediate or a N'-acyl-N-hydrocarbon-substituted imidazole-based active intermediate. The dehydration condensation agent may be in a free form or salt form and is preferably in a salt form.

In one example, the production method may satisfy at least one condition selected from the group of conditions (i) to (iv) or any combination thereof (e.g., all the conditions):
 (i) a uronium-based dehydration condensation agent comprising an N-hydroxy nitrogen-containing aromatic ring structure is used and is a benzotriazolyluronium-based dehydration condensation agent,
 (ii) an N-hydroxy nitrogen-containing aromatic compound is used and is hydroxybenzotriazole or a derivative thereof,
 (iii) a cyano(hydroxyimino)acetic acid ester is used and is a cyano(hydroxyimino)acetic acid alkyl ester, and
 (iv) an N-hydrocarbon-substituted imidazole derivative is used and is an N-alkylimidazole derivative.

The triazine-based dehydration condensation agent means a compound (e.g., a free form or a salt) having a structure where at least one carbon atom of triazine is replaced by an eliminable functional group such as quaternary ammonium or halogen. For instance, a dehydration condensation agent described in Kunishima et al., Tetrahedron, 2001, Vol. 57, p. 1551-1558; Kunishima et al., Chemistry A European Journal, 2012, Vol. 18, p. 15856-15867; JP Patent No. 4349749, JP Patent Publication (Kokai) No. 2008-214473 A (2008), JP Patent Publication (Kokai) No. 2016-141618 A (2016), JP Patent Publication (Kokai) No. 2016-141619 A (2016), JP Patent Publication (Kokai) No. 2017-149876 A (2017) and the like can be used as the triazine-based dehydration condensation agent. More specifically, examples of the triazine-based dehydration condensation agent include triazine-based quaternary morpholinium, for instance, 4-[4,6-bis(2,6-xylyl)-1,3,5-triazin-2-yl]-4-methylmorpholinium, 4-[4-methoxy-6-(2,6-xylyl)-1,3,5-triazin-2-yl]-4-methylmorpholinium, 4-(4-t-butyl-6-methoxy-1,3,5-triazin-2-yl)4-methoxymorpholinium, 4-(4,6-di-t-butyl-1,3,5-triazin-2-yl)-4-methylmorpholinium, N-[4-meth-oxy-6-(N'-phenylacetamido)-1,3,5-triazin-2-yl]-4-methylmorpholinium, N-[4-methoxy-6-(N'-methylacetamido)-1,3,5-triazin-2-yl]-4-methylmorpholinium, N-[4-methoxy-6-(N'-phenylbenzamido)-1,3,5-triazin-2-yl]-4-methylmorpholinium, N-[4-methoxy-6-(N'-methylbenzamido)-1,3,5-triazin-2-yl]-4-methylmorpholinium, N-[4-methoxy-6-(2,5-dioxopyrrolidyl)-1,3,5-triazin-2-yl]-4-methylmorpholinium, N-[4-methoxy-6-(2-piperidon-1-yl)-1,3,5-triazin-2-yl]-4-methylmorpholinium, 4-(4,6-dimethoxy-1,3,5-triazin-2-yl)-4-methylmorpholinium, and 4-(4,6-dimeth-oxy-1,3,5-triazin-2-yl)-4-methylmorpholinium, and derivatives thereof. Examples of the derivatives include salts such as perchlorate, trifluoromethanesulfonate, chloride, and hexafluorophosphate. The triazine-based dehydration condensation agent can be, for instance, 4-(4,6-dimethoxy-1,3,5-triazin-2-yl)-4-methylmorpholinium salt.

The triazine-based quaternary morpholinium derivative as the triazine-based dehydration condensation agent is preferably, for instance, 4-[4,6-bis(2,6-xylyl)-1,3,5-triazin-2-yl]-4-methylmorpholinium perchlorate, 4-[4-methoxy-6-(2,6-xylyl)-1,3,5-triazin-2-yl]-4-methylmorpholinium perchlorate, 4-(4-t-butyl-6-methoxy-1,3,5-triazin-2-yl)4-methoxymorpholinium trifluoromethanesulfonate, 4-(4,6-di-t-butyl-1,3,5-triazin-2-yl)-4-methylmorpholinium chloride, N-[4-methoxy-6-(N'-phenylacetamido)-1,3,5-triazin-2-yl]-4-methylmorpholinium perchlorate, N-[4-methoxy-6-(N'-methylacetamido)-1,3,5-triazin-2-yl]-4-methylmorpholinium perchlorate, N-[4-methoxy-6-(N'-phenylbenzamido)-1,3,5-triazin-2-yl]-4-methylmorpholinium chloride, N-[4-methoxy-6-(N'-methylbenzamido)-1,3,5-triazin-2-yl]-4-methylmorpholinium chloride, N-[4-methoxy-6-(2,5-dioxopyrrolidyl)-1,3,5-triazin-2-yl]-4-methylmorpholinium chloride, N-[4-meth-oxy-6-(2-piperidon-1-yl)-1,3,5-triazin-2-yl]-4-methylmorpholinium chloride, 4-(4,6-dimethoxy-1,3,5-triazin-2-yl)-4-methylmorpholinium chloride, or 4-(4,6-dimethoxy-1,3,5-triazin-2-yl)-4-methylmorpholinium trifluoromethanesulfonate, more preferably 4-(4,6-dimethoxy-1,3,5-triazin-2-yl)-4-methylmorpholinium chloride (hereinafter, DMT-MM).

The equivalent amount of the triazine-based dehydration condensation agent is preferably 10 to 100 equivalents, more preferably 20 to 40 equivalents, with respect to the first single-stranded oligo-RNA molecule.

The uronium-based dehydration condensation agent comprising an N-hydroxy nitrogen-containing aromatic ring structure means a compound having a tetraalkylamidinium structure added to a N-hydroxy nitrogen-containing aromatic ring structure. The uronium-based dehydration condensation agent comprising an N-hydroxy nitrogen-containing aromatic ring structure is preferably, for instance, a benzotriazolyluronium-based dehydration condensation agent (a uronium-based dehydration condensation agent having a 1-hydroxybenzotriazole structure), a uronium-based dehydration condensation agent having an N-hydroxy-2-pyridone structure, a uronium-based dehydration condensation agent having a 3,4-dihydro-3-hydroxy-4-oxo-1,2,3-benzotriazine structure, a uronium-based dehydration condensation agent having an N-hydroxyimidazole structure, or a uronium-based dehydration condensation agent having an N-hydroxypyridine structure, more preferably a benzotriazolyluronium-based dehydration condensation agent, a uronium-based dehydration condensation agent having an N-hydroxy-2-pyridone structure, or a uronium-based dehydration condensation agent having a 3,4-dihydro-3-hydroxy-4-oxo-1,2,3-benzotriazine structure, further preferably a benzotriazolyluronium-based dehydration condensation agent, or a uronium-based dehydration condensation agent having a 3,4-dihydro-3-hydroxy-4-oxo-1,2, 3-benzotriazine structure.

The benzotriazolyluronium-based dehydration condensation agent means a compound having a tetraalkylamidinium structure added to a 1-hydroxybenzotriazole structure. Four substituents on two nitrogen atoms of the amidinium structure are not particularly limited and these substituents may form a ring together with the nitrogen atoms, as long as the substituents do not inhibit amidation reaction. The 1-hydroxybenzotriazole structure is not particularly limited and may have a substituent on its benzene ring and/or may have nitrogen atom(s) substituted for some carbon atom(s) within the benzene ring, as long as the structure does not inhibit amidation reaction.

The benzotriazolyluronium-based dehydration condensation agent is commonly known to assume two forms, an O-acyl form (uronium form) and an N-acyl form (aminium form), according to Carpino et al., Angewandte Chemie International Edition, 2002, Vol. 41, p. 441-445. The "benzotriazolyluronium-based dehydration condensation agent" encompasses both the O-acyl form (uronium-based) and the N-acyl form (aminium-based):

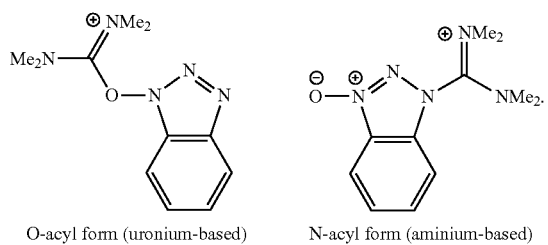

O-acyl form (uronium-based)   N-acyl form (aminium-based)

For instance, a dehydration condensation agent described in Knorr et al., Tetrahedron Letters, 1989, Vol. 30, p. 1927-1930; Carpino et al., Organic Letters, 2001, Vol. 3, p. 2793-2795; EL-Faham et al., The Journal of Organic Chemistry, 2008, Vol. 73, p. 2731-2737; WO 1994/007910, WO 2002/094822 and the like can be used as the benzotriazolyluronium-based dehydration condensation agent. More specifically, examples of the benzotriazolyluron-ium-based dehydration condensation agent include benzotriazolyluronium, for instance, O-(benzotriazol-1-yl)-N,N,N',N'-tetramethyluronium, [(benzotriazol-1-yloxy)piperidin-1-ylmethylene]piperidinium, and derivatives thereof, and azabenzotriazolyluronium, for instance, 0-(7-azabenzotriazol-1-yl)-N,N,N',N'-tetramethyluronium, 0-(7-azabenzotriazol-1-yl)-N,N,N',N'-tetraethyluronium, [(7-azabenzotriazol-1-yloxy)-4-morpholinomethylene]dimethylammonium, [(7-azabenzotriazol-1-yloxy)piperidin-1-ylmethylene]piperidinium, [(7-azabenzotriazol-1-yloxy)pyrrolidin-1-ylmethylene]pyrrolinium, and derivatives thereof. Examples of the derivatives include salts such as perchlorate, trifluoromethanesulfonate, chloride, and hexafluorophosphate. The benzotriazolyluronium-based dehydration condensation agent may be, for instance, O-(benzotriazol-1-yl)-N,N,N',N'-tetramethyluronium salt or O-(7-azabenzotriazol-1-yl)-N,N,N',N'-tetramethyluronium salt.

Preferred examples of the benzotriazolyluronium-based dehydration condensation agent include O-(benzotriazol-1-yl)-N,N,N',N'-tetramethyluronium hexafluorophosphate and 0-(7-azabenzotriazol-1-yl)-N,N,N',N'-tetramethyluronium hexafluorophosphate (hereinafter, HATU).

The uronium-based dehydration condensation agent having an N-hydroxy-2-pyridone structure means a compound having a tetraalkylamidinium structure added to an N-hydroxy-2-pyridone structure. Four substituents on two nitrogen atoms of the amidinium structure are not particularly limited and these substituents may form a ring together with the nitrogen atoms, as long as the substituents do not inhibit amidation reaction. The N-hydroxy-2-pyridone structure is not particularly limited and may have a substituent on its pyridone ring, as long as the structure does not inhibit amidation reaction. Examples of the uronium-based dehydration condensation agent having an N-hydroxy-2-pyridone structure include O-(1,2-dihydro-2-oxo-1-pyridyl)-N,N,N',N'-tetramethyluronium, O-(1,2-dihydro-2-oxo-1-pyridyl)-N,N,N',N'-bis(tetramethyl-ene)uronium, and O-(1,2-dihydro-2-oxo-1-pyridyl)-N,N,N',N'-bis(pentamethylene)uronium, and derivatives thereof. Examples of the derivatives include salts such as chloride, bromide, iodide, perchlorate, trifluoromethanesulfonate, tetrafluoroborate, and hexafluorophosphate. The uronium-based dehydration condensation agent having an N-hydroxy-2-pyridone structure may be O-(1,2-dihydro-2-oxo-1-pyridyl)-N,N,N',N'-tetramethyluronium salt.

Preferred examples of the uronium-based dehydration condensation agent having an N-hydroxy-2-pyridone structure include O-(1,2-dihydro-2-oxo-1-pyridyl)-N,N,N',N'-tetramethyluronium tetrafluoroborate (hereinafter, TPTU).

The uronium-based dehydration condensation agent having a 3,4-dihydro-3-hydroxy-4-oxo-1,2,3-benzotriazine structure means a compound having a tetraalkylamidinium structure added to a 3,4-dihydro-3-hydroxy-4-oxo-1,2,3-benzotriazine structure. Four substituents on two nitrogen atoms of the amidinium structure are not particularly limited and these substituents may form a ring together with the nitrogen atoms, as long as the substituents do not inhibit amidation reaction. The 3,4-dihydro-3-hydroxy-4-oxo-1,2,3-benzotriazine structure is not particularly limited and may have a substituent on its 4-oxo-1,2,3-benzotriazine ring, as long as the structure does not inhibit amidation reaction. Examples of the uronium-based dehydration condensation agent having a 3,4-dihydro-3-hydroxy-4-oxo-1,2,3-benzotriazine structure include 0-(3,4-dihydro-4-oxo-1,2,3-benzotriazin-3-yl)-N,N,N',N'-tetramethyluronium, O-(3,4-dihydro-4-oxo-1,2,3-benzotriazin-3-yl)-N,N,N',N'-bis(tetramethylene)uronium, 0-(3,4-dihydro-4-oxo-1,2,3-benzotriazin-3-yl)-N,N,N',N'-bis(pentamethylene)uronium, and derivatives thereof. Examples of the derivatives include salts such as chloride, bromide, iodide, perchlorate, trifluoromethanesulfonate, tetrafluoroborate, and hexafluorophosphate. The uronium-based dehydration condensation agent having a 3,4-dihydro-3-hydroxy-4-oxo-1,2,3-benzotriazine structure may be O-(3,4-dihydro-4-oxo-1,2,3-benzotriazin-3-yl)-N,N,N',N'-tetramethyluronium salt.

Preferred examples of the uronium-based dehydration condensation agent having a 3,4-dihydro-3-hydroxy-4-oxo- 1,2,3-benzotriazine structure include O-(3,4-dihydro-4-oxo-1,2,3-benzotriazin-3-yl)-N,N,N',N'-tetramethyluronium tetrafluoroborate (hereinafter, TDBTU).

The uronium-based dehydration condensation agent having an N-hydroxyimidazole structure means a compound having a tetraalkylamidinium structure added to an N-hydroxyimidazole structure. Four substituents on two nitrogen atoms of the amidinium structure are not particularly limited and these substituents may form a ring together with the nitrogen atoms, as long as the substituents do not inhibit amidation reaction. The N-hydroxyimidazole structure is not particularly limited and may have a substituent on its N-hydroxyimidazole ring, as long as the structure does not inhibit amidation reaction. Examples of the uronium-based dehydration condensation agent having an N-hydroxyimidazole structure include O-(imidazol-1-yl)-N,N,N',N'-tetramethyluronium, O-(imidazol-1-yl)-N,N,N',N'-bis(tetramethylene)uronium, O-(imidazol-1-yl)-N,N,N',N'-bis(pentamethylene)uronium, and derivatives thereof. Examples of the derivatives include salts such as chloride, bromide, iodide, perchlorate, trifluoromethanesulfonate, tetrafluoroborate, and hexafluorophosphate. The uronium-based dehydration condensation agent having an N-hydroxyimidazole structure may be O-(imidazol-1-yl)-N,N,N',N'-tetramethyluronium salt.

Preferred examples of the uronium-based dehydration condensation agent having an N-hydroxyimidazole structure include O-(imidazol-1-yl)-N,N,N',N'-tetramethyluronium hexafluorophosphate.

The uronium-based dehydration condensation agent having an N-hydroxypyridine structure means a compound having a tetraalkylamidinium structure added to an N-hydroxypyridine structure. Four substituents on two nitrogen atoms of the amidinium structure are not particularly limited and these substituents may form a ring together with the nitrogen atoms, as long as the substituents do not inhibit amidation reaction. The N-hydroxypyridine structure is not particularly limited and may have a substituent on its N-hydroxypyridine ring, as long as the structure does not inhibit amidation reaction. Examples of the uronium-based dehydration condensation agent having an N-hydroxypyridine structure include O-pyridyl-N,N,N',N'-tetramethyluronium, O-pyridyl-N,N,N',N'-bis(tetramethylene)uronium, O-pyridyl-N,N,N',N'-bis(pentamethylene)uronium, O-(4-dimethylamino-pyridyl)-N,N,N',N'-tetramethyluronium, O-(4-dimethylamino-pyridyl)-N,N,N',N'-bis(tetramethylene)uronium, O-(4-dimethyl-amino-pyridyl)-N,N,N',N'-bis(pentamethylene)uronium, and derivatives thereof. Examples of the derivatives include salts such as chloride, bromide, iodide, perchlorate, trifluoromethanesulfonate, tetrafluoroborate, and hexafluorophosphate. The uronium-based dehydration condensation agent having an N-hydroxypyridine structure may be O-pyridyl-N,N,N',N'-tetramethyluronium salt or O-4-dimethylamino-pyridyl)-N,N,N',N'-tetramethyluronium salt.

Preferred examples of the uronium-based dehydration condensation agent having an N-hydroxypyridine structure include O-(4-dimethylamino-pyridyl)-N,N,N',N'-tetramethyluronium hexafluorophosphate.

The equivalent amount of the uronium-based dehydration condensation agent comprising an N-hydroxy nitrogen-containing aromatic ring structure (e.g., a benzotriazolyluronium-based dehydration condensation agent) is preferably 10 to 100 equivalents, more preferably 20 to 40 equivalents, with respect to the first single-stranded oligo-RNA molecule.

The carbodiimide-based dehydration condensation agent means a compound having a carbodiimide structure represented by N=C=N. Substituents on N are not particularly limited as long as the substituents do not inhibit amidation reaction. For instance, a carbodiimide derivative such as N,N'-dimethylcarbodiimide, N,N'-diethylcarbodiimide, N,N'-dipropylcarbodiimide, N,N'-diisopropylcarbodiimide, N-tert-butyl-N'-methylcarbodiimide, N,N'-dicyclohexylcarbodiimide, N-benzyl-N'-methylcarbodiimide, N-benzyl-N'-ethylcarbodiimide, N-benzyl-N'-propylcarbodiimide, N-(3'-dimethylaminopropyl)-N'-ethylcarbodiimide, N,N'-bis(3'-dimethylaminopropyl)carbodiimide, 3-(ethyliminomethylideneamino)propyltrimethylammonium, or 3-(isopropyliminomethylideneamino)propyltrimethylammonium, or a salt (including an acid-addition salt) thereof can be used as the carbodiimide-based dehydration condensation agent. Examples of the salt include perchlorate, trifluoromethanesulfonate, chloride, hexafluorophosphate, hydrochloride, bromate, trifluoromethanesulfonate, and perchlorate. A carbodiimide derivative having a tertiary amine structure or quaternary ammonium structure is more preferred. Examples thereof include N-(3'-dimethylaminopropyl)-N'-ethylcarbodiimide and salts such as acid-addition salts thereof, N,N'-bis(3'-dimethylaminopropyl)carbodiimide and salts such as acid-addition salts thereof, 3-(ethyliminomethylideneamino)propyltrimethylammonium salt, and 3-(isopropyliminomethylideneamino)propyltrimethylammonium salt. Particularly preferred examples of the carbodiimide-based dehydration condensation agent include N-(3'-dimethylaminopropyl)-N'-ethylcarbodiimide hydrochloride (hereinafter, EDCI hydrochloride).

The N-hydroxy nitrogen-containing aromatic compound is preferably, for instance, hydroxybenzotriazole or a derivative thereof, N-hydroxytriazole or a derivative thereof, N-hydroxybenzimidazole or a derivative thereof, N-hydroxyimidazole or a derivative thereof, N-hydroxy-2-pyridone or a derivative thereof, 3,4-dihydro-3-hydroxy-4-oxo-1,2,3-benzotriazine or a derivative thereof, or N-hydroxypyridine or a derivative thereof, more preferably hydroxybenzotriazole or a derivative thereof, N-hydroxytriazole or a derivative thereof, N-hydroxy-2-pyridone or a derivative thereof, 3,4-dihydro-3-hydroxy-4-oxo-1,2,3-benzotriazine or a derivative thereof, or N-hydroxypyridine or a derivative thereof.

The hydroxybenzotriazole or the derivative thereof is not particularly limited and may have a substituent on its benzene ring and/or may have nitrogen atom(s) substituted for some carbon atom(s) within the benzene ring, as long as it does not inhibit amidation reaction. For instance, 1-hydroxybenzotriazole, 1-hydroxy-6-chloro-benzotriazole, 1-hydroxy-6-trifluoromethylbenzotriazole, 1-hydroxy-4-nitro-6-trifluoromethylbenzotriazole, 1-hydroxy-7-azabenzotriazole, 1-hydroxy-4-methyl-7-azabenzotriazole, 1-hydroxy-4-methoxy-7-azabenzotriazole, 1-hydroxy-4-tert-butyl-7-azabenzotriazole, 1-hydroxy-4,5,6-trimethyl-7-azabenzotriazole, 1-hydroxy-6-azabenzotriazole, 1-hydroxy-5-azabenzotriazole or 1-hydroxy-4-azabenzotriazole can be used as the hydroxybenzotriazole or the derivative thereof. The hydroxybenzotriazole or the derivative thereof is preferably a hydroxyazabenzotriazole or a derivative thereof such as 1-hydroxy-7-azabenzotriazole, 1-hydroxy-4-methyl-7-azabenzotriazole, 1-hydroxy-4-methoxy-7-azabenzotriazole, 1-hydroxy-4-tert-butyl-7-azabenzotriazole, 1-hydroxy-4,5,6-trimethyl-7-azabenzotriazole, 1-hydroxy-6-azabenzotriazole, 1-hydroxy-5-azabenzotriazole or 1-hydroxy-4-azabenzotriazole, more preferably 1-hydroxy-7-azabenzotriazole (hereinafter, HOAt).

The N-hydroxytriazole or the derivative thereof is not particularly limited and may have a substituent on its triazole ring at position 4 or 5, as long as it does not inhibit amidation reaction. Examples of the N-hydroxytriazole or the derivative thereof include ethyl 1-hydroxy-1,2,3-triazole-4-carboxylate.

The N-hydroxybenzimidazole or the derivative thereof is not particularly limited and may have a substituent on its benzene ring and/or may have nitrogen atom(s) substituted for some carbon atom(s) within the benzene ring, as long as it does not inhibit amidation reaction. Examples of the N-hydroxybenzimidazole or the derivative thereof include N-hydroxybenzimidazole, N-hydroxy-7-azabenzimidazole.

The N-hydroxyimidazole or the derivative thereof is not particularly limited and may have a substituent on its imidazole ring, as long as it does not inhibit amidation reaction. Examples of the N-hydroxyimidazole or the derivative thereof include N-hydroxyimidazole.

The N-hydroxy-2-pyridone or the derivative thereof is not particularly limited and may have a substituent on its pyridone ring at any of positions 3 to 6, as long as it does not inhibit amidation reaction. Examples of the N-hydroxy-2-pyridone or the derivative thereof include N-hydroxy-2-pyridone (hereinafter, HOPO).

The 3,4-dihydro-3-hydroxy-4-oxo-1,2,3-benzotriazine or the derivative thereof is not particularly limited and may have a substituent on its benzene ring, as long as it does not inhibit amidation reaction. Examples of the 3,4-dihydro-3-hydroxy-4-oxo-1,2,3-benzotriazine or the derivative thereof include 3,4-dihydro-3-hydroxy-4-oxo-1,2,3-benzotriazine, 7-chloro-3,4-dihydro-3-hydroxy-4-oxo-1,2,3-benzotriazine, 3,4-dihydro-3-hydroxy-7-nitro-4-oxo-1,2,3-benzotriazine, and 3,4-dihydro-3-hydroxy-6,7-dimethoxy-4-oxo-1,2,3-benzotriazine.

The N-hydroxypyridine or the derivative thereof is not particularly limited and may have a substituent on its pyridine ring, as long as it does not inhibit amidation reaction. Examples of the N-hydroxypyridine or the derivative thereof include N-hydroxypyridine and 4-(dimethylamino)pyridine-N-oxide.

The ester group of the cyano(hydroxyimino)acetic acid ester may have a substituent that does not inhibit amidation reaction. Examples of the cyano(hydroxyimino)acetic acid ester include a cyano(hydroxyimino)acetic acid alkyl ester and a cyano(hydroxyimino)acetic acid aryl ester.

In the cyano(hydroxyimino)acetic acid alkyl ester, the alkyl ester group moiety may be linear, branched, or cyclic and preferably has an alkyl group having 1 to 10 carbon atoms. The cyano(hydroxyimino)acetic acid alkyl ester is, for instance, methyl cyano(hydroxy-imino)acetate, ethyl cyano(hydroxyimino)acetate, propyl cyano(hydroxyimino)acetate, tert-butyl cyano(hydroxyimino)acetate, benzyl cyano(hydroxyimino)acetate, cyclohexyl cyano(hydroxyimino)acetate, or (2,2-dimethyl-1,3-dioxolan-4-yl)methyl cyano(hydroxyimino)acetate, more preferably ethyl cyano(hydroxyimino)acetate.

In the cyano(hydroxyimino)acetic acid aryl ester, the aryl ester group moiety may have a substituent on the benzene ring, or at least one carbon atom on the benzene ring may be replaced by a nitrogen atom. Examples of the cyano(hydroxyimino)acetic acid aryl ester include phenyl cyano(hydroxyimino)acetate and 1-naphthyl cyano(hydroxyimino)acetate.

The equivalent amount of the carbodiimide-based dehydration condensation agent is preferably 10 to 100 equivalents, more preferably 20 to 40 equivalents, with respect to the first single-stranded oligo-RNA molecule. The equivalent amount of the N-hydroxy nitrogen-containing aromatic compound (e.g., hydroxybenzotriazole or a derivative thereof) or the cyano(hydroxyimino)acetic acid ester is preferably 10 to 100 equivalents, more preferably 20 to 40 equivalents, with respect to the first single-stranded oligo-RNA molecule.

The 2-halopyridinium-based dehydration condensation agent is pyridinium salt having a hydrocarbon substituent on the nitrogen atom of the pyridine ring, and means a compound having halogen at position 2 of the pyridine ring. The pyridine ring may have a substituent at any of positions 3 to 6 of the pyridine ring. The hydrocarbon substituent on the nitrogen atom and the substituent at any of positions 3 to 6 of the pyridine ring are not particularly limited as long as the substituents do not inhibit amidation reaction. Examples of the 2-halopyridinium-based dehydration condensation agent include 2-chloro-1-methylpyridinium, 2-bromo-1-methylpyridinium, 2-fluoro-1-methylpyridinium, 2-chloro-1-ethylpyridinium, 2-bromo-1-ethylpyridinium, 2-fluoro-1-ethylpyridinium, 2-fluoro-1, 3-dimethylpyridinium, 2-chloro-1-methylquinolinium, 2-iodo-1-methylquinolinium, 2-chloro-1-(2-oxo-2-phenethyl)pyridinium, 2-bromo-1-(2-oxo-2-phenethyl)pyridinium, 2-chloro-1-[2-(3-nitrophenyl)-2-oxoethyl]pyridinium, 2-chloro-1-[2-(4-fluorophenyl)-2-oxoethyl]pyridinium, 2-chloro-1-[2-(4-chloro-phenyl)-2-oxoethyl]pyridinium, 2-bromo-1-[2-(4-biphenyl)-2-oxoethyl]pyridinium, 2-bromo-1-[2-(3-nitrophenyl)-2-oxoethyl]pyridinium, 2-bromo-1-[2-(4-methoxyphenyl)-2-oxoethyl]pyridinium, 2-chloro-1-benzylpyridinium, 2-iodo-1-ethyl-6-methoxyquinolinium, and derivatives thereof. Examples of the derivatives include salts such as chloride, bromide, iodide, perchlorate, trifluoromethanesulfonate, tetrafluoroborate, and hexafluorophosphate. The 2-halopyridinium-based dehydration condensation agent may be 2-chloro-1-methylpyridinium salt.

Preferred examples of the 2-halopyridinium-based dehydration condensation agent include 2-chloro-1-methylpyridinium iodide.

The equivalent amount of the 2-halopyridinium-based dehydration condensation agent is preferably 10 to 100 equivalents, more preferably 20 to 40 equivalents, with respect to the first single-stranded oligo-RNA molecule. The equivalent amount of the N-hydroxy nitrogen-containing aromatic compound (e.g., hydroxybenzotriazole or a derivative thereof) is preferably 10 to 100 equivalents, more preferably 20 to 40 equivalents, with respect to the first single-stranded oligo-RNA molecule.

Four substituents on two nitrogen atoms of the formamidinium-based dehydration condensation agent are not particularly limited and these substituents may form a ring together with the nitrogen atoms as long as the substituents do not inhibit amidation reaction. Examples of the formamidinium-based dehydration condensation agent include chloro-N,N,N',N'-tetramethylformamidinium, 2-chloro-1,3-dimethylimidazolinium, chloro-N,N,N',N'-bis(tetramethylene)formamidinium, chloro-N,N,N',N'-bis(pentamethylene)formamidinium, 2-chloro-1,3-dimethyl-4,5-dihydropyrimidinium, fluoro-N,N,N',N'-tetramethylformamidinium, 2-fluoro-1,3-dimethylimidazolinium, fluoro-N,N,N',N'-bis(tetramethylene)formamidinium, and derivatives thereof. Examples of the derivatives include salts such as chloride, bromide, iodide, perchlorate, trifluoromethanesulfonate, tetrafluoroborate, and hexafluorophosphate. The formamidinium-based dehydration condensation agent may be chloro-N,N,N',N'-tetramethylformamidinium salt.

Preferred examples of the formamidinium-based dehydration condensation agent include chloro-N,N,N',N'-tetramethylformamidinium hexafluorophosphate (hereinafter, TCFH).

The N-hydrocarbon-substituted imidazole derivative means a compound having a hydrocarbon substituent on a nitrogen atom of the imidazole structure. The imidazole structure may have a substituent on position 2, 4 or 5 of the imidazole ring. The hydrocarbon substituent and the substituent on position 2, 4 or 5 of the imidazole ring are not particularly limited as long as the substituents do not inhibit amidation reaction. Examples of the N-hydrocarbon-substituted imidazole derivative include N-alkylimidazole derivatives and N-arylimidazole derivatives.

The N-alkylimidazole derivative is not particularly limited and may have a substituent on its imidazole ring, as long as the derivative does not inhibit amidation reaction. Examples of the N-alkylimidazole derivative include N-methylimidazole (hereinafter, NMI) and 1,2-dimethylimidazole.

The N-arylimidazole derivative is not particularly limited and may have a substituent on its imidazole ring, as long as the derivative does not inhibit amidation reaction. Examples of the N-arylimidazole derivative include N-phenylimidazole and 1-phenyl-2-methylimidazole.

The equivalent amount of the formamidinium-based dehydration condensation agent is preferably 10 to 100 equivalents, more preferably 20 to 40 equivalents, with respect to the first single-stranded oligo-RNA molecule. The equivalent amount of the N-hydroxy nitrogen-containing aromatic compound (e.g., hydroxybenzotriazole or a derivative thereof) or the N-hydrocarbon-substituted imidazole derivative is preferably 10 to 100 equivalents, more preferably 20 to 40 equivalents, with respect to the first single-stranded oligo-RNA molecule.

The dehydration condensation agent and the N-hydroxy nitrogen-containing aromatic compound, the cyano(hydroxyimino)acetic acid ester and the N-hydrocarbon-substituted imidazole derivative may adopt commercially available products or may be synthesized by known methods or methods equivalent thereto.

In one example, to the first single-stranded oligo-RNA molecule and the second single-stranded oligo-RNA molecule, the dehydration condensation agent, specifically, the triazine-based dehydration condensation agent, the uronium-based dehydration condensation agent comprising an N-hydroxy nitrogen-containing aromatic ring structure (e.g., a benzotriazolyluronium-based dehydration condensation agent), the carbodiimide-based dehydration condensation agent, the 2-halopyridinium-based dehydration condensation agent or the formamidinium-based dehydration condensation agent, may be added as a solid or may be dissolved or suspended in a solution such as water, a buffer solution, a hydrophilic organic solvent or a mixed solvent thereof, or the like and then added. In using the carbodiimide-based dehydration condensation agent in combination with the N-hydroxy nitrogen-containing aromatic compound (e.g., hydroxybenzotriazole or a derivative thereof) or the cyano(hydroxyimino)acetic acid ester, either of the carbodiimide-based dehydration condensation agent or the N-hydroxy nitrogen-containing aromatic compound (e.g., hydroxybenzotriazole or a derivative thereof) or the cyano(hydroxyimino)acetic acid ester may be added first, or both of them may be added at the same time. In using the 2-halopyridinium-based dehydration condensation agent in combination with the N-hydroxy nitrogen-containing aromatic compound, either of the 2-halopyridinium-based dehydration condensation agent or the N-hydroxy nitrogen-containing aromatic compound may be added first, or both of them may be added at the same time. In using the formamidinium-based dehydration condensation agent in combination with the N-hydroxy nitrogen-containing aromatic compound or the N-hydrocarbon-substituted imidazole derivative, either of the formamidinium-based dehydration condensation agent or the N-hydroxy nitrogen-containing aromatic compound or the N-hydrocarbon-substituted imidazole derivative may be added first, or both of them may be added at the same time.

Alternatively, the first single-stranded oligo-RNA molecule and the second single-stranded oligo-RNA molecule may be added to the dehydration condensation agent, specifically, the triazine-based dehydration condensation agent, the uronium-based dehydration condensation agent comprising an N-hydroxy nitrogen-containing aromatic ring structure (e.g., a benzotriazol-yluronium-based dehydration condensation agent), the carbodiimide-based dehydration condensation agent, the 2-halopyridinium-based dehydration condensation agent or the formamidinium-based dehydration condensation agent. In this respect, either of the first single-stranded oligo-RNA molecule or the second single-stranded oligo-RNA molecule may be added first, or both of them may be added at the same time. The first single-stranded oligo-RNA molecule and the second single-stranded oligo-RNA molecule may be added as a solid or may be dissolved or suspended in water, a buffer solution, a hydrophilic organic solvent or a mixed solvent thereof, or the like and then added. Usually, it is preferred to add the dehydration condensation agent to a solution of the first single-stranded oligo-RNA molecule and the second single-stranded oligo-RNA molecule. In using the carbodiimide-based dehydration condensation agent in combination with the N-hydroxy nitrogen-containing aromatic compound or the cyano(hydroxyimino)acetic acid ester, the first single-stranded oligo-RNA molecule and the second single-stranded oligo-RNA molecule may be added to the carbodiimide-based dehydration condensation agent and the N-hydroxy nitrogen-containing aromatic compound or the cyano(hydroxyimino)acetic acid ester. In this respect, either of the first single-stranded oligo-RNA molecule or the second single-stranded oligo-RNA molecule may be added first, or both of them may be added at the same time. The first single-stranded oligo-RNA molecule and the second single-stranded oligo-RNA molecule may be added as a solid or may be dissolved or suspended in water, a buffer solution, a hydrophilic organic solvent or a mixed solvent thereof or the like and then added. Usually, it is preferred to add the dehydration condensation agent to a solution of the first single-stranded oligo-RNA molecule and the second single-stranded oligo-RNA molecule. In using the 2-halopyridinium-based dehydration condensation agent in combination with the N-hydroxy nitrogen-containing aromatic compound, the first single-stranded oligo-RNA molecule and the second single-stranded oligo-RNA molecule may be added to the 2-halopyridinium-based dehydration condensation agent and the N-hydroxy nitrogen-containing aromatic compound. In this respect, either of the first single-stranded oligo-RNA molecule or the second single-stranded oligo-RNA molecule may be added first, or both of them may be added at the same time. The first single-stranded oligo-RNA molecule and the second single-stranded oligo-RNA molecule may be added as a solid or may be dissolved or suspended in water, a buffer solution, a hydrophilic organic solvent or a mixed solvent thereof, or the like and then added. Usually, it is preferred to add the dehydration condensation agent to a solution of the first single-stranded oligo-RNA molecule and the second single-stranded oligo-RNA molecule. In using the formamidinium-based dehydration condensation agent in combination with the N-hydroxy nitrogen-containing aromatic compound or the N-hydrocarbon-substituted imidazole derivative, the first single-stranded oligo-RNA molecule and the second single-stranded oligo-RNA molecule may be added to the formamidinium-based dehydration condensation agent and the N-hydroxy nitrogen-containing aromatic compound or the N-hydrocarbon-substituted imidazole derivative. In this respect, either of the first single-stranded oligo-RNA molecule or the second single-stranded oligo-RNA molecule may be added first, or both of them may be added at the same time. The first single-stranded oligo-RNA molecule and the second single-stranded oligo-RNA molecule may be added as a solid or may be dissolved or suspended in water, a buffer solution, a hydrophilic organic solvent or a mixed solvent thereof or the like and then added. Usually, it is preferred to add the dehydration condensation agent to a solution of the first single-stranded oligo-RNA molecule and the second single-stranded oligo-RNA molecule.

The dehydration condensation agent is preferably 4-(4,6-dimethoxy-1,3,5-triazin-2-yl)-4-methylmorpholinium salt, 0-(7-azabenzotriazol-1-yl)-N,N,N',N'-tetramethyluronium salt, N-(3'-dimethylaminopropyl)-N'-ethylcarbodiimide or a salt thereof, 2-chloro-1-methylpyridinium salt or chloro-N,N,N',N'-tetramethylformamidinium salt, more preferably 4-(4,6-dimethoxy-1,3,5-triazin-2-yl)-4-methylmorpholinium chloride, 0-(7-azabenzotriazol-1-yl)-N,N,N',N'-tetramethyluronium hexafluorophosphate, N-(3'-dimethylaminopropyl)-N'-ethylcarbodiimide hydrochloride, 2-chloro-1-methylpyridinium iodide, or chloro-N,N,N',N'-tetramethylformamidinium hexafluorophosphate.

The N-hydroxy nitrogen-containing aromatic compound for use with the carbodiimide-based dehydration condensation agent, the 2-halopyridinium-based dehydration condensation agent, or the formamidinium-based dehydration condensation agent as the dehydration condensation agent is preferably hydroxybenzotriazole or a derivative thereof, more preferably hydroxyazabenzotriazole or a derivative thereof, further preferably 1-hydroxy-7-azabenzotriazole.

The cyano(hydroxyimino)acetic acid ester for use with the carbodiimide-based dehydration condensation agent as the dehydration condensation agent is preferably a cyano(hydroxyimino)acetic acid alkyl ester, more preferably ethyl cyano(hydroxyimino)acetate.

The N-hydrocarbon-substituted imidazole derivative for use with the formamidinium-based dehydration condensation agent as the dehydration condensation agent is preferably N-alkylimidazole derivative, more preferably N-methylimidazole.

The dehydration condensation agent may comprise at least the triazine-based dehydration condensation agent, the uronium-based dehydration condensation agent comprising an N-hydroxy nitrogen-containing aromatic ring structure (e.g., a benzotriazolyluronium-based dehydration condensation agent), the carbodiimide-based dehydration condensation agent, the 2-halopyridinium-based dehydration condensation agent or the formamidinium-based dehydration condensation agent, or two or more types thereof may be mixed. In adding the dehydration condensation agent or the N-hydroxy nitrogen-containing aromatic compound (e.g., hydroxybenzotriazole or a derivative thereof), the cyano(hydroxyimino)acetic acid ester, or the N-hydrocarbon-substituted imidazole derivative dissolved or suspended in a solution such as water, a buffer solution or a hydrophilic organic solvent, the solution containing the dehydration condensation agent, the N-hydroxy nitrogen-containing aromatic compound (e.g., hydroxybenzotriazole or a derivative thereof), the cyano(hydroxyimino)acetic acid ester, or the N-hydro-carbon-substituted imidazole derivative partly constitutes the reaction solvent (mixed solvent).

A preferred example of the dehydration condensation agent, a preferred example of the N-hydroxy nitrogen-containing aromatic compound (e.g., hydroxybenzotriazole or a derivative thereof), the cyano(hydroxyimino)acetic acid ester or the N-hydrocarbon-substituted imidazole derivative, and a preferred example of the hydrophilic organic solvent can be optionally combined. Examples of such a combination include a combination of DMT-MM and DMSO, a combination of HATU and DMSO, a combination of HATU and DMF, a combination of EDCI hydrochloride, HOAt and DMSO, a combination of EDCI hydrochloride, ethyl cyano(hydroxyi-mino)acetate and DMSO, a combination of 2-chloro-1-methylpyridinium iodide, HOAt and DMSO, a combination of chloro-N,N,N',N'-tetramethylformamidinium hexafluorophosphate, HOAt and DMSO, and a combination of chloro-N,N,N',N'-tetramethylformamidinium hexafluorophosphate, N-methylimidazole and DMSO. In a particularly preferred example, examples of the combination include a combination of HATU and DMSO, a combination of HATU and DMF, a combination of EDCI hydrochloride, HOAt and DMSO, and a combination of chloro-N,N,N',N'-tetramethylformamidinium hexafluorophosphate, HOAt and DMSO.

The pH of the reaction solvent (mixed solvent) can be appropriately adjusted and is preferably 6.5 to 7.5, more preferably 6.9 to 7.5, for instance, 6.5 to 7.0, 6.9 to 7.1, or 7.0 to 7.5.

The time for the reaction (amidation reaction) of the first single-stranded oligo-RNA molecule with the second single-stranded oligo-RNA molecule can be appropriately set and may be typically 1 hour or longer, for instance, 1 to 48 hours or 1 to 24 hours.

In one example, the first single-stranded oligo-RNA molecule and the second single-stranded oligo-RNA molecule may be mixed at equal molar quantity. The phrase "mixed at equal molar quantity" means that the first single-stranded oligo-RNA molecule and the second single-stranded oligo-RNA molecule are mixed at a molar ratio of 1:1.1 to 1.1:1. The hairpin single-stranded RNA molecule containing a gene expression-inhibiting sequence formed in the amidation reaction solution (reaction solvent) can be purified by a known method. Examples of the purification technique include, but are not limited to, chromatography such as reverse phase chromatography, reverse phase high performance liquid chromatography (RP-HPLC), ultra-high performance liquid chromatography (UHPLC), and ion exchange chromatography, gel filtration, column purification, polyacrylamide gel electrophoresis (PAGE), and any combination thereof.

In the procedure described in WO '919, nucleic acid impurities such as short-strand nucleic acid impurities and truncated products may be generated due to early termination of an elongation reaction during the stage of a very short strand, thereby causing a decrease in purity of a product of interest in the reaction solution. By contrast, our method has an advantage from the viewpoint of being able to decrease nucleic acid impurities. Preferably, our method can produce a highly stable single-stranded RNA molecule capable of inhibiting gene expression by using general-purpose RNA amidites while decreasing the generation of nucleic acid impurities.

The hairpin single-stranded RNA molecule produced by our method can be used and administered in vivo or intracellularly to inhibit expression of a target gene by conventional methods.

The preferred examples described above, for instance, the first single-stranded oligo-RNA molecule, the second single-stranded oligo-RNA molecule, the buffer solution, the organic solvent, the dehydration condensation agent, the pH, the ratio of the organic solvent, the reaction time, the amount of use, other reaction conditions and the like can be optionally combined.

We also provide a single-stranded oligo-RNA molecule that can be used as a second single-stranded oligo-RNA molecule for producing a hairpin single-stranded RNA molecule according to our method.

Examples of the single-stranded oligo-RNA molecule used for the production of a hairpin single-stranded RNA molecule capable of inhibiting expression of TGF-β1 gene or GAPDH gene serving as a target gene include, but are not limited to (a) and (b):

(a) a single-stranded oligo-RNA molecule comprising the nucleotide sequence set forth in SEQ ID NO: 3 in which a ribonucleotide residue at position 1 is linked to $Lx^2$, and ribonucleotide residues at positions 26 and 27 are linked via Ly;

(b) a single-stranded oligo-RNA molecule comprising the nucleotide sequence set forth in SEQ ID NO: 6 in which a ribonucleotide residue at position 1 is linked to $Lx^2$, and ribonucleotide residues at positions 26 and 27 are linked via Ly.

We further provide a kit for producing a hairpin single-stranded RNA molecule for inhibiting expression of a target gene, comprising a combination (pair) of the single-stranded oligo-RNA molecules. Such a kit can be suitably used for carrying out the method of producing a hairpin single-stranded RNA molecule capable of inhibiting expression of a target gene.

Examples of the kit include, but are not limited to, a kit for producing a hairpin single-stranded RNA molecule of inhibiting expression of TGF-β1 gene or GAPDH gene, comprising a combination of single-stranded oligo-RNA molecules which is (1) or (2):

(1) a combination of a first single-stranded oligo-RNA molecule comprising the nucleotide sequence set forth in SEQ ID NO: 2 in which a ribonucleotide residue at position 24 is linked to $Lx^1$, and a second single-stranded oligo-RNA molecule comprising the nucleotide sequence set forth in SEQ ID NO: 3 in which a ribonucleotide residue at position 1 is linked to $Lx^2$, and ribonucleotide residues at positions 26 and 27 are linked via Ly;

(2) a combination of a first single-stranded oligo-RNA molecule comprising the nucleotide sequence set forth in SEQ ID NO: 5 in which a ribonucleotide residue at position 22 is linked to $Lx^1$, and a second single-stranded oligo-RNA molecule comprising the nucleotide sequence set forth in SEQ ID NO: 6 in which a ribonucleotide residue at position 1 is linked to $Lx^2$, and ribonucleotide residues at positions 26 and 27 are linked via Ly.

EXAMPLES

Hereinafter, our methods, molecules and kits will be described further specifically with reference to Examples. In this regard, however, the technical scope of this disclosure is not limited by the Examples.

Reference Example 1

Synthesis of Proline Diamido Amidite

A proline diamido amidite can be synthesized in accordance with the descriptions of, for instance, WO 2012/017919. Specific synthesis examples will be illustrated below, but the synthesis scheme is not limited to them:

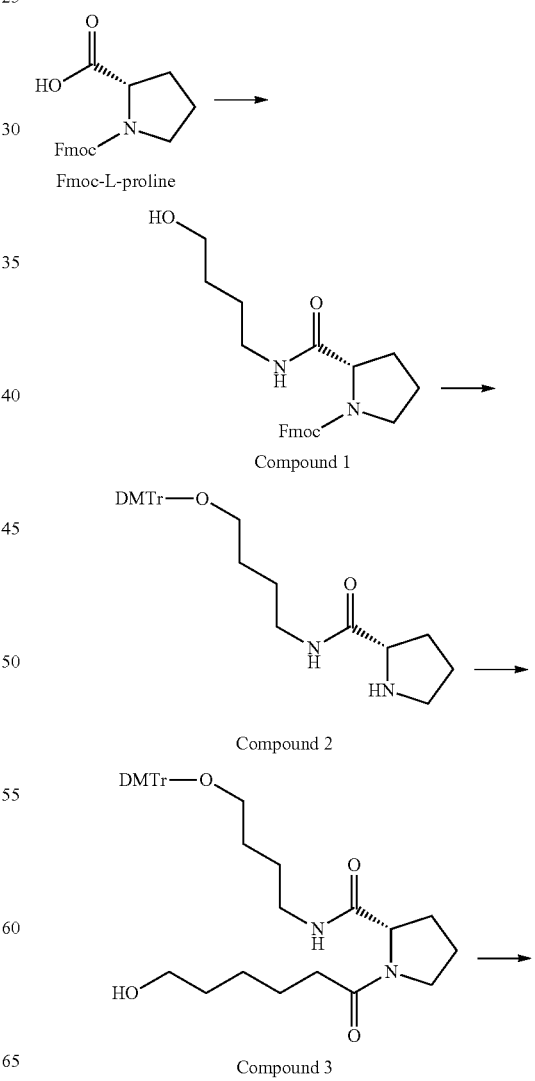

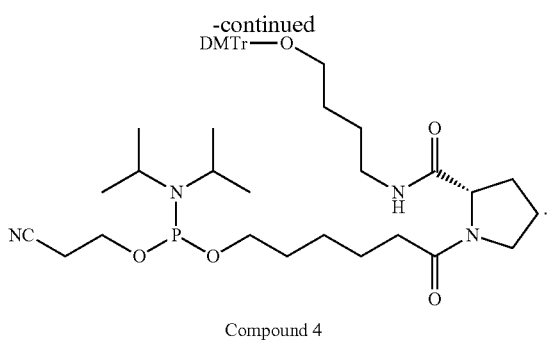

Compound 4

(1) Fmoc-hydroxyamido-L-proline (Compound 1)

Fmoc-L-proline (10.00 g, 29.64 mmol), 4-amino-1-butanol (3.18 g, 35.56 mmol) and 1-hydroxybenzotriazole (10.90 g, 70.72 mmol) were mixed. The mixture was degassed under reduced pressure and charged with argon gas. To the obtained mixture, anhydrous acetonitrile (140 mL) was added at room temperature, and further, a solution of dicyclohexylcarbodiimide (7.34 g, 35.56 mmol) in anhydrous acetonitrile (70 mL) was added. Then, the mixture was stirred under an argon atmosphere at room temperature for 15 hours. After the end of the reaction, the resulting precipitate was filtered off. Regarding a filtrate collected, the solvent was distilled away under reduced pressure. Dichloromethane (200 mL) was added to the obtained residue, which was then washed with saturated sodium bicarbonate water (200 mL). Then, the organic layer was collected, dried over magnesium sulfate, and then filtered. Regarding a filtrate collected, the solvent was distilled away under reduced pressure. Diethyl ether (200 mL) was added to the residue, which was then pulverized. The resulting powder was separated by filtration to produce Fmoc-hydroxyamido-L-proline as a colorless powdered substance. Fmoc refers to a 9-fluorenylmethyloxycarbonyl group.

(2) DMTr-amido-L-proline (Compound 2)

Fmoc-hydroxyamido-L-proline (7.80 g, 19.09 mmol) and anhydrous pyridine (5 mL) were mixed, azeotropically dried twice at room temperature. To the obtained residue, 4,4'-dimethoxytrityl chloride (8.20 g, 24.20 mmol), 4-dimethylaminopyridine (23 mg, 0.19 mmol) and anhydrous pyridine (39 mL) were added. This mixture was stirred at room temperature for 1 hour. Then, methanol (7.8 mL) was added, and the mixture was stirred at room temperature for 30 minutes. This mixture was diluted with dichloromethane (100 mL) and washed with saturated sodium bicarbonate water (150 mL), followed by separation of an organic layer. This organic layer was dried over sodium sulfate and then filtered. The solvent in the obtained filtrate was distilled away under reduced pressure. To the obtained unpurified residue, anhydrous N,N-dimethylformamide (39 mL) and piperidine (18.7 mL, 189 mmol) were added, and the mixture was stirred at room temperature for 1 hour. After the end of the reaction, the solvent was distilled away from the mixed liquid under reduced pressure at room temperature. The obtained residue was subjected to silica gel column chromatography (trade name: Wakogel C-300, eluent, dichloromethane:methanol=9:1, containing 0.05% pyridine) to obtain DMTr-amido-L-proline as a pale yellow oily substance. DMTr refers to a 4,4'-dimethoxytrityl group.

(3) DMTr-hydroxydiamido-L-proline (Compound 3)

The above obtained DMTr-amido-L-proline (6.01 g, 12.28 mmol), N-(3'-dimethylaminopropyl)-N'-ethylcarbodiimide (2.83 g, 14.74 mmol), 1-hydroxybenzotriazole (3.98 g, 29.47 mmol) and triethylamine (4.47 g, 44.21 mmol) were mixed in an anhydrous dichloromethane solution (120 mL). Further, 6-hydroxy hexanoic acid (1.95 g, 14.47 mmol) was added to the mixed liquid under an argon atmosphere at room temperature, and the mixture was then stirred under an argon atmosphere at room temperature for 1 hour. The obtained mixed liquid was diluted with dichloromethane (600 mL) and washed with saturated saline (800 mL) three times. The organic layer was collected, dried over sodium sulfate, and then filtered. The solvent in the obtained filtrate was distilled away under reduced pressure. This yielded DMTr-hydroxydiamido-L-proline as a pale yellow foamed substance.

(4) DMTr-diamido-L-proline amidite (Compound 4)

The obtained DMTr-hydroxydiamido-L-proline (8.55 g, 14.18 mmol) and anhydrous acetonitrile were mixed, azeotropically dried three times at room temperature. To the obtained residue, diisopropyl ammonium tetrazolide (2.91 g, 17.02 mmol) was added, and the mixture was degassed under reduced pressure and charged with argon gas. To the mixture, anhydrous acetonitrile (10 mL) was added, and further, a solution of 2-cyanoethoxy-N,N,N',N'-tetraisopropylphosphorodiamidite (5.13 g, 17.02 mmol) in anhydrous acetonitrile (7 mL) was added. This mixture was stirred under an argon atmosphere at room temperature for 2 hours. The obtained mixture was diluted with dichloromethane, washed with saturated sodium bicarbonate water (200 mL) three times, and then washed with saturated saline (200 mL). The organic layer was collected, dried over sodium sulfate, and then filtered. The solvent in the obtained filtrate was distilled away under reduced pressure. The obtained residue was subjected to column chromatography using amino silica gel as a filler (eluent, hexane:ethyl acetate=1:3, containing 0.05% pyridine) to obtain DMTr-diamido-L-proline amidite as a colorless syrup-like substance.

Example 1

1. Synthesis of Proline Ester Amidite (Cyanoethyl-Protected)

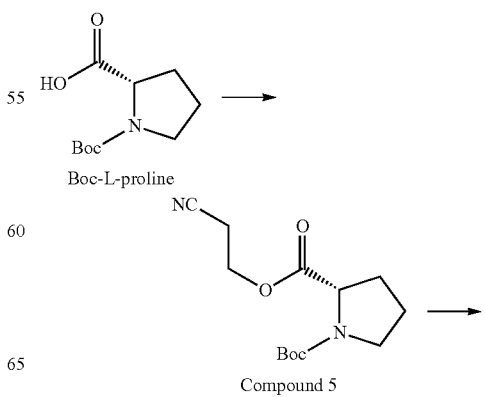

Boc-L-proline

Compound 5

47

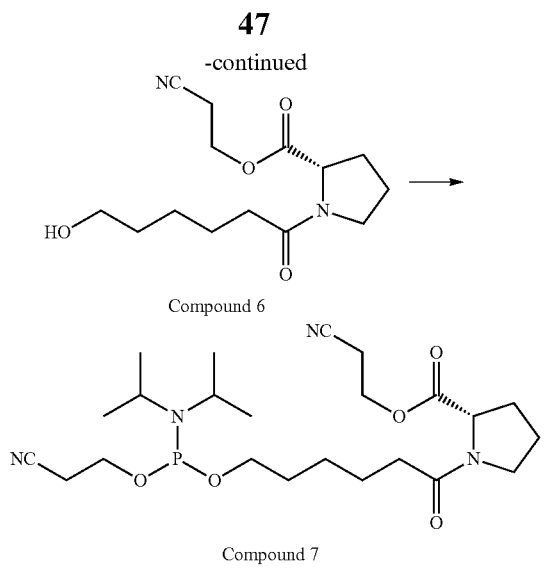

Compound 6

Compound 7

(1) Boc-L-proline-cyanoethyl ester (Compound 5)

Boc-L-proline (10.00 g, 46.46 mmol) and 2-cyanoethanol (3.96 g, 55.75 mmol) were mixed. To the mixture, dichloromethane (100 mL) was added at room temperature, and the resulting mixture was cooled in an ice bath. After addition of N-(3'-dimethylaminopropyl)-N'-ethylcarbodiimide hydrochloride (9.80 g, 51.10 mmol) and 4-dimethylaminopyridine (1.12 g, 9.29 mmol), the ice bath was removed, and the mixture was stirred under an argon atmosphere at room temperature for 3 hours. The obtained mixed liquid was washed with distilled water (100 mL). The organic layer was collected, dried over sodium sulfate, and then filtered. The solvent in the obtained filtrate was distilled away under reduced pressure. The obtained residue was subjected to silica gel column chromatography (eluent, chloroform:methanol=19:1) to obtain Boc-L-proline-cyanoethyl ester (12.47 g, yield: 100%) as an oily substance. Boc refers to a butoxycarbonyl group.

(2) N-Amido-L-proline-cyanoethyl ester (Compound 6)

Boc-L-proline-cyanoethyl ester (12.47 g, 46.46 mmol) and dioxane (29 mL) were mixed. To the obtained mixture, a 4 M solution of hydrogen chloride in dioxane (44 mL) was added, and this mixture was stirred at room temperature for 2 hours. Then, the solvent was distilled away under reduced pressure. To the obtained unpurified residue, dichloromethane (90 mL) was added. To this mixture, 6-hydroxy hexanoic acid (8.09 g, 61.20 mmol) and triethylamine (9.40 g, 92.91 mmol) were added, and the resulting mixture was cooled in an ice bath. After addition of EDCI hydrochloride (9.80 g, 51.10 mmol), the ice bath was removed, and the mixture was stirred at room temperature for 4 hours. The obtained mixed liquid was washed with distilled water (100 mL). The organic layer was collected, dried over sodium sulfate, and then filtered. The solvent in the obtained filtrate was distilled away under reduced pressure. The obtained residue was subjected to silica gel column chromatography

48

(eluent, chloroform:methanol=9:1) to obtain N-amido-L-proline-cyanoethyl ester (10.16 g, yield: 77%) as an oily substance.

(3) Cyanoethyl-L-proline amidite (Compound 7)

The obtained N-amido-L-proline-cyanoethyl ester (5.00 g, 17.71 mmol) and anhydrous acetonitrile (40 mL) were mixed. The mixture was degassed under reduced pressure and charged with argon gas. To the mixture, tetrazole (1.49 g, 21.25 mmol) and diisopropylamine (2.15 g, 21.25 mmol) were added, and further, a solution of 2-cyanoethoxy-N,N,N',N'-tetraisopropylphosphorodiamidite (6.41 g, 21.25 mmol) in anhydrous acetonitrile (10 mL) was added. This mixture was stirred under an argon atmosphere at room temperature for 3 hours. The obtained mixture was diluted with dichloromethane (100 mL) and washed with a 5% aqueous sodium bicarbonate solution (100 mL). The organic layer was collected, dried over sodium sulfate, and then filtered. The solvent in the obtained filtrate was distilled away under reduced pressure. The obtained residue was subjected to column chromatography using amino silica gel as a filler (eluent, hexane:ethyl acetate=1:4) to obtain cyanoethyl-L-proline amidite (7.03 g, yield: 82%) as an oily substance.

2. Synthesis of Proline Ester Amidite (2,4-dimethoxybenzyl-protected)

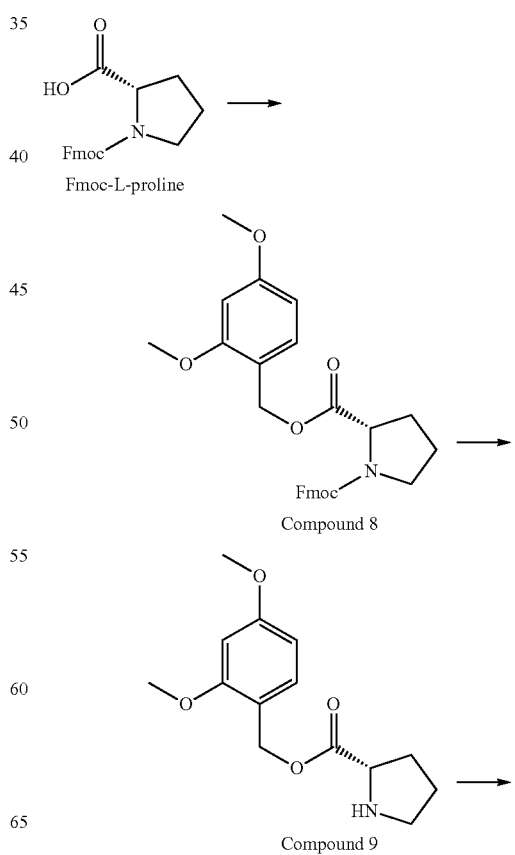

Fmoc-L-proline

Compound 8

Compound 9

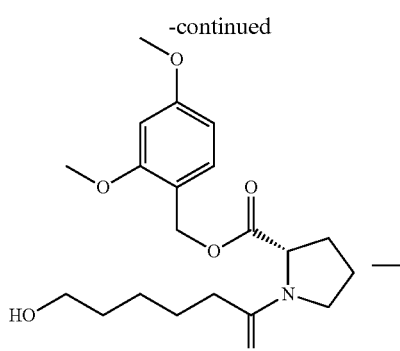

Compound 10

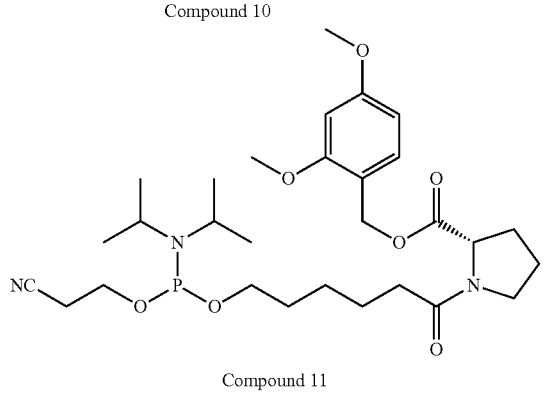

Compound 11

(1) Fmoc-L-proline-(2,4-dimethoxy)benzyl ester (Compound 8)

Fmoc-L-proline (12.04 g, 35.67 mmol) and 2,4-dimethoxybenzyl alcohol (5.00 g, 29.73 mmol) were mixed. To the mixture, dichloromethane (100 mL) was added at room temperature. EDCI hydrochloride (6.84 g, 35.67 mmol) and 4-dimethylaminopyridine (0.36 g, 2.97 mmol) were added thereto, and then, the mixture was stirred at room temperature for 3 hours. The obtained mixed liquid was washed with distilled water (100 mL). The organic layer was collected, dried over sodium sulfate, and then filtered. The solvent in the obtained filtrate was distilled away under reduced pressure. The obtained residue was subjected to silica gel column chromatography (eluent, hexane:ethyl acetate=3:2) to obtain Fmoc-L-proline-(2,4-dimeth-oxy)benzyl ester (13.24 g, yield: 91%). Fmoc refers to a fluorenylmethyloxycarbonyl group.

(2) L-proline-(2,4-dimethoxy)benzyl ester (Compound 9)

Fmoc-L-proline-(2,4-dimethoxy)benzyl ester (13.24 g, 27.16 mmol) and dichloromethane (130 mL) were mixed. To the obtained mixture, diazabicycloundecene (4.96 g, 32.59 mmol) was added, and this mixture stirred at room temperature for 1 hour. Then, the solvent was distilled away under reduced pressure. The obtained residue was subjected to silica gel column chromatography (eluent, chloroform:methanol=9:1) to obtain L-proline-(2,4-dimethoxy)benzyl ester (6.39 g, yield: 89%) as an oily substance.

(3) N-Amido-L-proline-(2,4-dimethoxy)benzyl ester (Compound 10)

L-Proline-(2,4-dimethoxy)benzyl ester (6.39 g, 24.09 mmol) and dichloromethane (120 mL) were mixed. To this mixture, 6-hydroxy hexanoic acid (3.82 g, 28.90 mmol) and triethylamine (4.87 g, 48.17 mmol) were added. EDCI hydrochloride (5.54 g, 28.90 mmol) was added thereto, and then, the mixture was stirred at room temperature for 16 hours. The obtained mixed liquid was washed with distilled water (100 mL). The organic layer was collected, dried over sodium sulfate, and then filtered. The solvent in the obtained filtrate was distilled away under reduced pressure. The obtained residue was subjected to silica gel column chromatography (eluent, ethyl acetate:methanol=9:1) to obtain N-amido-L-proline-(2,4-dimethoxy)benzyl ester (5.22 g, yield: 57%) as an oily substance.

(4) (2,4-Dimethoxy)benzyl-L-proline amidite (Compound 11)

N-Amido-L-proline-(2,4-dimethoxy)benzyl ester (2.00 g, 5.27 mmol) and anhydrous acetonitrile (27 mL) were mixed. The mixture was degassed under reduced pressure and charged with argon gas. To the mixture, tetrazole (0.44 g, 6.32 mmol) and diisopropylamine (0.64 g, 6.32 mmol) were added, and further, 2-cyanoethoxy-N,N,N',N'-tetraisopropylphosphorodiamidite (1.91 g, 6.32 mmol) was added. This mixture was stirred under an argon atmosphere at room temperature for 23 hours. The obtained mixture was diluted with chloroform (60 mL) and washed with a 5% aqueous sodium bicarbonate solution (60 mL). The organic layer was collected, dried over sodium sulfate, and then filtered. The solvent in the obtained filtrate was distilled away under reduced pressure. The obtained residue was subjected to column chromatography using amino silica gel as a filler (eluent, hexane:ethyl acetate=1:4) to obtain (2,4-dimethoxy)benzyl-L-proline amidite (2.27 g, yield: 74%) as an oily substance.

Reference Example 2

Synthesis of Glycine Diamido Amidite

Glycine diamido amidite can be synthesized in accordance with the descriptions of, for instance, WO 2013/103146. Specific synthesis examples will be illustrated below, but the synthesis scheme is not limited to them.

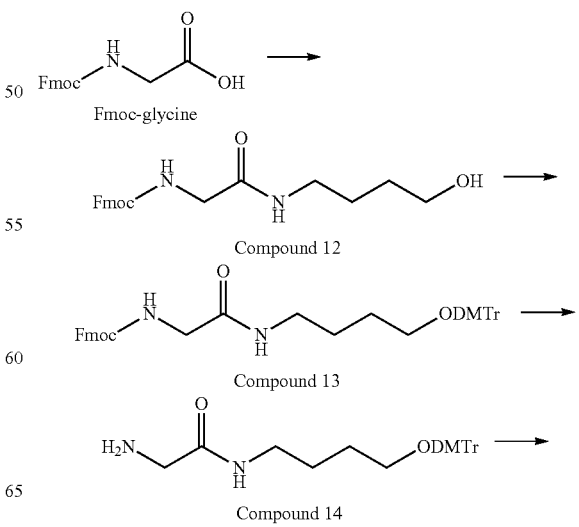

-continued

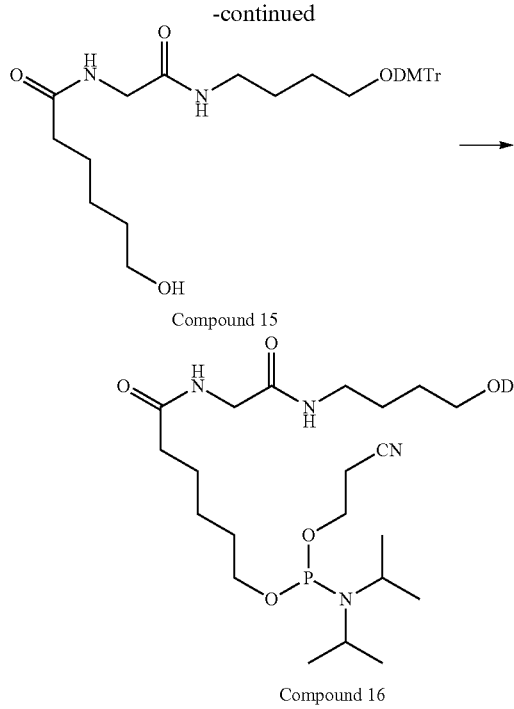

Compound 15

Compound 16

(1) Fmoc-hydroxyamido-glycine (Compound 12)

To a solution of Fmoc-glycine (4.00 g, 13.45 mmol), dicyclohexylcarbodiimide (3.33 g, 16.15 mmol) and 1-hydroxybenzotriazole monohydrate (4.94 g, 32.29 mmol) in anhydrous N,N-dimethylformamide (100 mL), a solution of 4-aminobutanol (1.44 g, 16.15 mmol) in anhydrous N,N-dimethylformamide (30 mL) was added, and the mixture was stirred overnight under an argon atmosphere at room temperature. The resulting precipitate was filtered off, and the filtrate was concentrated under reduced pressure. Dichloromethane (200 mL) was added to the obtained residue, which was then washed with saturated sodium bicarbonate water three times and further washed with saturated saline. After drying over sodium sulfate, the solvent was distilled away under reduced pressure. The obtained residue was subjected to silica gel column chromatography (eluent, dichloromethane-methanol (95:5)) to obtain Fmoc-hydroxyamido-glycine (4.30 g, 87%).

(2) Fmoc-DMTr-amido-glycine (Compound 13)

Compound 12 (4.20 g, 11.40 mmol) was azeotropically dried using anhydrous pyridine three times. To the azeotropic residue, 4,4'-dimethoxytrityl chloride (5.80 g, 17.10 mmol) and anhydrous pyridine (80 mL) were added, and the mixture was stirred overnight at room temperature. To the obtained reaction mixture, methanol (20 mL) was added, and the mixture was stirred at room temperature for 30 minutes. Then, the solvent was distilled away under reduced pressure. Then, dichloromethane (200 mL) was added to the residue, which was then washed with saturated sodium bicarbonate water three times and further washed with saturated saline. After drying over sodium sulfate, the solvent was distilled away under reduced pressure. Unpurified Fmoc-DMTr-amido-glycine (11.40 g) was obtained.

(3) DMTr-amido-glycine (Compound 14)

To unpurified compound 13 (11.40 g, 16.99 mmol), N,N-dimethylformamide (45 mL) and piperidine (11.7 mL) were added at room temperature, and the mixture was stirred overnight at room temperature. The solvent was distilled away from the reaction mixture under reduced pressure. The obtained residue was subjected to silica gel column chromatography (eluent, dichloromethane-methanol (9:1)+ 0.05% pyridine) to obtain DMTr-amido-glycine (4.90 g, 96%, 2 steps).

(4) DMTr-hydroxydiamido-glycine (Compound 15)

Compound 14 (4.80 g, 10.70 mmol) was azeotropically dried with anhydrous pyridine three times. Then, 6-hydroxy hexanoic acid (1.70 g, 12.84 mmol), 1-ethyl-3-(3-dimethyl-amino-propyl)carbodiimide hydrochloride (2.46 g, 12.84 mmol), 1-hydroxybenzotriazole monohydrate (3.93 g, 25.69 mmol), and anhydrous dichloromethane (60 mL) were added thereto under an argon atmosphere at room temperature, and the mixture was stirred for 10 minutes. To the mixture thus obtained, triethylamine (3.90 g, 38.53 mmol) was added, and the resulting mixture was stirred overnight under an argon atmosphere at room temperature. Dichloromethane (200 mL) was added to the obtained reaction mixture, which was then washed with saturated sodium bicarbonate water three times and further with saturated saline once. The organic layer was separated and dried over sodium sulfate. Then, the solvent was distilled away under reduced pressure. The obtained residue was subjected to silica gel column chromatography (eluent, dichloromethane-methanol (95:5)+0.05% pyridine) to obtain DMTr-hydroxydiamido-glycine (4.80 g, 80%).

(5) DMTr-diamido-glycine amidite (Compound 16)

Compound 15 (4.70 g, 8.35 mmol) was azeotropically dried with anhydrous pyridine three times. Next, diisopropyl ammonium tetrazolide (1.72 g, 10.02 mmol) was added thereto, and the mixture was degassed under reduced pressure and charged with argon gas. Anhydrous acetonitrile (5 mL) was added thereto. Further, a solution of 2-cyanoethoxy-N,N,N',N'-tetraisopropylphosphorodiamidite (3.02 g, 10.02 mmol) in a mixed solvent of anhydrous acetonitrile and dichloromethane (1:1) (4 mL) was added thereto, and the mixture was stirred under an argon atmosphere at room temperature for 4 hours. Dichloromethane (150 mL) was added to the obtained reaction mixture, which was then washed with saturated sodium bicarbonate water twice and further with saturated saline once. The organic layer was separated and dried over sodium sulfate. Then, the solvent was distilled away under reduced pressure. The residue was subjected to column chromatography using amino silica (eluent, n-hexane-acetone (3:2)+0.1% triethylamine) to obtain DMTr-diamido-glycine amidite (4.50 g, 71%, HPLC 98.2%).

Example 2

Synthesis of Glycine Ester Amidite (Cyanoethyl-Protected)

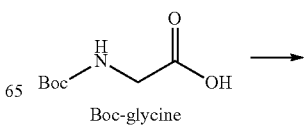

Boc-glycine

-continued

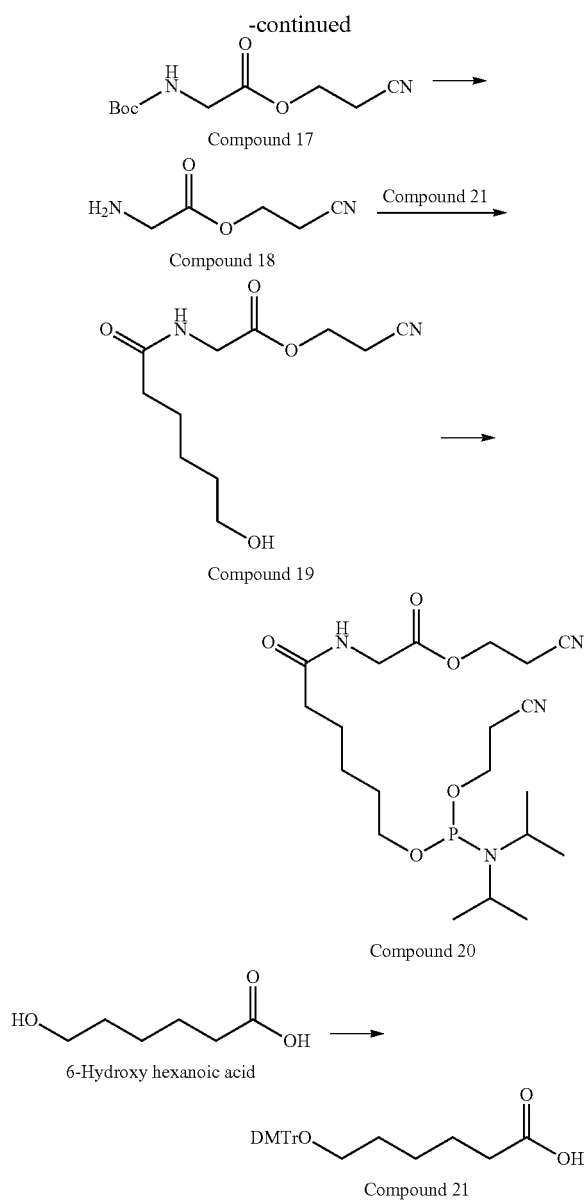

(1) Boc-glycine-cyanoethyl ester (Compound 17)

Boc-glycine (5.00 g, 28.54 mmol) and 2-cyanoethanol (2.40 g, 33.76 mmol) were mixed. To the mixture, dichloromethane (50 mL) was added at room temperature, and the resulting mixture was cooled in an ice bath. After addition of N-(3'-dimethylaminopropyl)-N'-ethylcarbodiimide hydrochloride (EDC) (6.00 g, 31.30 mmol) and 4-dimethylaminopyridine (DMAP) (0.70 g, 5.73 mmol), the ice bath was removed, and the mixture was stirred under an argon atmosphere at room temperature for 3 hours. The obtained mixed liquid was washed with distilled water and saturated saline. The organic layer was collected, dried over sodium sulfate, and then filtered. The solvent in the obtained filtrate was distilled away under reduced pressure. The obtained residue was subjected to silica gel column chromatography (eluent, hexane:ethyl acetate=3:2) to obtain Boc-glycine-cyanoethyl ester (5.70 g, yield: 88%).

(2) Glycine-cyanoethyl ester (Compound 18)

Boc-glycine-cyanoethyl ester (2.80 g, 12.27 mmol) and dioxane (7.5 mL) were mixed. To the obtained mixture, a 4 M solution of hydrogen chloride in dioxane (20 mL) was added, and this mixture was stirred at room temperature for 3 hours. Then, the solvent was distilled away under reduced pressure. The obtained white solid was washed with ethyl acetate. The solid was dried in vacuum to obtain glycine-cyanoethyl ester (1.90 g).

(3) 6-(4,4'-Dimethoxytrityl)hexanoic acid (Compound 21)

To an azeotropically dried solution of 6-hydroxy hexanoic acid (1.2 g, 9.08 mmol) and DMAP (113 mg, 0.92 mmol) in pyridine (30 mL), 4,4-dimethoxytrityl chloride (3.1 g, 9.15 mmol) was added, and the mixture was stirred at room temperature for 5 hours. Then, methanol (5 mL) was added thereto, and the mixture was stirred for 30 minutes. The mixed liquid was concentrated under reduced pressure, and then, the solution was diluted by the addition of dichloromethane. This solution was washed with a saturated aqueous solution of sodium bicarbonate three times and with saturated saline once. The organic layer was collected, dried over sodium sulfate, and then filtered. The solvent in the obtained filtrate was distilled away under reduced pressure. The residue was dried under reduced pressure to obtain unpurified 6-(4,4'-dimethoxytrityl)hexanoic acid (6.2 g).

(4) N-Amido-glycine-cyanoethyl ester (Compound 19)

Glycine-cyanoethyl ester (0.85 g, 6.70 mmol) was dissolved in N,N-dimethylformamide (15 mL). To this mixture, 6-(4,4'-dimethoxytrityl)hexanoic acid (6.2 g) and triethylamine (1.35 g, 13.34 mmol) were added, and the resulting mixture was stirred under ice cooling. After addition of EDC (2.55 g, 13.30 mmol), the ice bath was removed, and the mixture was stirred at room temperature for 15 hours. The obtained mixed liquid was concentrated under reduced pressure, and the solution was diluted by the addition of dichloromethane. The solution was washed with a saturated aqueous solution of sodium bicarbonate and with saturated saline. The organic layer was collected, dried over sodium sulfate, and then filtered. The solvent in the obtained filtrate was distilled away under reduced pressure. The obtained residue was subjected to silica gel column chromatography (eluent, hexane:ethyl acetate=1:1, containing 0.05% pyridine) to obtain a white solid (2.50 g, yield 69%). The obtained white solid (2.50 g, 4.59 mmol) was added to an 80% aqueous acetic acid solution (30 mL), and the mixture was stirred at room temperature for 3 hours. The reaction solution was placed in a separating funnel and washed with hexane until the deprotected 4,4-dimethoxytrityl group could be removed from an aqueous layer. Toluene was added to the aqueous layer, which was then azeotroped three times. The residue was dried in vacuum to obtain N-amido-glycine-cyanoethyl ester (0.80 g, yield: 72%) as a white solid.

(5) Cyanoethyl-glycine amidite (Compound 20)

N-Amido-glycine-cyanoethyl ester (0.80 g, 3.30 mmol) was azeotroped with anhydrous acetonitrile twice. Diisopropyl ammonium tetrazolide (0.68 g, 3.97 mmol) was added thereto, which was then dried in vacuum. To this mixture, anhydrous acetonitrile (3 mL) was added. A solution of 2-cyanoethyl-N,N,N',N'-tetraisopropylphosphorodiamidite (1.20 g, 3.98 mmol) in anhydrous acetonitrile (1 mL) was added thereto. This mixture was stirred under an argon atmosphere at room temperature for 3 hours. The obtained mixture was diluted with dichloromethane and washed with a saturated aqueous solution of sodium bicarbonate and saturated saline. The organic layer was collected, dried over sodium sulfate, and then filtered. The solvent in the obtained filtrate was distilled away under reduced pressure. Cyanoethyl-glycine amidite (1.4 g) was obtained as an oily substance.

Example 3

In Example 4 mentioned later, a hairpin single-stranded RNA molecule having a TGF-β1 gene expression-inhibiting sequence (hereinafter, also referred to as "ssTbRNA") is produced by linking two segmentation fragments, i.e., a first single-stranded oligo-RNA molecule, which has an amino group at the end (hereinafter, strand A) and a second single-stranded oligo-RNA molecule, which has a carboxyl group at the end (strand B), by amidation reaction (see FIG. 1).

In this Example, strand A and strand B-1, with Ly, Lx$^1$ and Lx$^2$ having the following structures, were synthesized.

trichloroacetic acid in toluene for 1 hour and then removing the solution. The same strand B-1 is obtained using either compound 7 or compound 11.

An aqueous sodium chloride solution and 2-propanol were added to each reaction solution after nucleic acid synthesis, which was then centrifuged and a supernatant was removed. The obtained precipitate was dissolved in water for injection and purified using reverse phase chromatography (Inertsil ODS-3, GL Sciences Inc.; mobile phase A: 50 mM TEAB buffer solution, 5% acetonitrile; mobile phase B: 50 mM TEAB buffer solution, 50% acetonitrile). An aqueous sodium chloride solution and ethanol were added to the fraction of interest, which was then centrifuged to collect a precipitate. The obtained products were verified to have the molecular weight of interest by mass spectrometry. The collected products of interest were strand A having non-nucleotide linker Lx$^1$ having an amino group at the 3' end and strand B-1 having non-nucleotide linker Lx$^2$ having a carboxyl group at the 5' end. Ly and Lx$^2$ of the strand B-1 have a pyrrolidine backbone.

In the following Example, the hairpin single-stranded RNA molecule (ssTbRNA) is produced by linking the terminal amino group of the strand A to the terminal carboxyl group of the strand B-1 through an amide bond.

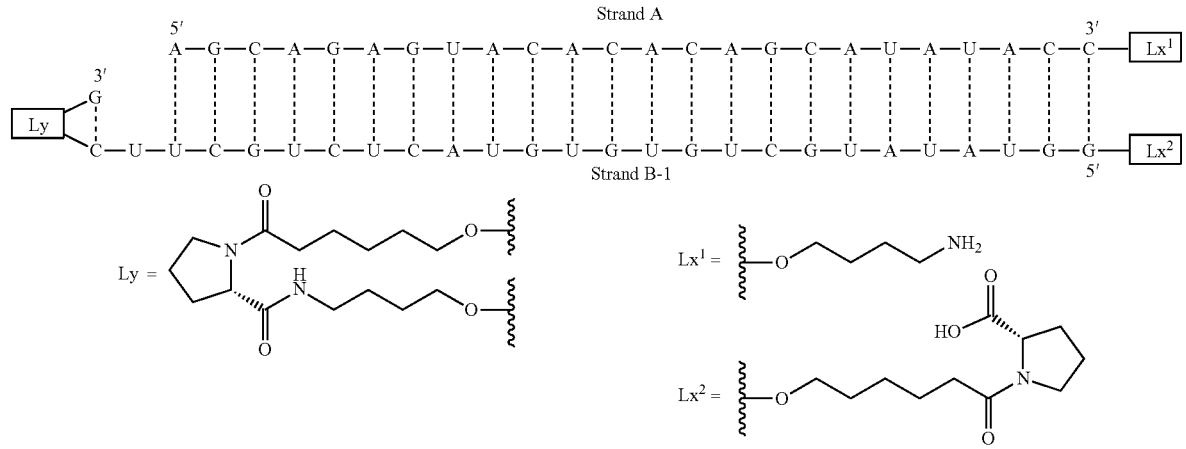

Strand A and strand B-1 were synthesized by phosphoramidite chemistry using an automated nucleic acid synthesizer (AKTA oligopilot plus 10, GE Healthcare Life Sciences). For this synthesis, TBDMS amidite was used as an RNA amidite. For the 3' end of the strand B-1, NittoPhase® (Nitto Denko Corp.) HL rG(ibu), which is polymer beads for nucleic acid synthesis bound to protected guanosine, was used; DMTr-diamido-L-proline amidite (compound 4) was used as a special amidite for linking Ly; and cyanoethyl-L-proline amidite (compound 7) or (2,4-dimethoxy)benzyl-L-proline amidite (compound 11) was used for linking Lx$^2$. For the 3' end of the strand A, 3'-PT Amino-Modifier C4 CPG (compound name: N-(4-(4,4'-dimethoxytrityloxy)-butyl)-(2-carboxyamido)-phthalimidyl-lcaa-CPG; Link Technologies Ltd.) was used. Solid-phase nucleic acid synthesis and deprotection reaction after the synthesis were carried out according to conventional methods. A cyanoethyl group is deprotected when a nucleic acid is cleaved from the solid-phase carrier. The deprotection of (2,4-dimethoxy) benzyl group was performed by allowing the solid-phase carrier after the end of synthesis to stand in a 3% solution of Example 4

Strand A and strand B-1 synthesized in Example 3 were subjected to amidation reaction under various reaction conditions using any method of the following operations A to C, to link strand A and strand B-1. Reaction yields were determined by HPLC analysis.

Operation A: 380 μL of a 5.3 mM aqueous solution of strand A and 360 μL of a 5.6 mM aqueous solution of strand B-1 were mixed and volumetrically adjusted to 2 mL by the addition of water, and a 30 μL aliquot was taken from the resulting solution. The solvent was distilled away using a reduced-pressure evaporator and a vacuum pump, thereby drying the solution. The obtained residue was dissolved by the addition of a buffer solution at room temperature. Then, an organic solvent and a 0.4 M aqueous solution of a dehydration condensation agent were added thereto, and the mixture was stirred at room temperature.

Operation B: 380 μL of a 5.3 mM aqueous solution of strand A and 360 μL of a 5.6 mM aqueous solution of strand B-1 were mixed and volumetrically adjusted to 2 mL by the addition of water, and a 30 µL aliquot was taken from the resulting solution. The solvent was distilled away using a reduced-pressure evaporator and a vacuum pump, thereby drying the solution. The obtained residue was dissolved by the addition of a buffer solution at room temperature. Then, an organic solvent and a 0.4 M solution of a dehydration condensation agent in an organic solvent were added thereto, and the mixture was stirred at room temperature. This dehydration condensation agent solution was prepared using the same organic solvent as that of the organic solvent to be mixed therewith (described in the table below).

Operation C: 380 µL of a 5.3 mM aqueous solution of strand A and 360 µL of a 5.6 mM aqueous solution of strand B-1 were mixed and volumetrically adjusted to 2 mL by the addition of water, and a 30 µL aliquot was taken from the resulting solution. The solvent was distilled away using a reduced-pressure evaporator and a vacuum pump, thereby drying the solution. The obtained residue was dissolved by the addition of a buffer solution at room temperature. Then, a dehydration condensation agent was added thereto in a solid form, and the mixture was stirred at room temperature.

Operation D: 170 µL of a 4.8 mM aqueous solution of strand A and 170 µL of a 4.8 mM aqueous solution of strand B-1 were mixed and volumetrically adjusted to 1 mL by the addition of water, and a 38 µL aliquot was taken from the resulting solution. The solvent was distilled away from the solution using a reduced-pressure evaporator and a vacuum pump, thereby drying the solution. The obtained residue was dissolved by the addition of a buffer solution at room temperature. Then, an organic solvent and a 0.4 M solution of a dehydration condensation agent in an organic solvent were added thereto, and the mixture was stirred at room temperature. This dehydration condensation agent solution was prepared using the same organic solvent as that of the organic solvent to be mixed therewith (described in the table below).

Operation E: 170 µL of a 4.8 mM aqueous solution of strand A and 170 µL of a 4.8 mM aqueous solution of strand B-1 were mixed and volumetrically adjusted to 1 mL by the addition of water, and a 38 µL aliquot was taken from the resulting solution. The solvent was distilled away from the solution using a reduced-pressure evaporator and a vacuum pump, thereby drying the solution. The obtained residue was dissolved by the addition of a buffer solution at room temperature. Then, a dehydration condensation agent was added thereto in a solid form, and the mixture was stirred at room temperature.

Operation F: 170 µL of a 4.8 mM aqueous solution of strand A and 170 µL of a 4.8 mM aqueous solution of strand B-1 were mixed and volumetrically adjusted to 1 mL by the addition of water, and a 38 µL aliquot was taken from the resulting solution. The solvent was distilled away from the solution using a reduced-pressure evaporator and a vacuum pump, thereby drying the solution. The obtained residue was dissolved by the addition of a buffer solution at room temperature. Then, an organic solvent and a 1.6 M solution of a dehydration condensation agent in an organic solvent were added thereto, and the mixture was stirred at room temperature. This dehydration condensation agent solution was prepared using the same organic solvent as that of the organic solvent to be mixed therewith (described in the table below).

Operation G: 170 µL of a 4.8 mM aqueous solution of strand A and 170 µL of a 4.8 mM aqueous solution of strand B-1 were mixed and volumetrically adjusted to 1 mL by the addition of water, and a 38 µL aliquot was taken from the resulting solution. The solvent was distilled away from the solution using a reduced-pressure evaporator and a vacuum pump, thereby drying the solution. The obtained residue was dissolved by the addition of a buffer solution at room temperature. Then, an organic solvent and a 0.2 M solution of a dehydration condensation agent (a 1:1 (volume ratio) mixed solution of water for injection and acetonitrile) were added thereto, and the mixture was stirred at room temperature.

The reaction solutions were sampled 1, 3, 5, 8, and 23 hours after addition of the dehydration condensation agent, and analyzed by HPLC to determine reaction yields. HPLC analysis conditions were as follows:

Column: XBridge Oligonucleotide BEH C18 (Waters Corp.) 4.6×50 mm, 2.5 µm
Column temperature: 60° C.
Mobile phase A: 200 mM aqueous TEAA solution (pH 7.0)/acetonitrile=95/5
Mobile phase B: 200 mM aqueous TEAA solution (pH 7.0)/acetonitrile=50/50
Development conditions: A/B=100/0 (0-3 min), 100/0 to 70/30 (3-23 min, linear gradient), 70/30 (23-33 min), 70/30 to 100/0 (33-33.1 min, linear gradient), 100/0 (33.1-45 min)
Flow rate: 1.0 mL/min
Detection: PDA detector (254 nm)
Injection volume: 10 µL.

The reaction yield (%) was calculated according to the following expression on the basis of HPLC analysis results:

Reaction yield (%)=(Peak area of ssTbRNA)/(Total peak area in a chromatogram)×100.

1) Examination of Dehydration Condensation Agent

For examination of the dehydration condensation agent, amidation reaction was carried out by the procedure described above in Test Examples 1 to 4 and 21 to 32 and Comparative Examples 1 to 9 and 12 to 22. The operation, the buffer solution added and the amount thereof, the organic solvent added and the amount thereof and the dehydration condensation agent added and the amount thereof in Test Examples 1 to 4 and 21 to 32 and Comparative Examples 1 to 9 and 12 to 22 are shown in Tables 1, 2, and 3.

TABLE 1

| | Buffer solution | Amount added of buffer solution | Organic solvent | Amount added of organic solvent* | Dehydration condensation agent | Amount added of dehydration condensation agent** | Operation |
|---|---|---|---|---|---|---|---|
| Test Example 1 | 1M MOPS buffer solution pH 7.0 | 12 µL | DMSO | 15 µL | DMT-MM | 3 µL | A |
| Test Example 2 | 1M MOPS buffer solution pH 7.0 | 15 µL | DMSO | 12 µL | HATU | 3 µL | B |

TABLE 1-continued

| | Buffer solution | Amount added of buffer solution | Organic solvent | Amount added of organic solvent* | Dehydration condensation agent | Amount added of dehydration condensation agent** | Operation |
|---|---|---|---|---|---|---|---|
| Test Example 3 | 1M MOPS buffer solution pH 7.0 | 15 μL | DMSO | 12 μL | HBTU | 3 μL | B |
| Test Example 4 | 1M MOPS buffer solution pH 7.0 | 15 μL | DMSO | 12 μL | EDCI hydrochloride, HOAt | 3 μL | B |
| Comparative Example 1 | 1M MOPS buffer solution pH 7.0 | 15 μL | DMSO | 12 μL | EDCI hydrochloride | 3 μL | B |
| Comparative Example 2 | 1M MOPS buffer solution pH 7.0 | 15 μL | DMSO | 12 μL | TSTU | 3 μL | B |
| Comparative Example 3 | 1M MOPS buffer solution pH 7.0 | 15 μL | DMSO | 12 μL | TFFH | 3 μL | B |
| Comparative Example 4 | 1M MOPS buffer solution pH 7.0 | 15 μL | DMSO | 12 μL | COMU | 3 μL | B |
| Comparative Example 5 | 1M MOPS buffer solution pH 7.0 | 15 μL | DMSO | 12 μL | PyBOP | 3 μL | B |
| Comparative Example 6 | 1M MOPS buffer solution pH 7.0 | 15 μL | DMSO | 12 μL | DPPA | 3 μL | B |
| Comparative Example 7 | 1M MOPS buffer solution pH 7.0 | 15 μL | DMSO | 12 μL | DPPA, HOAt | 3 μL | B |
| Comparative Example 8 | 1M MOPS buffer solution pH 7.0 | 15 μL | DMSO | 12 μL | CDI | 3 μL | B |
| Comparative Example 9 | 1M MOPS buffer solution pH 7.0 | 15 μL | DMSO | 12 μL | CDI, HOAt | 3 μL | B |

*Excluding amount of solvent contained in 0.4M aqueous solution of dehydration condensation agent or 0.4M solution in organic solvent of dehydration condensation agent
**Amount added of 0.4M aqueous solution of dehydration condensation agent or 0.4M solution in organic solvent of dehydration condensation agent The meanings of MOPS, DMT-MM, HATU, EDCI, and HOAt are as described above.

HBTU refers to O-(benzotriazol-1-yl)-N,N,N',N'-tetramethyluronium hexafluorophosphate. TSTU refers to N,N,N',N'-tetramethyl-O—(N-succinimidyl)uronium tetrafluoroborate. TFFH refers to fluoro-N,N,N',N'-tetramethylformamidinium hexafluorophosphate. COMIU® (Luxembourg Bio Technologies Ltd.) refers to 1-[(1-(cyano-2-ethoxy-2-oxoethylideneamino-oxy)dimethylaminomorpholino)]uronium hexafluorophosphate. PyBOP refers to (benzotriazol-1-yloxy)tripyrrolidinophosphonium hexafluorophosphate. DPPA refers to diphenylphosphoryl-azide. CDI refers to carbonyldiimidazole.

TABLE 2

| | Buffer solution | Amount added of buffer solution | Organic solvent | Amount added of organic solvent* | Dehydration condensation agent | Amount added of dehydration condensation agent** | Operation |
|---|---|---|---|---|---|---|---|
| Test Example 21 | 1M MOPS buffer solution pH 7.0 | 15 μL | DMSO | 12 μL | HCTU | 3 μL | B |
| Test Example 22 | 1M MOPS buffer solution pH 7.0 | 15 μL | DMSO | 12 μL | TPTU | 3 μL | D |

TABLE 2-continued

| | Buffer solution | Amount added of buffer solution | Organic solvent | Amount added of organic solvent* | Dehydration condensation agent | Amount added of dehydration condensation agent** | Operation |
|---|---|---|---|---|---|---|---|
| Test Example 23 | 1M MOPS buffer solution pH 7.0 | 15 μL | DMSO | 12 μL | TDBTU | 3 μL | D |
| Test Example 24 | 1M MOPS buffer solution pH 7.0 | 15 μL | DMSO | 12 μL | EDCI hydrochloride, HOBt | 3 μL | D |
| Test Example 25 | 1M MOPS buffer solution pH 7.0 | 15 μL | DMSO | 12 μL | EDCI hydrochloride, Compound 22 | 3 μL | D |
| Test Example 26 | 1M MOPS buffer solution pH 7.0 | 15 μL | DMSO | 12 μL | EDCI hydrochloride, HOPO | 3 μL | D |
| Test Example 27 | 1M MOPS buffer solution pH 7.0 | 15 μL | DMSO | 12 μL | EDCI hydrochloride, Compound 23 | 3 μL | D |
| Test Example 28 | 1M MOPS buffer solution pH 7.0 | 15 μL | DMSO | 12 μL | EDCI hydrochloride, Compound 24 | 3 μL | D |
| Test Example 29 | 1M MOPS buffer solution pH 7.0 | 15 μL | DMSO | 12 μL | EDCI hydrochloride, Compound 25 | 3 μL | D |
| Test Example 30 | 1M MOPS buffer solution pH 7.0 | 15 μL | DMSO | 12 μL | TCFH, HOAt | 3 μL | D |
| Test Example 31 | 1M MOPS buffer solution pH 7.0 | 15 μL | DMSO | 12 μL | TCFH, NMI | 3 μL | D |
| Test Example 32 | 1M MOPS buffer solution pH 7.0 | 15 μL | DMSO | 12 μL | Compound 26, HOAt | 3 μL | B |

*Excluding amount of solvent contained in 0.4M solution in organic solvent of dehydration condensation agent
**Amount added of 0.4M solution in organic solvent of dehydration condensation agent HCTU refers to O-(6-chlorobenzotriazol-1-yl)-N,N,N',N'-tetramethyluronium hexafluorophosphate. TPTU refers to O-(1,2-dihydro-2-oxo-1-pyridyl)-N,N,N',N'-tetramethyluronium tetrafluoroborate. TDBTU refers to O-(3,4-dihydro-4-oxo-1,2,3-benzotriazin-3-yl)-N,N,N',N'-tetramethyluronium tetrafluoroborate. HOBt refers to 1-hydroxybenzotriazole. HOPO refers to 2-hydroxypyridine-N-oxide. TCFH refers to chloro-N,N,N',N'-tetramethylformamidinium hexafluorophosphate. NMI refers to N-methylimidazole. Compound 22 refers to ethyl 1-hydroxy-1,2,3-triazole-4-carboxylate. Compound 23 refers to ethyl cyano(hydroxyimino)acetate. Compound 24 refers to 3,4-dihydro-3-hydroxy-4-oxo-1,2,3-benzotriazine. Compound 25 refers to 4-(dimethylamino)pyridine-N-oxide. Compound 26 refers to 2-chloro-1-methylpyridinium iodide.

TABLE 3

| | Buffer solution | Amount added of buffer solution | Organic solvent | Amount added of organic solvent * | Dehydration condensation agent | Amount added of dehydration condensation agent** | Operation |
|---|---|---|---|---|---|---|---|
| Comparative Example 12 | 1M MOPS buffer solution pH 7.0 | 15 μL | DMSO | 12 μL | HOTT | 3 μL | B |
| Comparative Example 13 | 1M MOPS buffer solution pH 7.0 | 15 μL | DMSO | 12 μL | Compound 27 | 3 μL | D |
| Comparative Example 14 | 1M MOPS buffer solution pH 7.0 | 15 μL | DMSO | 12 μL | DEPBT | 3 μL | D |

TABLE 3-continued

|  | Buffer solution | Amount added of buffer solution | Organic solvent | Amount added of organic solvent * | Dehydration condensation agent | Amount added of dehydration condensation agent** | Operation |
|---|---|---|---|---|---|---|---|
| Comparative Example 15 | 1M MOPS buffer solution pH 7.0 | 15 µL | DMSO | 12 µL | Compound 28 | 3 µL | D |
| Comparative Example 16 | 1M MOPS buffer solution pH 7.0 | 15 µL | DMF | 12 µL | Compound 29 | 3 µL | F |
| Comparative Example 17 | 1M MOPS buffer solution pH 7.0 | 15 µL | DMSO | 12 µL | TCFH | 3 µL | D |
| Comparative Example 18 | 1M MOPS buffer solution pH 7.0 | 15 µL | DMSO | 12 µL | EDCI hydrochloride, DMAP | 3 µL | D |
| Comparative Example 19 | 1M MOPS buffer solution pH 7.0 | 15 µL | DMSO | 12 µL | Compound 28, HOAt | 3 µL | D |
| Comparative Example 20 | 1M MOPS buffer solution pH 7.0 | 15 µL | DMSO | 12 µL | TCFH, DMAP | 3 µL | D |
| Comparative Example 21 | Water for injection | 12 µL | Acetonitrile | 12 µL | DIC, HOPO | 6 µL | G |
| Comparative Example 22 | Water for injection | 15 µL | DMSO | 12 µL | HATU | 3 µL | D |

*Excluding amount of solvent contained in 0.4M solution in organic solvent, 1.6M solution in organic solvent or 0.2M solution (1:1 (volume ratio) mixed solution of water for injection and acetonitrile) of dehydration condensation agent
**Amount added of 0.4M solution in organic solvent of dehydration condensation agent, 1.6M solution in organic solvent of dehydration condensation agent or 0.2M solution (1:1 (volume ratio) mixed solution of water for injection and acetonitrile) of dehydration condensation agent HOTT refers to N,N,N',N'-tetramethyl-S-(1-oxide-2-pyridyl)thiouronium hexafluorophosphate. DEPBT refers to diethyl 3,4-dihydro-4-oxo-1,2,3-benzotriazin-3-yl phosphate. DMAP refers to 4-dimethylaminopyridine. DIC refers to diisopropylcarbodiimide. Compound 27 refers to 3-nitro-1-tosyl-1,2,4-triazole. Compound 28 refers to N-tert-butyl-5-methylisoxazol-ium perchlorate. Compound 29 refers to 2,4,6-tripropyl-1,3,5,2,4,6-trioxatriphosphorinane.

Difference in reactivity among the dehydration condensation agents is shown in Tables 4, 5, and 6.

TABLE 4

|  | Dehydration condensation agent | Organic solvent | Organic solvent ratio | Buffer solution pH | Reaction yield (%) at each time | | | | |
|---|---|---|---|---|---|---|---|---|---|
|  |  |  |  |  | 1 hr | 3 hr | 5 hr | 8 hr | 23 hr |
| Test Example 1 | DMT-MM | DMSO | 50 vol % | 7.0 | 39 | 61 | 68 | 70 | 67 |
| Test Example 2 | HATU | DMSO | 50 vol % | 7.0 | 72 | 83 | 83 | 83 | 83 |
| Test Example 3 | HBTU | DMSO | 50 vol % | 7.0 | 22 | 41 | 56 | 68 | 83 |
| Test Example 4 | EDCI hydrochloride, HOAt | DMSO | 50 vol % | 7.0 | 83 | 76 | 74 | 70 | unmeasured |
| Comparative Example 1 | EDCI hydrochloride | DMSO | 50 vol % | 7.0 | unmeasured | 0 | 0 | 0 | unmeasured |
| Comparative Example 2 | TSTU | DMSO | 50 vol % | 7.0 | 3 | 5 | 5 | 5 | unmeasured |
| Comparative Example 3 | TFFH | DMSO | 50 vol % | 7.0 | 24 | 24 | 24 | 24 | unmeasured |
| Comparative Example 4 | COMU | DMSO | 50 vol % | 7.0 | 27 | 27 | 27 | 27 | unmeasured |

TABLE 4-continued

| | Dehydration condensation agent | Organic solvent | Organic solvent ratio | Buffer solution pH | Reaction yield (%) at each time | | | | |
|---|---|---|---|---|---|---|---|---|---|
| | | | | | 1 hr | 3 hr | 5 hr | 8 hr | 23 hr |
| Comparative Example 5 | PyBOP | DMSO | 50 vol % | 7.0 | 18 | 24 | 24 | 24 | unmeasured |
| Comparative Example 6 | DPPA | DMSO | 50 vol % | 7.0 | 0 | 1 | 1 | 1 | unmeasured |
| Comparative Example 7 | DPPA, HOAt | DMSO | 50 vol % | 7.0 | 0 | 1 | 1 | 1 | unmeasured |
| Comparative Example 8 | CDI | DMSO | 50 vol % | 7.0 | 0 | 0 | 0 | 0 | unmeasured |
| Comparative Example 9 | CDI, HOAt | DMSO | 50 vol % | 7.0 | 0 | 0 | 0 | 0 | unmeasured |

As shown in Table 4, use of DMT-MM, HATU, HBTU, or a combination of EDCI hydrochloride and HOAt as the dehydration condensation agent produced a high yield (Test Examples 1 to 4), whereas a phosphonium-based dehydration condensation agent such as PyBOP, albeit being a dehydration condensation agent containing the same benzotriazolyl structure as that of HATU and HBTU, did not produce a high yield (Comparative Example 5). Among uronium-based dehydration condensation agents, TSTU, TFFH, or COMU® (Luxembourg Bio Technologies Ltd.) containing no N-hydroxy nitrogen-containing aromatic ring structure did not produce a high yield (Comparative Examples 2 to 4).

TABLE 5

| | Dehydration condensation agent | Organic solvent | Organic solvent ratio | Buffer solution pH | Reaction yield (%) at each time | | | | |
|---|---|---|---|---|---|---|---|---|---|
| | | | | | 1 hr | 3 hr | 5 hr | 8 hr | 23 hr |
| Test Example 21 | HCTU | DMSO | 50 vol % | 7.0 | 52 | 70 | 75 | 76 | 78 |
| Test Example 22 | TPTU | DMSO | 50 vol % | 7.0 | 2 | 10 | 16 | 24 | 41 |
| Test Example 23 | TDBTU | DMSO | 50 vol % | 7.0 | 53 | 54 | 51 | 52 | unmeasured |
| Test Example 24 | EDCI hydrochloride, HOBt | DMSO | 50 vol % | 7.0 | 71 | 70 | 67 | 62 | unmeasured |
| Test Example 25 | EDCI hydrochloride, Compound 22 | DMSO | 50 vol % | 7.0 | 52 | 61 | 60 | 58 | unmeasured |
| Test Example 26 | EDCI hydrochloride, HOPO | DMSO | 50 vol % | 7.0 | 39 | 63 | 69 | 74 | 77 |
| Test Example 27 | EDCI hydrochloride, Compound 23 | DMSO | 50 vol % | 7.0 | 66 | 68 | 69 | 70 | unmeasured |
| Test Example 28 | EDCI hydrochloride, Compound 24 | DMSO | 50 vol % | 7.0 | 71 | 74 | 70 | 68 | unmeasured |
| Test Example 29 | EDCI hydrochloride, Compound 25 | DMSO | 50 vol % | 7.0 | 46 | 57 | 54 | 51 | unmeasured |
| Test Example 30 | TCFH, HOAt | DMSO | 50 vol % | 7.0 | 70 | 82 | 81 | 82 | unmeasured |
| Test Example 31 | TCFH, NMI | DMSO | 50 vol % | 7.0 | 69 | 75 | 76 | 73 | unmeasured |
| Test Example 32 | Compound 26, HOAt | DMSO | 50 vol % | 7.0 | 74 | 70 | 66 | 52 | unmeasured |

As shown in Table 5, HCTU, TPTU or TDBTU used alone, a combination of EDCI hydrochloride and HOBt, compound 22, HOPO, compound 23, compound 24 or compound 25, a combination of TCFH and HOAt or NIV, or a combination of compound 26 and HOAt as the dehydration condensation agent produced a high yield (Test Examples 21 to 32).

TABLE 6

| | Dehydration condensation agent | Organic solvent | Organic solvent ratio | Buffer solution pH | Reaction yield (%) at each time | | | | |
|---|---|---|---|---|---|---|---|---|---|
| | | | | | 1 hr | 3 hr | 5 hr | 8 hr | 23 hr |
| Comparative Example 12 | HOTT | DMSO | 50 vol % | 7.0 | 0 | 0 | 0 | 1 | unmeasured |
| Comparative Example 13 | Compound 27 | DMSO | 50 vol % | 7.0 | 16 | 16 | 16 | 16 | unmeasured |
| Comparative Example 14 | DEPBT | DMSO | 50 vol % | 7.0 | 4 | 6 | 7 | 8 | unmeasured |
| Comparative Example 15 | Compound 28 | DMSO | 50 vol % | 7.0 | 0 | 0 | 0 | 0 | unmeasured |
| Comparative Example 16 | Compound 29 | DMF | 50 vol % | 7.0 | 0 | 0 | 0 | 0 | unmeasured |
| Comparative Example 17 | TCFH | DMSO | 50 vol % | 7.0 | 3 | 3 | 3 | 3 | unmeasured |
| Comparative Example 18 | EDCI hydrochloride, DMAP | DMSO | 50 vol % | 7.0 | 10 | 14 | 15 | 14 | unmeasured |
| Comparative Example 19 | Compound 28, HOAt | DMSO | 50 vol % | 7.0 | 2 | 3 | 3 | 4 | unmeasured |
| Comparative Example 20 | TCFH, DMAP | DMSO | 50 vol % | 7.0 | 1 | 2 | 3 | 5 | unmeasured |
| Comparative Example 21 | DIC, HOPO | Acetonitrile | 50 vol % | — | 2 | 4 | 6 | 7 | unmeasured |
| Comparative Example 22 | HATU | DMSO | 50 vol % | — | 0 | 0 | unmeasured | 0 | unmeasured |

As shown in Table 6, the yield was reduced as a result of using water for injection instead of the buffer solution (Comparative Examples 21 and 22).

These results indicated that a uronium-based dehydration condensation agent comprising an N-hydroxy nitrogen-containing aromatic ring structure (e.g., 1-hydroxybenzotriazole structure) (e.g., a benzotriazolyluronium-based dehydration condensation agent) or a combination of EDCI hydrochloride and an N-hydroxy nitrogen-containing aromatic compound produces a high yield. On the other hand, in using DPPA or CDI, the dehydration condensation agent used alone or in combination with HOAt did not produce a high yield (Comparative Examples 6 to 9).

2) Amidation Reaction Using Triazine-Based Dehydration Condensation Agent

For examination of reaction conditions for amidation reaction using the triazine-based dehydration condensation agent, amidation reaction was carried out by the procedure described above using DMT-MM as the dehydration condensation agent in Test Examples 1 and 5 to 14 and Comparative Example 10. The operation, the buffer solution added and the amount thereof, the organic solvent added and the amount thereof, and the dehydration condensation agent added and the amount thereof in Test Examples 1 and 5 to 14 and Comparative Example 10 are shown in Table 7.

TABLE 7

| | Buffer solution | Amount added of buffer solution | Organic solvent | Amount added of organic solvent | Dehydration condensation agent | Amount added of dehydration condensation agent* | Operation |
|---|---|---|---|---|---|---|---|
| Test Example 1 | 1M MOPS buffer solution pH 7.0 | 12 μL | DMSO | 15 μL | DMT-MM | 3 μL | A |
| Test Example 5 | 1M MOPS buffer solution pH 7.0 | 12 μL | DMF | 15 μL | DMT-MM | 3 μL | A |
| Test Example 6 | 1M MOPS buffer solution pH 7.0 | 12 μL | DMEU | 15 μL | DMT-MM | 3 μL | A |
| Test Example 7 | 1M MOPS buffer solution pH 7.0 | 12 μL | Acetonitrile | 15 μL | DMT-MM | 3 μL | A |

TABLE 7-continued

| | Buffer solution | Amount added of buffer solution | Organic solvent | Amount added of organic solvent | Dehydration condensation agent | Amount added of dehydration condensation agent* | Operation |
|---|---|---|---|---|---|---|---|
| Test Example 8 | 1M MOPS buffer solution pH 7.0 | 12 μL | tBuOH | 15 μL | DMT-MM | 3 μL | A |
| Test Example 9 | 1M MOPS buffer solution pH 7.0 | 16.5 μL | DMSO | 10.5 μL | DMT-MM | 3 μL | A |
| Test Example 10 | 1M MOPS buffer solution pH 7.0 | 10.5 μL | DMSO | 16.5 μL | DMT-MM | 3 μL | A |
| Test Example 11 | 1M MOPS buffer solution pH 7.0 | 9 μL | DMSO | 18 μL | DMT-MM | 3 μL | A |
| Test Example 12 | 1M MOPS buffer solution pH 6.5 | 12 μL | DMSO | 15 μL | DMT-MM | 3 μL | A |
| Test Example 13 | 1M MOPS buffer solution pH 7.5 | 12 μL | DMSO | 15 μL | DMT-MM | 3 μL | A |
| Test Example 14 | 1M MES buffer solution pH 6.0 | 12 μL | DMSO | 15 μL | DMT-MM | 3 μL | A |
| Comparative Example 10 | 1M MOPS buffer solution pH 7.0 | 27 μL | (no addition) | (no addition) | DMT-MM | 3 μL | A |

*Amount added of 0.4M aqueous solution of dehydration condensation agent

The effect of addition of the organic solvent, the influence of the organic solvent ratio, and the influence of the buffer solution pH are shown in Tables 8 to 10. In the tables, the organic solvent ratio was calculated with also including, in the total amount of the organic solvent, the amount of the organic solvent contained in the dehydration condensation agent solution used for amidation.

TABLE 8

| | Dehydration condensation agent | Organic solvent | Organic solvent ratio | Buffer solution pH | Reaction yield (%) at each time | | | | |
|---|---|---|---|---|---|---|---|---|---|
| | | | | | 1 hr | 3 hr | 5 hr | 8 hr | 23 hr |
| Comparative Example 10 | DMT-MM | (no addition) | 0 vol % | 7.0 | 6 | unmeasured | unmeasured | 22 | 28 |
| Test Example 1 | DMT-MM | DMSO | 50 vol % | 7.0 | 39 | 61 | 68 | 70 | 67 |
| Test Example 5 | DMT-MM | DMF | 50 vol % | 7.0 | 19 | unmeasured | unmeasured | 49 | 52 |
| Test Example 6 | DMT-MM | DMEU | 50 vol % | 7.0 | 11 | unmeasured | unmeasured | 34 | 43 |
| Test Example 7 | DMT-MM | Acetonitrile | 50 vol % | 7.0 | 8 | unmeasured | unmeasured | 36 | 40 |
| Test Example 8 | DMT-MM | tBuOH | 50 vol % | 7.0 | unmeasured | 22 | 30 | 35 | 41 |

As shown in Table 8, the yield of the product of interest was improved as a result of adding the organic solvent as compared with no addition of the organic solvent (Comparative Example 10). Particularly, the addition of DMSO was highly effective (Test Example 1).

TABLE 9

| | Dehydration condensation agent | Organic solvent | Organic solvent ratio | Buffer solution pH | Reaction yield (%) at each time | | | | |
|---|---|---|---|---|---|---|---|---|---|
| | | | | | 1 hr | 3 hr | 5 hr | 8 hr | 23 hr |
| Test Example 9 | DMT-MM | DMSO | 35 vol % | 7.0 | 20 | 41 | unmeasured | 59 | 61 |
| Test Example 1 | DMT-MM | DMSO | 50 vol % | 7.0 | 39 | 61 | 68 | 70 | 67 |
| Test Example 10 | DMT-MM | DMSO | 55 vol % | 7.0 | 41 | 67 | 71 | 72 | 69 |
| Test Example 11 | DMT-MM | DMSO | 60 vol % | 7.0 | unmeasured | unmeasured | 59 | 62 | 61 |

As shown in Table 9, the product of interest was obtained with a high yield when the ratio of DMSO was set to from 35 to 60 v/v % of the whole solvent (Test Examples 1 and 9 to 11).

TABLE 10

| | Dehydration condensation agent | Organic solvent | Organic solvent ratio | Buffer solution pH | Reaction yield (%) at each time | | | | |
|---|---|---|---|---|---|---|---|---|---|
| | | | | | 1 hr | 3 hr | 5 hr | 8 hr | 23 hr |
| Test Example 14 | DMT-MM | DMSO | 50 vol % | 6.0 | 7 | 16 | 22 | 26 | 35 |
| Test Example 12 | DMT-MM | DMSO | 50 vol % | 6.5 | 13 | 26 | 32 | 37 | 43 |
| Test Example 1 | DMT-MM | DMSO | 50 vol % | 7.0 | 39 | 61 | 68 | 70 | 67 |
| Test Example 13 | DMT-MM | DMSO | 50 vol % | 7.5 | 47 | 60 | 60 | 59 | 57 |

As shown in Table 10, a particularly high yield was obtained within a pH range of 6.5 to 7.5. A tendency to reduce the yield with decrease in reaction rate was observed when the pH was decreased to 6.0.

3) Amidation Reaction Using Benzotriazolyluronium-Based Dehydration Condensation Agent For examination of reaction conditions for amidation reaction using the benzotriazolyluronium-based dehydration condensation agent, amidation reaction was carried out by the procedure described above using HATU as the dehydration condensation agent in Test Examples 2, 15 to 20, and 33 to 38 and Comparative Example 11. The operation, the buffer solution added and the amount thereof, the organic solvent added and the amount thereof, and the dehydration condensation agent added and the amount thereof in Test Examples 2, 15 to 20, and 33 to 38 and Comparative Example 11 are shown in Table 11.

TABLE 11

| | Buffer solution | Amount of buffer solution added | Organic solvent | Amount of organic solvent added* | Dehydration condensation agent | Amount of dehydration condensation agent added** | Operation |
|---|---|---|---|---|---|---|---|
| Test Example 2 | 1M MOPS buffer solution pH 7.0 | 15 μL | DMSO | 12 μL | HATU | 3 μL | B |
| Test Example 15 | 1M MOPS buffer solution pH 7.0 | 19.5 μL | DMSO | 7.5 μL | HATU | 3 μL | B |
| Test Example 16 | 1M MOPS buffer solution pH 7.0 | 15 μL | DMF | 12 μL | HATU | 3 μL | B |

TABLE 11-continued

| | Buffer solution | Amount of buffer solution added | Organic solvent | Amount of organic solvent added* | Dehydration condensation agent | Amount of dehydration condensation agent added** | Operation |
|---|---|---|---|---|---|---|---|
| Test Example 17 | 1M MOPS buffer solution pH 7.0 | 15 μL | DMEU | 12 μL | HATU | 3 μL | B |
| Test Example 18 | 1M MOPS buffer solution pH 7.0 | 15 μL | Sulfolane | 12 μL | HATU | 3 μL | B |
| Test Example 19 | 1M MOPS buffer solution pH 7.0 | 15 μL | Acetonitrile | 12 μL | HATU | 3 μL | B |
| Test Example 20 | 1M MOPS buffer solution pH 7.0 | 15 μL | Ethanol | 12 μL | HATU | 3 μL | B |
| Comparative Example 11 | 1M MOPS buffer solution pH 7.0 | 30 μL | (no addition) | (no addition) | HATU | 0.4 mg | C |
| Test Example 33 | 1M MOPS buffer solution pH 7.0 | 24 μL | DMSO | 3 μL | HATU | 3 μL | D |
| Test Example 34 | 1M MOPS buffer solution pH 7.0 | 10.5 μL | DMSO | 16.5 μL | HATU | 3 μL | D |
| Test Example 35 | 1M MOPS buffer solution pH 7.0 | 10.5 μL | DMF | 16.5 μL | HATU | 3 μL | D |
| Test Example 36 | 1M MOPS buffer solution pH 7.0 | 10.5 μL | DMEU | 16.5 μL | HATU | 3 μL | D |
| Test Example 37 | 1M MOPS buffer solution pH 7.0 | 10.5 μL | Acetonitrile | 16.5 μL | HATU | 3 μL | D |
| Test Example 38 | 1M MOPS buffer solution pH 7.0 | 15 μL | Tetrahydrofuran | 15 μL | HATU | 0.4 mg | E |

*Excluding amount of solvent contained in 0.4M solution in organic solvent of dehydration condensation agent
**Amount of dehydration condensation agent (solid) or 0.4M solution in organic solvent of dehydration condensation agent added The effect of addition of the organic solvent and the influence of the organic solvent ratio are shown in Tables 12 and 13.

TABLE 12

| | Dehydration condensation agent | Organic solvent | Organic solvent ratio | Buffer solution pH | Reaction yield (%) at each time | | | | |
|---|---|---|---|---|---|---|---|---|---|
| | | | | | 1 hr | 3 hr | 5 hr | 8 hr | 23 hr |
| Comparative Example 11 | HATU | (no addition) | 0 vol % | 7.0 | 1 | 4 | 7 | 10 | 20 |
| Test Example 2 | HATU | DMSO | 50 vol % | 7.0 | 72 | 83 | 83 | 83 | 83 |
| Test Example 16 | HATU | DMF | 50 vol % | 7.0 | 71 | 79 | 79 | 78 | unmeasured |
| Test Example 17 | HATU | DMEU | 50 vol % | 7.0 | 33 | 66 | 70 | 75 | 74 |
| Test Example 18 | HATU | Sulfolane | 50 vol % | 7.0 | 9 | 32 | 43 | 58 | 66 |
| Test Example 19 | HATU | Acetonitrile | 50 vol % | 7.0 | 17 | 51 | 64 | 74 | 78 |

TABLE 12-continued

| | Dehydration condensation agent | Organic solvent | Organic solvent ratio | Buffer solution pH | Reaction yield (%) at each time | | | | |
|---|---|---|---|---|---|---|---|---|---|
| | | | | | 1 hr | 3 hr | 5 hr | 8 hr | 23 hr |
| Test Example 20 | HATU | Ethanol | 50 vol % | 7.0 | 25 | 44 | 49 | 49 | unmeasured |
| Test Example 38 | HATU | Tetrahydrofuran | 50 vol % | 7.0 | 18 | 48 | 58 | 62 | unmeasured |

As shown in Table 12, the yield of the product of interest was improved as a result of adding the organic solvent (Test Examples 2, 16 to 20, and 38) as compared with no addition of the organic solvent (Comparative Example 11). Particularly, the addition of an aprotic hydrophilic organic solvent was highly effective.

TABLE 13

| | Dehydration condensation agent | Organic solvent | Organic solvent ratio | Buffer solution pH | Reaction yield (%) at each time | | | | |
|---|---|---|---|---|---|---|---|---|---|
| | | | | | 1 hr | 3 hr | 5 hr | 8 hr | 23 hr |
| Test Example 33 | HATU | DMSO | 20 vol % | 7.0 | 4 | 14 | 22 | 32 | 47 |
| Test Example 15 | HATU | DMSO | 35 vol % | 7.0 | 20 | 54 | 69 | 75 | 81 |
| Test Example 2 | HATU | DMSO | 50 vol % | 7.0 | 72 | 83 | 83 | 83 | 83 |
| Test Example 34 | HATU | DMSO | 65 vol % | 7.0 | 22 | 37 | 39 | 40 | unmeasured |
| Test Example 16 | HATU | DMF | 50 vol % | 7.0 | 71 | 79 | 79 | 78 | unmeasured |
| Test Example 35 | HATU | DMF | 65 vol % | 7.0 | 80 | 82 | 81 | 81 | unmeasured |
| Test Example 17 | HATU | DMEU | 50 vol % | 7.0 | 33 | 66 | 70 | 75 | 74 |
| Test Example 36 | HATU | DMEU | 65 vol % | 7.0 | 41 | 51 | 53 | 53 | unmeasured |
| Test Example 19 | HATU | Acetonitrile | 50 vol % | 7.0 | 17 | 51 | 64 | 74 | 78 |
| Test Example 37 | HATU | Acetonitrile | 65 vol % | 7.0 | 19 | 53 | 65 | 74 | unmeasured |

As shown in Table 13, the product of interest was obtained with a high yield when the ratio of DMSO was set to 20 to 65 v/v % of the whole solvent (Test Examples 2, 15, 33, and 34). Also, the product of interest was obtained with a high yield when the ratio of DMF, DMEU, or acetonitrile was set to 50 to 65 v/v % of the whole solvent (Test Examples 16, 17, 19, and 35 to 37).

Example 5

Isolation and Purification of ssTbRNA
1) Amidation Reaction Using DMT-MM

1 μmol aliquots were taken from an aqueous solution of strand A and an aqueous solution of strand B-1 and mixed. The solvent was distilled away using a centrifugal concentrator, thereby drying the solution. The obtained residue was dissolved by the addition of 80 μL of a 1 M MOPS buffer solution, and the solution was heated to 95° C. and then allowed to cool to room temperature. 80 μL of a 1 M aqueous DMT-MM solution and 100 μL of DMSO were added thereto, and the mixture was stirred and then allowed to stand at room temperature for 6 hours. To the reaction solution, 20 μL of a 2 M aqueous sodium chloride solution and 800 μL of ethanol were added, and the mixture was stirred, allowed to stand at −30° C., and then centrifuged and a supernatant was removed. The obtained precipitate was dried. The precipitate was dissolved in water for injection and purified by strong anion exchange chromatography (DNAPac PA100, Thermo Fisher Scientific Inc.; mobile phase A: 25 mM Tris-HCl buffer, 10% acetonitrile; mobile phase B: 25 mM Tris-HCl buffer, 10% acetonitrile, 700 mM NaClO$_4$) and the product of interest was fractionated. The fraction of interest was collected by ethanol precipitation to obtain 11.7 mg of a white solid (RP-HPLC purity: 90%, yield: 69%). The obtained product was verified to have the molecular weight of interest by mass spectrometry.

2) Amidation Reaction Using HATU

1 μmol aliquots were taken from an aqueous solution of strand A and an aqueous solution of strand B-1 and mixed. The solvent was distilled away using a centrifugal concentrator, thereby drying the solution. The obtained residue was dissolved by the addition of 100 μL of a 1 M MOPS buffer solution, and the solution was heated to 95° C. and then allowed to cool to room temperature. 100 μL of a 0.2 M solution of HATU in DMSO was added thereto, and the mixture was stirred and then allowed to stand at room temperature for 4 hours. To the reaction solution, 20 μL of a 2 M aqueous sodium chloride solution and 800 μL of ethanol were added, and the mixture was stirred, allowed to stand at −30° C., and then centrifuged and a supernatant was removed. The obtained precipitate was dried. The precipitate was dissolved in water for injection and purified by strong anion exchange chromatography (DNAPac PA100, Thermo Fisher Scientific Inc.; mobile phase A: 25 mM Tris-HCl buffer, 10% acetonitrile; mobile phase B: 25 mM Tris-HCl buffer, 10% acetonitrile, 700 mM NaClO₄) and the product of interest was fractionated. The fraction of interest was collected by ethanol precipitation to obtain 14.1 mg of a white solid (AEX-HPLC purity: 96%, yield: 83%). The obtained product was verified to have the molecular weight of interest by mass spectrometry.

The purity of ssTbRNA obtained by the procedure described above was analyzed by RP-UPLC (reversed phase ultra performance liquid chromatography) and compared to ssTbRNA synthesized by solid-phase synthesis using phosphoramidite chemistry described in WO '919. The results are shown in Table 14. RP-UPLC conditions and analysis conditions are as described below.

RP-UPLC Conditions:
  Column: ACQUITY UPLC Oligonucleotide BEH C18 130 Å (angstroms) (Waters Corp.), 2.1×100 mm, 1.7 μm
  Column temperature: 80° C.
  Mobile phase A: 50 mM TEAA, 1 mM EDTA aqueous solution (pH 7.3)
  Mobile phase B: 50 mM TEAA, 1 mM EDTA aqueous solution/methanol=20/80
  Development conditions: A/B=100/0 to 75/25 (0-10 min, linear gradient), 75/25 to 0/100 (10-10.5 min, linear gradient), 0/100 (10.5-15 min), 0/100 to 100/0 (15-15.5 min, linear gradient)
  Flow rate: 0.2 mL/min
  Detection: PDA detector (260 nm)
  Injection volume: 10 μL.
Analysis Conditions:
  Width: 2 sec
  Slope: 4000 μV/min
  Drift: 0 μV/min
  T.DBL: 1000 min
  Minimum area: 500 counts.

TABLE 14

| Synthesis approach | Strand A | Strand B | ssTbRNA | Nucleic acid molecules (including truncated products) at or near ssTbRNA peak |
|---|---|---|---|---|
| Procedure of 2) of Example 4 | 0.4% | 0.3% | 97.2% | 97.5% |
| Solid-phase synthesis | — | — | 87.9% | 91.6% |

In Table 14, the values of the strand A, the strand B-1 and the ssTbRNA molecule indicate their respective peak area ratios based on chromatograms and were calculated using the analysis conditions described above. In addition, as a relative amount of the nucleic acid (mainly including the ssTbRNA molecule and its truncated products) at or near the peak of the ssTbRNA molecule, total peak area percentage (%) within the range of RRT (relative retention time; herein, the relative retention time compared to the retention time of the peak of the ssTbRNA molecule that is set to 1)=0.98 to 1.07 was calculated. The peak retention time of the strand A or the strand B-1 was sufficiently apart from that of the ssTbRNA molecule and was not included in the range of RRT=0.98 to 1.07.

As shown in Table 14, there was a tiny amount of nucleic acid impurities contained in the ssTbRNA molecule population synthesized by our method. Besides, the amount of truncated products (with a lack of a portion of the sequence of the ssTbRNA molecule) appearing at or near the peak of the ssTbRNA molecule was also small. By contrast, solid-phase synthesis using phosphoramidite chemistry (WO'919) involved a relatively large amount of short-strand nucleic acid impurities (including RNA molecules resulting from early termination of synthesis during the stage of a short strand) other than the ssTbRNA molecule, and large amount of truncated products at or near the peak of the ssTbRNA molecule. Our method was shown to be able to produce hairpin single-stranded RNA molecules of interest in high purity.

Example 6

Strand A and strand B-2, with Ly, Lx¹ and Lx² having the following structures, were synthesized as two segmentation fragments of a hairpin single-stranded RNA molecule having a TGF-β1 gene expression-inhibiting sequence:

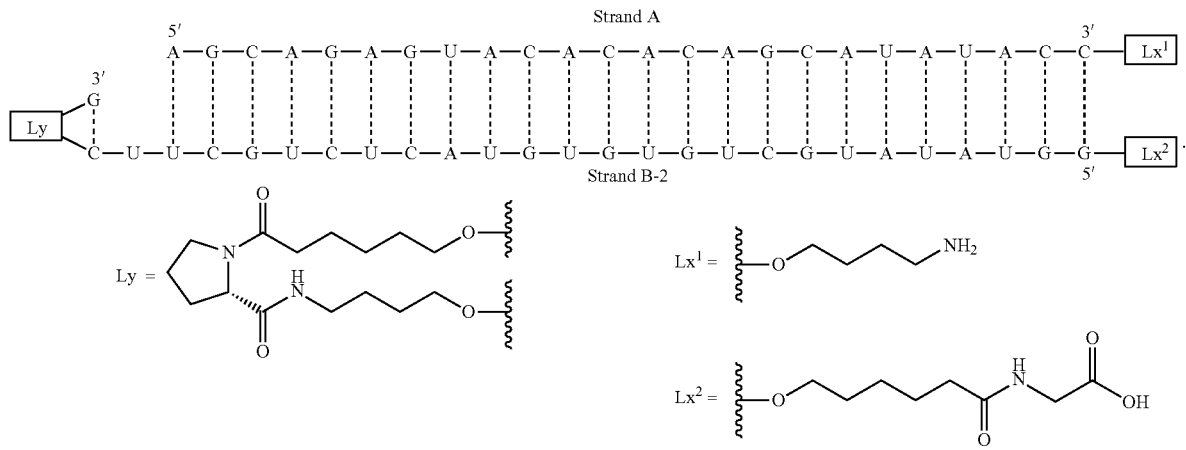

Strand A and strand B-2 were synthesized by phosphoramidite chemistry using an automated nucleic acid synthesizer (ABI3900; Applied Biosystems, Inc.). For this synthesis, TBDMS amidite was used as an RNA amidite. For the 3' end of the strand B-2, 2'-O-TBDMS-guanosine(N-iBu)-3'-lcaa-CPG (ChemGenes Corp.) was used; DMTr-diamido-L-proline amidite (Compound 4) was used as a special amidite for linking Ly; and cyanoethyl-glycine amidite (Compound 20) was used for linking $Lx^2$. For the 3' end of the strand A, 3'-PT Amino-Modifier C4 CPG (compound name: N-(4-(4,4'-dimethoxytrityloxy)-butyl)-(2-carboxyamido)-phthalimidyl-lcaa-CPG; ChemGenes Corp.) was used. Solid-phase nucleic acid synthesis and deprotection reaction after the synthesis were carried out according to conventional methods.

An aqueous sodium chloride solution and 2-propanol were added to a reaction solution after the end of deprotection reaction of each strand, which was then centrifuged and a supernatant was removed. The obtained precipitate was dissolved in water for injection. The obtained products were verified to have the molecular weight of interest by mass spectrometry. The collected products of interest were strand A having non-nucleotide linker $Lx^1$ having an amino group at the 3' end (mass spectrometry found: 7817.3, calcd: 7816.8) and strand B-2 having non-nucleotide linker $Lx^2$ having a carboxyl group at the 5' end (mass spectrometry found: 9195.0, calcd: 9194.6).

100 nmol aliquots were taken from an aqueous solution of strand A and an aqueous solution of strand B-2 and mixed. The solvent was distilled away using a centrifugal concentrator, thereby drying the solution. The obtained residue was dissolved by the addition of 10 µL of a 1 M MOPS buffer solution, and the solution was heated to 95° C. and then allowed to cool to room temperature. 10 µL of a 0.2 M solution of HATU in DMSO was added thereto, and the mixture was stirred and then allowed to stand at room temperature for 4 hours. To the reaction solution, 2 µL of a 2 M aqueous sodium chloride solution and 50 µL of ethanol were added, and the mixture was stirred, allowed to stand at −30° C., and then centrifuged and a supernatant was removed. The obtained precipitate was dried. The obtained product was verified to have the molecular weight of interest by mass spectrometry (found: 16993.9, calcd: 16993.3).

Example 7

Strand A and strand B-3, with Ly, $Lx^1$ and $Lx^2$ having the following structures, were synthesized as two segmentation fragments of a hairpin single-stranded RNA molecule having a TGF-β1 gene expression-inhibiting sequence:

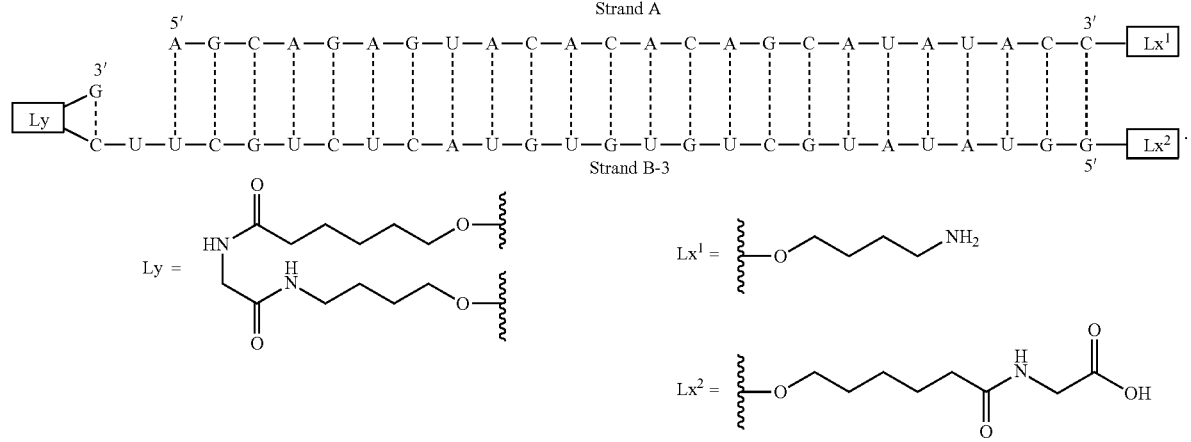

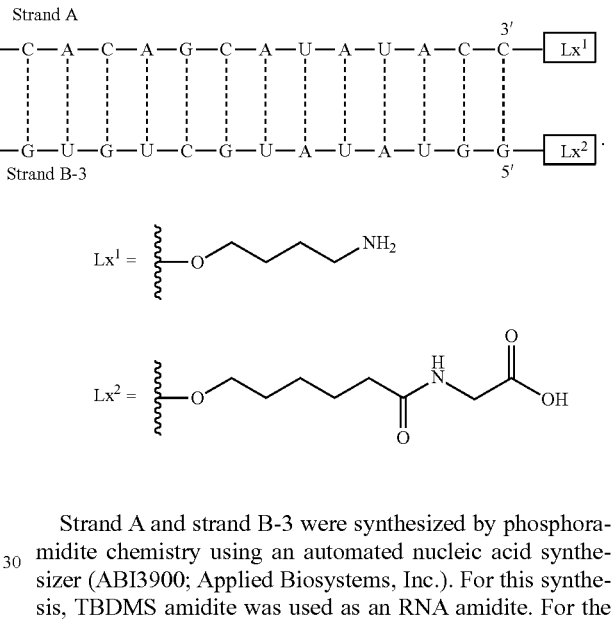

Strand A and strand B-3 were synthesized by phosphoramidite chemistry using an automated nucleic acid synthesizer (ABI3900; Applied Biosystems, Inc.). For this synthesis, TBDMS amidite was used as an RNA amidite. For the 3' end of the strand B-3, 2'-O-TBDMS-guanosine(N-iBu)-3'-lcaa-CPG (ChemGenes Corp.) was used; DMTr-diamido-glycine amidite (compound 16) was used as a special amidite for linking Ly; and cyanoethyl-glycine amidite (compound 20) was used for linking $Lx^2$. For the 3' end of the strand A, 3'-PT Amino-Modifier C4 CPG (compound name: N-(4-(4,4'-dimethoxytrityloxy)-butyl)-(2-carboxyamido)-phthalimidyl-lcaa-CPG; ChemGenes Corp.) was used. Solid-phase nucleic acid synthesis and deprotection reaction after the synthesis were carried out according to conventional methods.

An aqueous sodium chloride solution and 2-propanol were added to a reaction solution after the end of deprotection reaction of each strand, which was then centrifuged and a supernatant was removed. The obtained precipitate was dissolved in water for injection. The obtained products were verified to have the molecular weight of interest by mass spectrometry. The collected products of interest were strand A having non-nucleotide linker $Lx^1$ having an amino group at the 3' end (mass spectrometry found: 7817.3, calcd: 7816.8) and strand B-3 having non-nucleotide linker $Lx^2$ having a carboxyl group at the 5' end (mass spectrometry found: 9155.0, calcd: 9154.5).

100 nmol aliquots were taken from an aqueous solution of strand A and an aqueous solution of strand B-3 and mixed. The solvent was distilled away using a centrifugal concentrator, thereby drying the solution. The obtained residue was dissolved by the addition of 10 µL of a 1 M MOPS buffer solution, and the solution was heated to 95° C. and then allowed to cool to room temperature. 10 µL of a 0.2 M solution of HATU in DMSO was added thereto, and the mixture was stirred and then allowed to stand at room temperature for 4 hours. To the reaction solution, 2 µL of a 2 M aqueous sodium chloride solution and 50 µL of ethanol were added, and the mixture was stirred, allowed to stand at -30° C., and then centrifuged and a supernatant was removed. The obtained precipitate was dried. The obtained product was verified to have the molecular weight of interest by mass spectrometry (found: 16954.1, calcd: 16953.3).

Example 8

In this Example, a hairpin single-stranded RNA molecule having a GAPDH gene expression-inhibiting sequence was produced by linking two segmentation fragments, i.e., a first single-stranded oligo-RNA molecule having an amino group at the end (hereinafter, strand C) and a second single-stranded oligo-RNA molecule having a carboxyl group at the end (strand D) by amidation reaction.

First, in this Example, strand C and strand D-1, with Ly, Lx1 and Lx2 having the following structures, were synthesized:

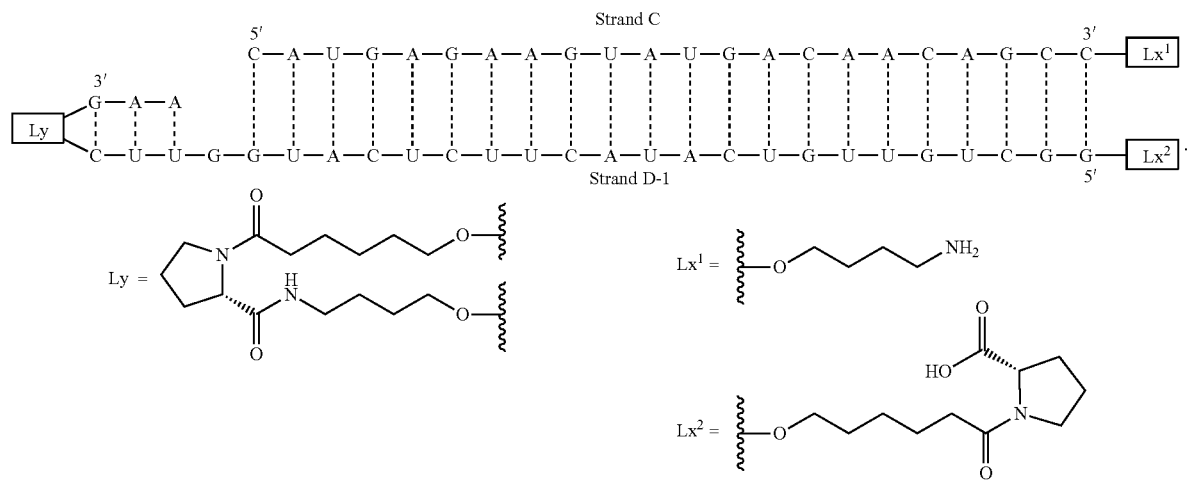

Strand C and strand D-1 were synthesized by phosphoramidite chemistry using an automated nucleic acid synthesizer (ABI3900; Applied Biosystems, Inc.). In this synthesis, TBDMS amidite was used as an RNA amidite. For the 3' end of the strand D-1, 2'-O-TBDMS-adenosine(N-Bz)-3'-lcaa-CPG (ChemGenes Corp.) was used; DMTr-diamido-L-proline amidite (compound 4) was used as a special amidite for linking Ly; and cyanoethyl-L-proline amidite (compound 7) was used for linking $Lx^2$. For the 3' end of the strand C, 3'-PT Amino-Modifier C4 CPG (compound name: N-(4-(4,4'-dimethoxytrityloxy)-butyl)-(2-carboxyamido)-phthalimidyl-lcaa-CPG; ChemGenes Corp.) was used. Solid-phase nucleic acid synthesis and deprotection reaction after the synthesis were carried out according to conventional methods.

An aqueous sodium chloride solution and 2-propanol were added to a reaction solution after the end of deprotection reaction of each strand, which was then centrifuged and a supernatant was removed. The obtained precipitate was dissolved in water for injection. The obtained products were verified to have the molecular weight of interest by mass spectrometry. The collected products of interest were strand C having non-nucleotide linker $Lx^1$ having an amino group at the 3' end (mass spectrometry found: 7222.9, calcd: 7222.4) and strand D-1 having non-nucleotide linker $Lx^2$ having a carboxyl group at the 5' end (mass spectrometry found: 9853.5, calcd: 9853.0).

100 nmol aliquots were taken from an aqueous solution of strand C and an aqueous solution of strand D-1 and mixed. The solvent was distilled away using a centrifugal concentrator, thereby drying the solution. The obtained residue was dissolved by the addition of 10 μL of a 1 M MOPS buffer solution, and the solution was heated to 95° C. and then allowed to cool to room temperature. 10 μL of a 0.2 M solution of HATU in DMSO was added thereto, and the mixture was stirred and then allowed to stand at room temperature for 4 hours. To the reaction solution, 2 μL of a 2 M aqueous sodium chloride solution and 50 μL of ethanol were added, and the mixture was stirred, allowed to stand at −30° C., and then centrifuged and a supernatant was removed. The obtained precipitate was dried. The obtained product was verified to have the molecular weight of interest by mass spectrometry (found: 17057.9, calcd: 17057.4).

Example 9

Strand C and strand D-2, with Ly, $Lx^1$ and $Lx^2$ having the following structures, were synthesized as two segmentation fragments of a hairpin single-stranded RNA molecule having a GAPDH gene expression-inhibiting sequence:

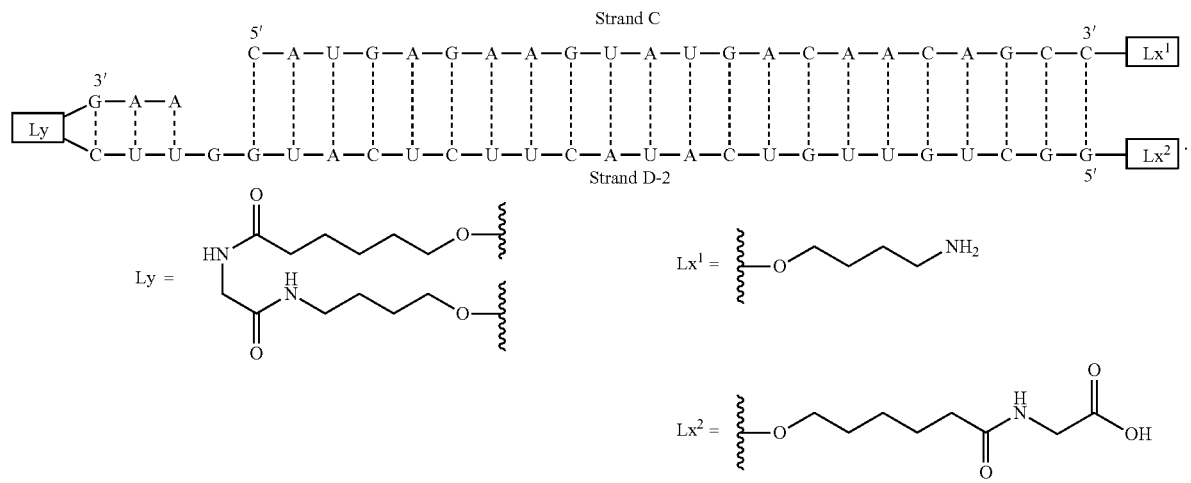

Strand C and strand D-2 were synthesized by phosphoramidite chemistry using an automated nucleic acid synthesizer (ABI3900; Applied Biosystems, Inc.). For this synthesis, TBDMS amidite was used as an RNA amidite. For the 3' end of the strand D-2, 2'-O-TBDMS-adenosine(N-Bz)-3'-lcaa-CPG (ChemGenes Corp.) was used; DMTr-diamidoglycine amidite (compound 16) was used as a special amidite for linking Ly; and cyanoethylglycine amidite (compound 20) was used for linking $Lx^2$. For the 3' end of the strand C, 3'-PT Amino-Modifier C4 CPG (compound name: N-(4-(4,4'-dimethoxytrityloxy)-butyl)-(2-carboxyamido)-phthalimidyl-lcaa-CPG; ChemGenes Corp.) was used. Solid-phase nucleic acid synthesis and deprotection reaction after the synthesis were carried out according to conventional methods.

An aqueous sodium chloride solution and 2-propanol were added to a reaction solution after the end of deprotection reaction of each strand, which was then centrifuged and a supernatant was removed. The obtained precipitate was dissolved in water for injection. The obtained products were verified to have the molecular weight of interest by mass spectrometry. The collected products of interest were strand C having non-nucleotide linker $Lx^1$ having an amino group at the 3' end (mass spectrometry found: 7222.9, calcd: 7222.4) and strand D-2 having non-nucleotide linker $Lx^2$ having a carboxyl group at the 5' end (mass spectrometry found: 9773.3, calcd: 9772.9).

100 nmol aliquots were taken from an aqueous solution of strand C and an aqueous solution of strand D-2 and mixed. The solvent was distilled away using a centrifugal concentrator, thereby drying the solution. The obtained residue was dissolved by the addition of 10 µL of a 1 M MOPS buffer solution, and the solution was heated to 95° C. and then allowed to cool to room temperature. 10 µL of a 0.2 M solution of HATU in DMSO was added thereto, and the mixture was stirred and then allowed to stand at room temperature for 4 hours. To the reaction solution, 2 µL of a 2 M aqueous sodium chloride solution and 50 µL of ethanol were added, and the mixture was stirred, allowed to stand at −30° C., and then centrifuged and a supernatant was removed. The obtained precipitate was dried. The obtained product was verified to have the molecular weight of interest by mass spectrometry (found: 16977.6, calcd: 16977.3).

INDUSTRIAL APPLICABILITY

We enable efficient production of a hairpin single-stranded RNA molecule containing an expression-inhibiting sequence for a target gene.

Sequence List Free Text

SEQ ID NOs: 1 to 6: synthetic RNAs

All publications, patents, and patent applications cited herein are incorporated herein by reference in their entirety.

The invention claimed is:

1. A method of producing a hairpin single-stranded RNA molecule capable of inhibiting expression of a target gene, comprising:

reacting a first single-stranded oligo-RNA molecule represented by formula (I) with a second single-stranded oligo-RNA molecule represented by formula (II) in a mixed solvent comprising a buffer solution and a hydrophilic organic solvent in the presence of a dehydration condensation agent:

wherein, in formula (I) or (II), X, Xc, Y and Yc each is composed of a ribonucleotide residue, Xc is complementary to X, Yc is complementary to Y, Ly is a non-nucleotide linker, $Lx^1$ is a non-nucleotide linker having an amino group, $Lx^2$ is a non-nucleotide linker having a carboxyl group, and X—Y comprises a gene expression-inhibiting sequence for the target gene, the dehydration condensation agent is selected from the group consisting of a triazine-based dehydration condensation agent, a uronium-based dehydration condensation agent comprising an N-hydroxy nitrogen-containing aromatic ring structure, a carbodiimide-based dehydration condensation agent, a 2-halopyridinium-based dehydration condensation agent, and a formamidinium-based dehydration condensation agent, if the dehydration condensation agent is the carbodiimide-based dehydration condensation agent, the dehydration condensation agent is used in combination with an N-hydroxy nitrogen-containing aromatic compound or a cyano(hydroxyimino)acetic acid ester, if the dehydration condensation agent is the 2-halopyridinium-based dehydration condensation agent, the dehydration condensation agent is used in combination with an N-hydroxy nitrogen-containing aromatic compound, and if the dehydration condensation agent is the formamidinium-based dehydration condensation agent, the dehydration condensation agent is used in combination with an N-hydroxy nitrogen-containing aromatic compound or an N-hydrocarbon-substituted imidazole derivative.

2. The method according to claim 1, wherein the linker Ly is a non-nucleotide linker having an amino acid backbone or an amino alcohol backbone, and the linker $Lx^2$ is a non-nucleotide linker having an amino acid backbone.

3. The method according to claim 1, wherein the Ly is a non-nucleotide linker comprising at least one of a pyrrolidine backbone or a piperidine backbone, or a non-nucleotide linker comprising —NHCH₂COO—, and the $Lx^2$ is a non-nucleotide linker comprising at least one of a pyrrolidine backbone or a piperidine backbone and having a carboxyl group, or a non-nucleotide linker comprising —NHCH₂COOH.

4. The method according to claim 1, wherein $Lx^1$ is represented by formula (III):

wherein, in formula (III), $R^1$ is an optionally substituted alkylene chain, and —OR' is bonded to the 3' end of Xc via a phosphodiester bond, and $Lx^2$ is represented by formula (IV) or formula (IV'):

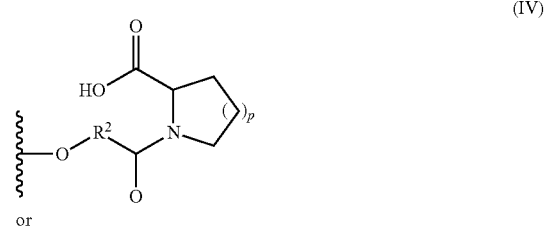

or

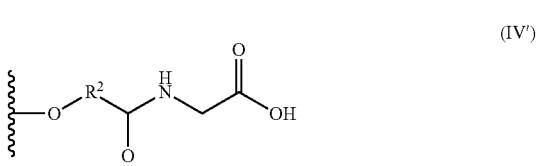

wherein, in formula (IV), R² is an optionally substituted alkylene chain, p is 1 or 2, and —OR² is bonded to the 5' end of X via a phosphodiester bond; and in formula (IV'), R² is an optionally substituted alkylene chain, and —OR² is bonded to the 5' end of X via a phosphodiester bond.

5. The method according to claim 1, wherein at least one of:
(i) the uronium-based dehydration condensation agent comprising an N-hydroxy nitrogen-containing aromatic ring structure is a benzotriazolyluronium-based dehydration condensation agent,
(ii) the N-hydroxy nitrogen-containing aromatic compound is hydroxybenzotriazole or a derivative thereof,
(iii) the cyano(hydroxyimino)acetic acid ester is a cyano(hydroxyimino)acetic acid alkyl ester, and
(iv) the N-hydrocarbon-substituted imidazole derivative is an N-alkylimidazole derivative.

6. The method according to claim 1, wherein the hydrophilic organic solvent is a hydrophilic aprotic organic solvent.

7. The method according to claim 6, wherein the hydrophilic aprotic organic solvent is dimethyl sulfoxide, N,N-dimethylformamide, N,N'-dimethylethyleneurea, or acetonitrile.

8. The method according to claim 1,
wherein the dehydration condensation agent is 4-(4,6-dimethoxy-1,3,5-triazin-2-yl)-4-methylmorpholinium chloride, O-(7-azabenzotriazol-1-yl)-N,N,N',N'-tetramethyluronium hexa-fluoroophosphate, N-(3'-dimethylaminopropyl)-N'-ethylcarbodiimide hydrochloride, 2-chloro-1-methylpyridinium iodide, or chloro-N,N,N',N'-tetramethylformamidinium hexafluorophosphate,
the N-hydroxy nitrogen-containing aromatic compound is 1-hydroxy-7-azabenzotriazole,
the cyano(hydroxyimino)acetic acid ester is ethyl cyano(hydroxyimino)acetate, and
the N-hydrocarbon-substituted imidazole derivative is N-methylimidazole.

9. The method according to claim 7, wherein a combination of the dehydration condensation agent and the hydrophilic aprotic organic solvent is a combination of O-(7-azabenzotriazol-1-yl)-N,N,N',N'-tetramethyluronium hexafluorophosphate and dimethyl sulfoxide, a combination of O-(7-azabenzotriazol-1-yl)-N,N,N',N'-tetramethyluronium hexafluorophosphate and N,N-dimethylformamide, a combination of N-(3'-dimethylaminopropyl)-N'-ethylcarbodiimide hydrochloride, 1-hydroxy-7-azabenzotriazole and dimethyl sulfoxide, or a combination of chloro-N,N,N',N'-tetramethylformamidinium hexafluorophosphate, 1-hydroxy-7-azaben-zotriazole and dimethyl sulfoxide.

10. The method according to claim 1, wherein pH of the buffer solution is 6.5 to 7.5.

11. The method according to claim 1, wherein Ly is a non-nucleotide linker comprising a pyrrolidine backbone or a piperidine backbone, Lx¹ is a non-nucleotide linker having an amino group, and Lx² is a non-nucleotide linker comprising at least one of a pyrrolidine backbone or a piperidine backbone and having a carboxyl group.

12. The method according to claim 1, wherein Ly is represented by formula (V):

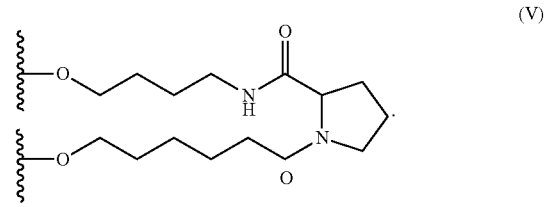

13. The method according to claim 1, wherein Lx¹ is represented by formula (VI):

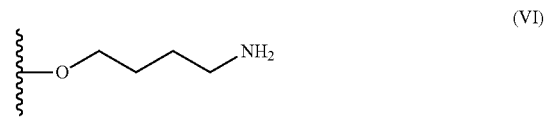 [SMILES: *OCCCCN]

and Lx² is represented by formula (VII):

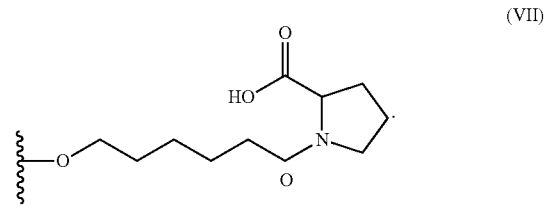

14. The method according to claim 1, wherein the target gene is TGF-β1 gene.

15. The method according to claim 1, wherein the hairpin single-stranded RNA molecule comprises the nucleotide sequence set forth in SEQ ID NO: 1.

* * * * *

SEQUENCE LISTING

```
<160> NUMBER OF SEQ ID NOS: 6

<210> SEQ ID NO 1
<211> LENGTH: 51
<212> TYPE: RNA
<213> ORGANISM: Artificial
<220> FEATURE:
<223> OTHER INFORMATION: synthetic
<220> FEATURE:
<221> NAME/KEY: modified_base
<222> LOCATION: (24)..(25)
<223> OTHER INFORMATION: nucleotides 24 and 25 are connected via a
      linker
<220> FEATURE:
<221> NAME/KEY: modified_base
<222> LOCATION: (50)..(51)
<223> OTHER INFORMATION: nucleotides 50 and 51 are connected via a
```

-continued

```
      linker

<400> SEQUENCE: 1
agcagaguac acacagcaua uaccgguaua ugcugugugu acucugcuuc g          51

<210> SEQ ID NO 2
<211> LENGTH: 24
<212> TYPE: RNA
<213> ORGANISM: Artificial
<220> FEATURE:
<223> OTHER INFORMATION: synthetic
<220> FEATURE:
<221> NAME/KEY: modified_base
<222> LOCATION: (24)
<223> OTHER INFORMATION: nucleotide 24 is connected to a linker

<400> SEQUENCE: 2
agcagaguac acacagcaua uacc                                        24

<210> SEQ ID NO 3
<211> LENGTH: 27
<212> TYPE: RNA
<213> ORGANISM: Artificial
<220> FEATURE:
<223> OTHER INFORMATION: synthetic
<220> FEATURE:
<221> NAME/KEY: modified_base
<222> LOCATION: (1)
<223> OTHER INFORMATION: nucleotide 1 is connected to a linker
<220> FEATURE:
<221> NAME/KEY: modified_base
<222> LOCATION: (26)..(27)
<223> OTHER INFORMATION: nucleotides 26 and 27 are connected via a
      linker

<400> SEQUENCE: 3
gguauaugcu guguguacuc ugcuucg                                     27

<210> SEQ ID NO 4
<211> LENGTH: 51
<212> TYPE: RNA
<213> ORGANISM: Artificial
<220> FEATURE:
<223> OTHER INFORMATION: synthetic
<220> FEATURE:
<221> NAME/KEY: modified_base
<222> LOCATION: (22)..(23)
<223> OTHER INFORMATION: nucleotides 22 and 23 are connected via a
      linker
<220> FEATURE:
<221> NAME/KEY: modified_base
<222> LOCATION: (48)..(49)
<223> OTHER INFORMATION: nucleotides 48 and 49 are connected via a
      linker

<400> SEQUENCE: 4
caugagaagu augacaacag ccggcuguug ucauacuucu caugguucga a          51

<210> SEQ ID NO 5
<211> LENGTH: 22
<212> TYPE: RNA
<213> ORGANISM: Artificial
<220> FEATURE:
<223> OTHER INFORMATION: synthetic
<220> FEATURE:
<221> NAME/KEY: modified_base
<222> LOCATION: (22)
<223> OTHER INFORMATION: nucleotide 22 is connected to a linker

<400> SEQUENCE: 5
```

```
caugagaagu augacaacag cc                                                      22

<210> SEQ ID NO 6
<211> LENGTH: 29
<212> TYPE: RNA
<213> ORGANISM: Artificial
<220> FEATURE:
<223> OTHER INFORMATION: synthetic
<220> FEATURE:
<221> NAME/KEY: modified_base
<222> LOCATION: (1)
<223> OTHER INFORMATION: nucleotide 1 is connected to a linker
<220> FEATURE:
<221> NAME/KEY: modified_base
<222> LOCATION: (26)..(27)
<223> OTHER INFORMATION: nucleotides 26 and 27 are connected via a
      linker

<400> SEQUENCE: 6
ggcuguuguc auacuucuca ugguucgaa                                               29
```